(12) United States Patent
Preyer

(10) Patent No.: US 11,447,575 B2
(45) Date of Patent: Sep. 20, 2022

(54) BISPECIFIC ANTIBODY PLATFORM

(71) Applicant: Biogen MA Inc., Cambridge, MA (US)

(72) Inventor: Martin Preyer, Somerville, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 16/061,903

(22) PCT Filed: Dec. 15, 2016

(86) PCT No.: PCT/US2016/066865
§ 371 (c)(1),
(2) Date: Jun. 13, 2018

(87) PCT Pub. No.: WO2017/106462
PCT Pub. Date: Jun. 22, 2017

(65) Prior Publication Data
US 2019/0048098 A1 Feb. 14, 2019

Related U.S. Application Data

(60) Provisional application No. 62/269,664, filed on Dec. 18, 2015.

(51) Int. Cl.
| | | |
|---|---|---|
| C07K 16/46 | (2006.01) | |
| C07K 16/28 | (2006.01) | |
| A61K 39/395 | (2006.01) | |
| C07K 14/765 | (2006.01) | |
| C07K 16/32 | (2006.01) | |

(52) U.S. Cl.
CPC .......... *C07K 16/468* (2013.01); *A61K 39/395* (2013.01); *C07K 14/765* (2013.01); *C07K 16/2863* (2013.01); *C07K 16/32* (2013.01); *C07K 2317/31* (2013.01); *C07K 2317/524* (2013.01); *C07K 2317/526* (2013.01); *C07K 2317/55* (2013.01); *C07K 2317/60* (2013.01); *C07K 2317/66* (2013.01); *C07K 2319/31* (2013.01)

(58) Field of Classification Search
CPC .......... C07K 2317/60; C07K 2317/524; C07K 2317/66; C07K 16/468
USPC ..................... 424/133.1; 530/387.3
See application file for complete search history.

(56) References Cited

U.S. PATENT DOCUMENTS

| | | | |
|---|---|---|---|
| 9,738,707 B2 * | 8/2017 | Taylor .................... | C07K 16/00 |
| 2012/0237507 A1 * | 9/2012 | Bossenmaier ......... | C07K 16/00 |
| | | | 424/133.1 |
| 2018/0057567 A1 * | 3/2018 | Rao ....................... | C07K 16/244 |
| 2018/0194861 A1 * | 7/2018 | Dong .................... | C07K 16/468 |
| 2020/0190213 A1 * | 6/2020 | Preyer ................ | C07K 16/2809 |

FOREIGN PATENT DOCUMENTS

| | | |
|---|---|---|
| CN | 101903404 | 12/2010 |
| CN | 104379604 | 2/2015 |
| WO | WO2013156148 | 10/2013 |
| WO | WO2015058048 | 4/2015 |
| WO | WO2017011342 | 1/2017 |

OTHER PUBLICATIONS

Worn et al. (J. Mol. Biol. (2001) 305, 989-1010).*
Cooke et al. (MABS 10(8):1248-1259 (2018)).*
PCT International Preliminary Report on Patentability (Chapter 1 of the PCT) in International Application No. PCT/US2016/066865, dated Jun. 28, 2018, 7 pages.
PCT International Search Report and Written Opinion in International Application No. PCT/US2016/066865, dated Mar. 13, 2017, 12 pages.
Seifert et al., "Tetravalent Antibody-scTRAIL Fusion Proteins with Improved Properties", Molecular Cancer Therapeutics, 2014(1); 101-11, Published Online Oct. 3, 2013; DOI: 10.1158/1535-7163. MCT-13-0396.
Seifert et al., "The IgM CH2 Domain as Covalently Linked Homodimerization Module for the Generation of Fusion Proteins with Dual Specificity", Protein Engineering, Design and Selection, Oct. 2012, 25(10):603-612; Published Online Sep. 17, 2012 DOI:IO. I093/protein/gzs059.

* cited by examiner

*Primary Examiner* — Lynn A Bristol
(74) *Attorney, Agent, or Firm* — Fish & Richardson P.C.

(57) ABSTRACT

Provided herein is a platform technology for the generation of properly paired bispecific antibodies. Some of the antibodies generated have Fc region modifications, in particular in their CH3 domains by lysine repositioning to drive heterodimerization of the two heavy chains of the bispecific antibody. Some of the antibodies generated have Fab arm modifications to prevent mispairing of light chains. Specifically, the CH1 and CL domains of one of the Fab arms of the bispecific antibody are substituted with an IgE CH2 domain or an IgM CH2 domain.

25 Claims, 27 Drawing Sheets

Specification includes a Sequence Listing.

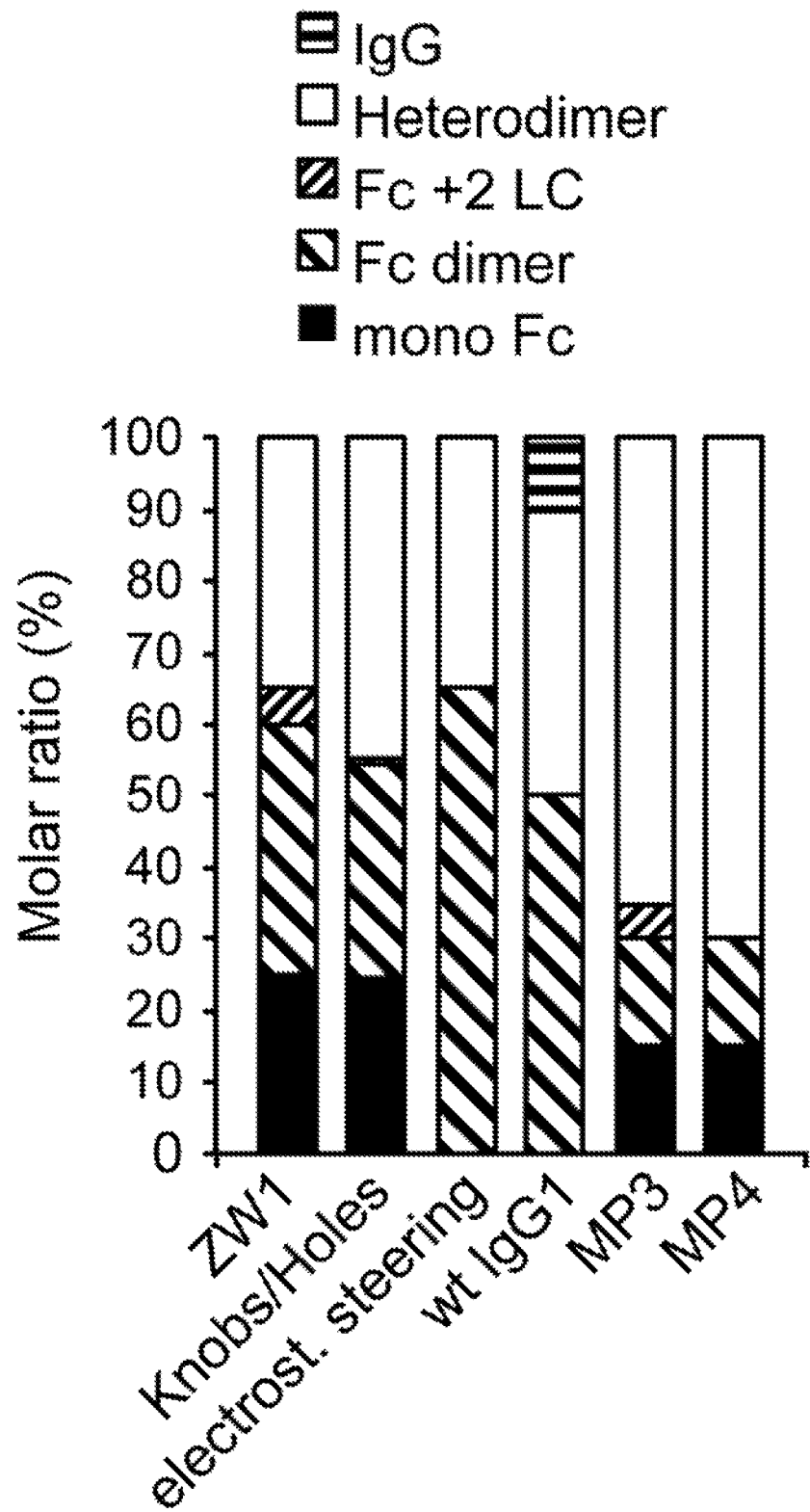

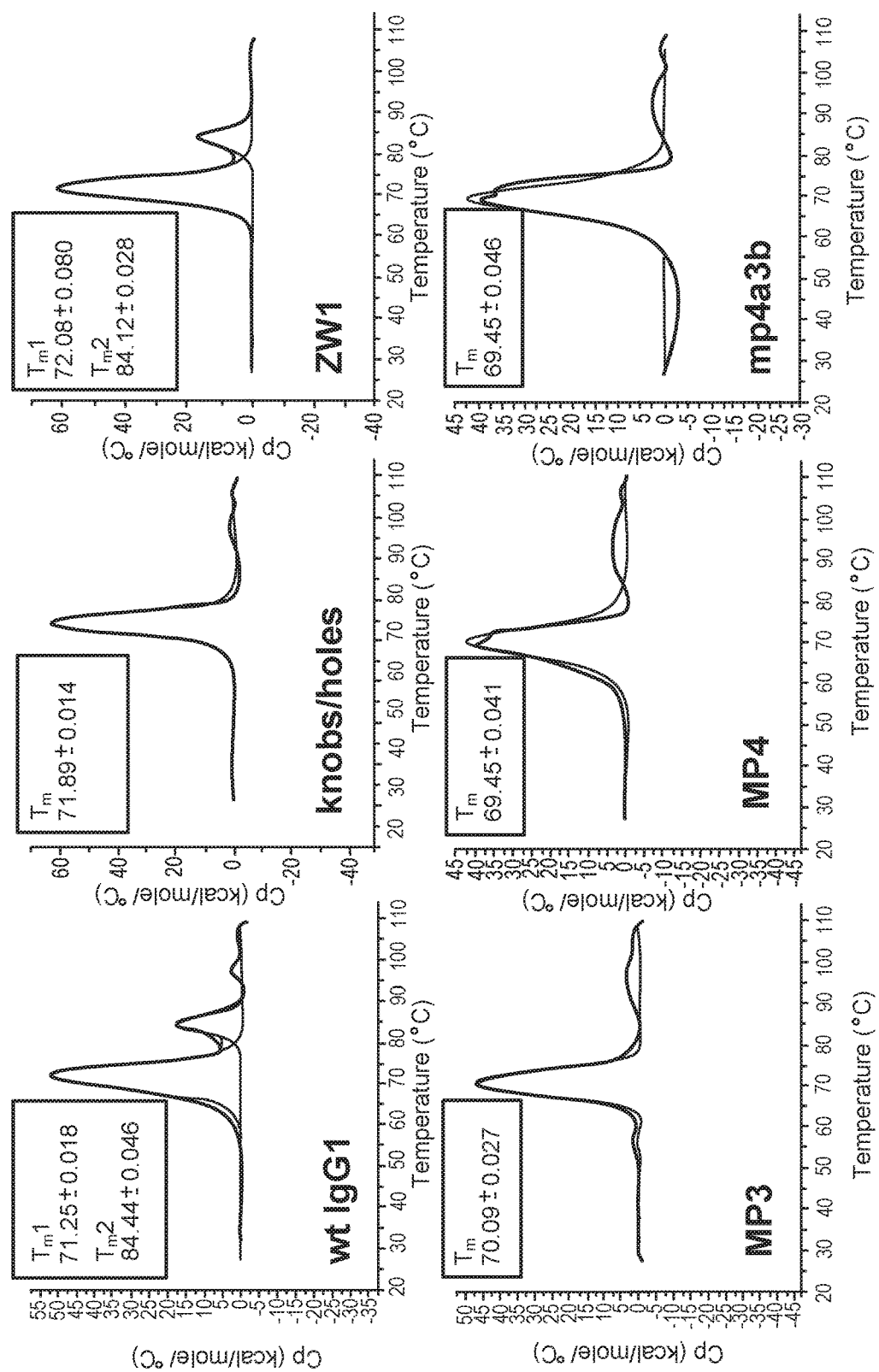

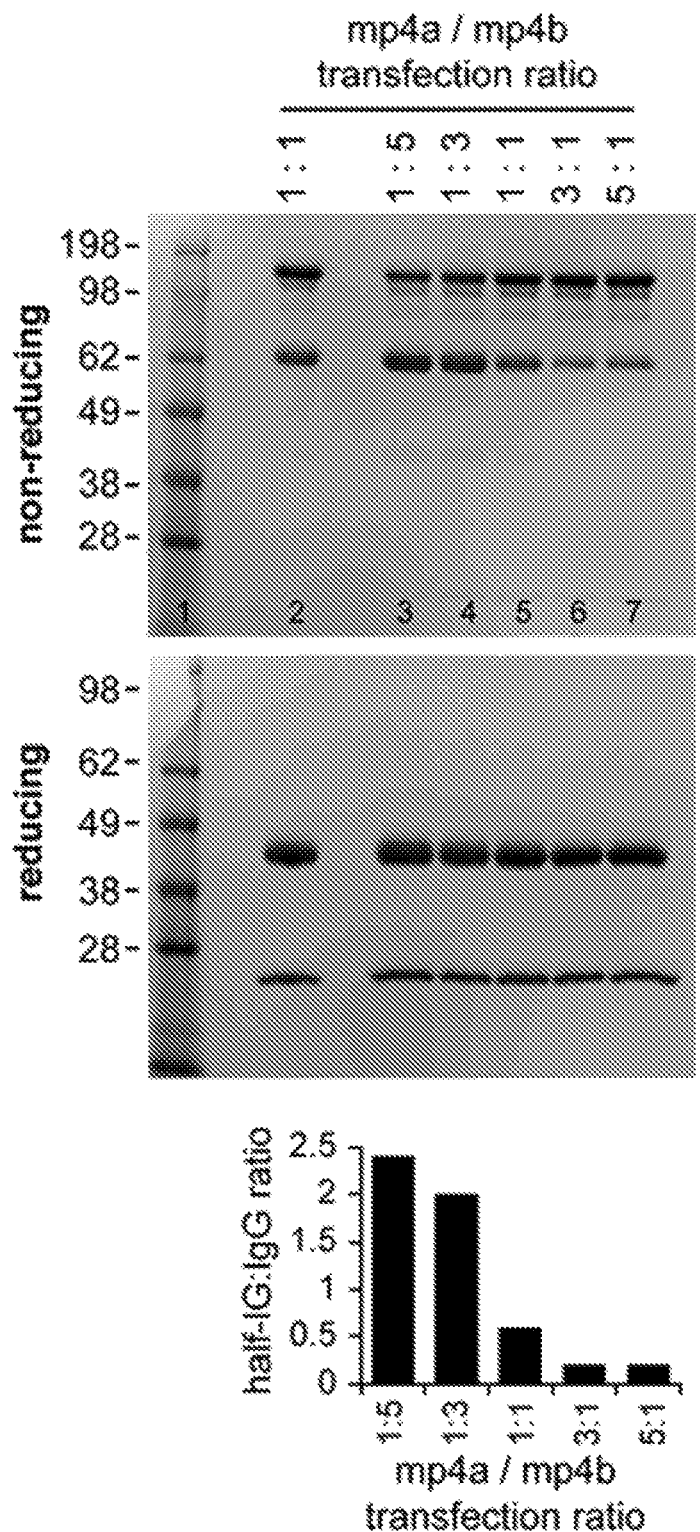

Figure 5C

```
                    A                 B
              ────────────▶       ────────────▶
              1       10   15    16    23 26   27              38
           7654321|........|....|123|......|..|   |..........|
CH1/hinge  ...ASTKGPSVFPLAPSSKSTS...GGTAALGCLVK   DYFP..EPVT
Ckappa     ...RTVAAPSVFIFPPSDEQLK...SGTASVVCLLN   NFYP..REAK
IgE CH2    VCSRDFTPPTVKILQSSCDGGGHF.PPTIQLLCLVS   GYTP..GTIN
EFab HC    ...ASTKGPTVKILQSSCDGGGHF.PPTIQLLCLVS   GYTP..GTIQ
Efab LC    ...RTVAAPTVKILQSSCDGGGHF.PPTIQLLCLVS   GYTP..GTIQ C                 D                      E
           ──────▶          ──────▶              ────────────▶
           39    45         77    84             85   89    96
           |.....|1234567|......|123454321|...|......|12
CH1/hinge  VSWNSGALTS....GVHTFPAVLQSS.GLYSLSSVVTVPSSSL..
Ckappa     VQWKVDNALQSG..NSQESVTEQDSKDSTYSLSSTLTLSKADY..
IgE CH2    ITWLEDGQVMD...VDLSTASTTQEG.ELASTQSELTLSQKHW..
EFab HC    ITWLEDGQVMD...VDLSTASTTQEG.ELASTQSELTLSQKHW..
Efab LC    ITWLEDGQVMD...VDLSTASTTQEG.ELASTQSELTLSQKHW..

F                         G
           ──────▶                  ──────▶
           97    104       105          117 118
           |......|        |...........|    |.........
CH1/hinge  .GTQTYIC         NVNHKP..SNTKV    DKKVEPKSCDKTHTCPPCP
Ckappa     EKHKVYAC         EVTHQG..LSSPV    TKSFNRGEC
IgE CH2    LSDRTYTC         QVTYQ....GHTF    EDSTKKCA
EFab HC    LSDRTYTC         QVTYQ....GHTF    EDSTKKCA
Efab LC    LSDRTYTC         QVTYQ....GHTF    EDSTKKCA
```

Figure 5D

```
human   VCSRDFTPPTVKILQSSCDGGGHFPPTIQLLCLVSGYTPGTINITWL-EDGQVMDVDLS-
chimp   .........-...V.............................-...........-
mouse       NI.E..LEL.H....PNA-.HS....Y.FIY.HILNDVSVS..MD.REIT.TLAQ-
rat         NI.K...DL.H....PNA-.HS....Y.F.Y.HIQNDVS.H..MD.RKIYETHAQ-
rabbit  A..VS....A.RLFH....PRENDTY.V.....I......D.EV...-V...KDPNMF.I human   TASTTQEGELASTQSELTLSQKHWLSDRTYTCQVTYQGHTFEDSTKKCA
chimp   ...A............................G..........
mouse   .VLIKE..K....C.K.NITEQQ.M.ES.F..K..S..VDYLAH.RR.
rat     NVLIKE..K....Y.R.NIT.QQ.M.ES.F..K..S..ENYWAH.RR.S
rabbit  ..QPR...K....H...NIT.GE.A.K....R.A...EL..AHARE.
```

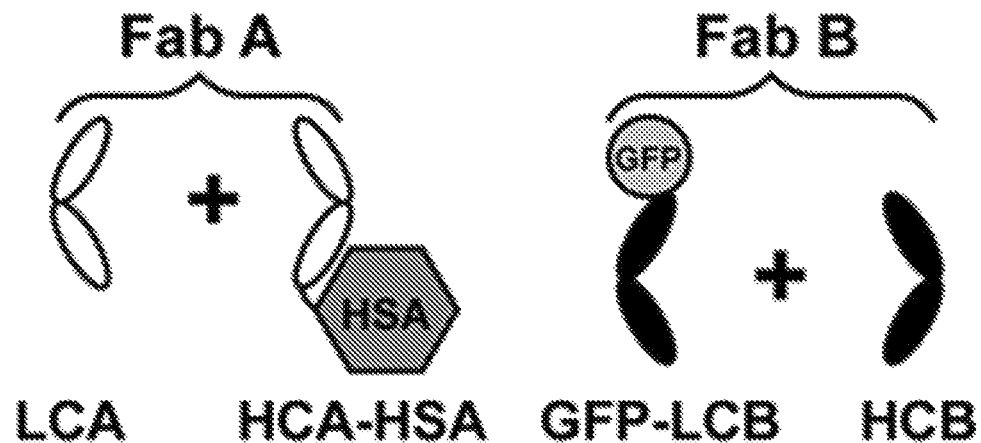

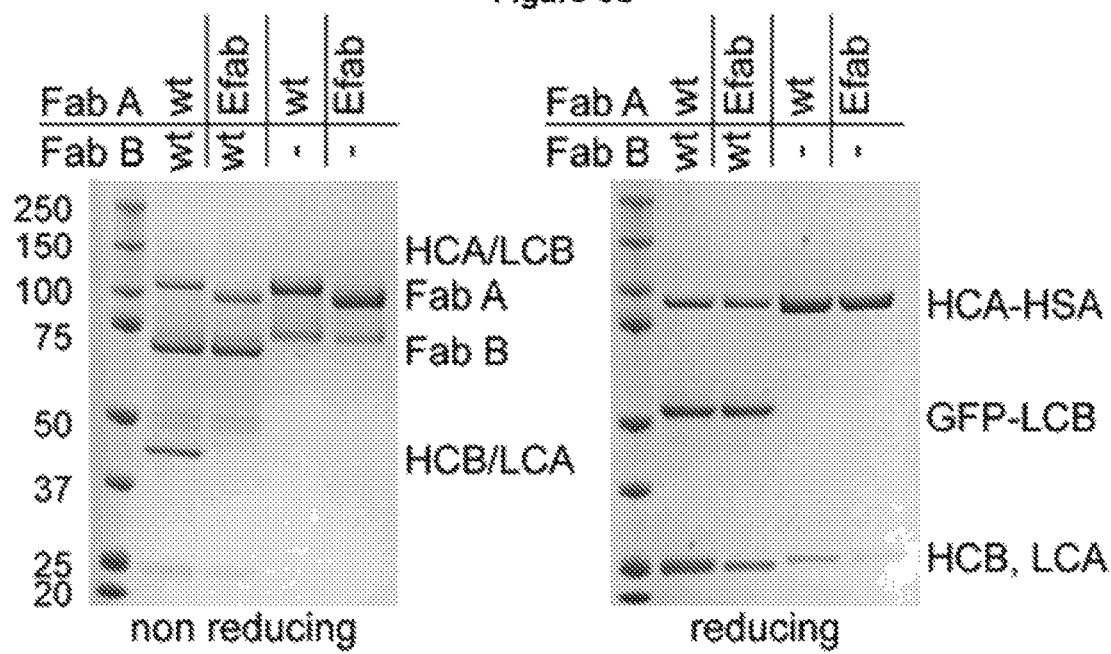

1. Substitute CH1/CL with IgE CH2 in one Fab arm

2. Engineered CH3 domain for heterodimerization by lysine rep

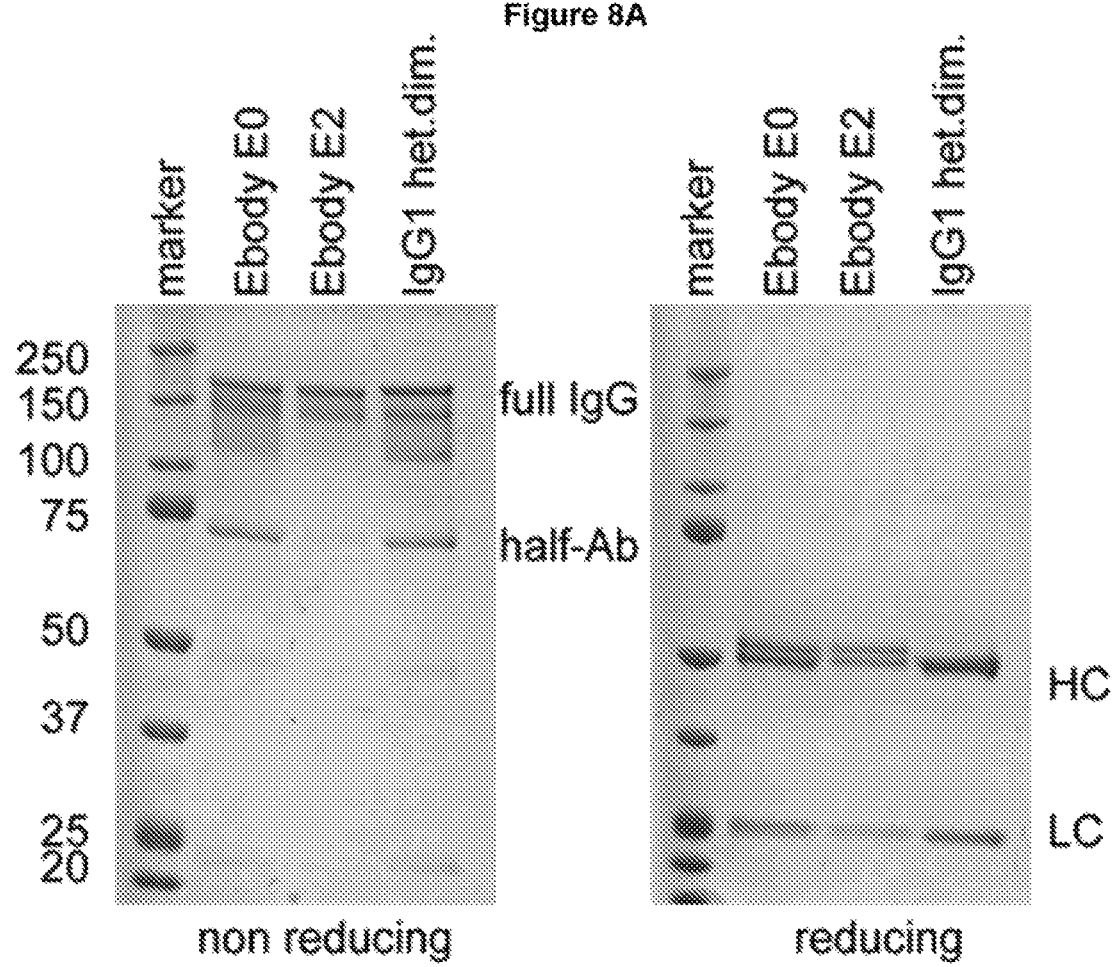

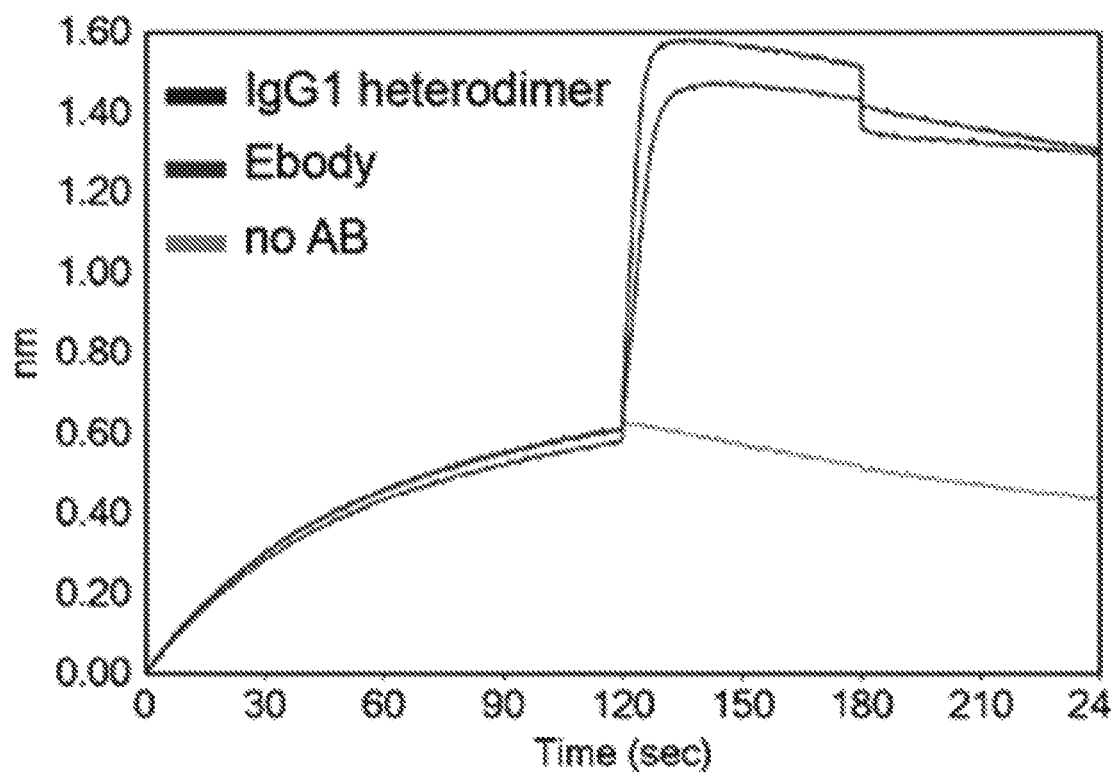

SEQUENCE LISTING

```
<160> NUMBER OF SEQ ID NOS: 106

<210> SEQ ID NO 1
<211> LENGTH: 107
<212> TYPE: PRT
<213> ORGANISM: Homo sapiens

<400> SEQUENCE: 1

Val Cys Ser Arg Asp Phe Thr Pro Pro Thr Val Lys Ile Leu Gln Ser
1               5                   10                  15
```

Ser Cys Asp Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
        35                  40                  45

Asp Gly Gln Val Met Asp Val Asp Leu Ser Thr Ala Ser Thr Thr Gln
    50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala
            100                 105

<210> SEQ ID NO 2
<211> LENGTH: 112
<212> TYPE: PRT
<213> ORGANISM: Homo sapiens

<400> SEQUENCE: 2

Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
            20                  25                  30

Thr Gly Phe Ser Pro Arg Gln Ile Gln Val Ser Trp Leu Arg Glu Gly
        35                  40                  45

Lys Gln Val Gly Ser Gly Val Thr Thr Asp Gln Val Gln Ala Glu Ala
    50                  55                  60

Lys Glu Ser Gly Pro Thr Thr Tyr Lys Val Thr Ser Thr Leu Thr Ile
65                  70                  75                  80

Lys Glu Ser Asp Trp Leu Gly Gln Ser Met Phe Thr Cys Arg Val Asp
                85                  90                  95

His Arg Gly Leu Thr Phe Gln Gln Asn Ala Ser Ser Met Cys Val Pro
            100                 105                 110

<210> SEQ ID NO 3
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Ala Ser Thr Lys Gly Pro Thr Val Lys Ile Leu Gln Ser Ser Cys Asp
1               5                   10                  15

Gly Gly Gly His Phe Pro Pro Thr Ile Gln Leu Leu Cys Leu Val Ser
            20                  25                  30

Gly Tyr Thr Pro Gly Thr Ile Gln Ile Thr Trp Leu Glu Asp Gly Gln
        35                  40                  45

Val Met Asp Val Asp Leu Ser Thr Ala Ser Thr Thr Gln Glu Gly Glu
    50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Thr Lys Lys Cys Ala
            100

<210> SEQ ID NO 4
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Arg Thr Val Ala Ala Pro Thr Val Lys Ile Leu Gln Ser Ser Cys Asp
1               5                   10                  15

Gly Gly Gly His Phe Pro Pro Thr Ile Gln Leu Leu Cys Leu Val Ser
                20                  25                  30

Gly Tyr Thr Pro Gly Thr Ile Gln Ile Thr Trp Leu Glu Asp Gly Gln
            35                  40                  45

Val Met Asp Val Asp Leu Ser Thr Ala Ser Thr Thr Gln Glu Gly Glu
        50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Thr Lys Lys Cys Ala
            100
```

<210> SEQ ID NO 5
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Ala Ser Thr Lys Gly Pro Thr Val Lys Ile Leu Gln Ser Ile Cys Asp
1               5                   10                  15

Gly Gly Gly His Phe Pro Pro Thr Ile Gln Leu Leu Cys Leu Val Ser
                20                  25                  30

Gly Tyr Thr Pro Gly Thr Ile Gln Ile Thr Trp Leu Glu Asp Gly Gln
            35                  40                  45

Val Met Asp Val Asp Leu Ser Thr Ala Ser Thr Thr Gln Glu Gly Glu
        50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Thr Lys Lys Cys Ala
            100
```

<210> SEQ ID NO 6
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

```
Arg Thr Val Ala Ala Pro Thr Val Lys Ile Leu Gln Ser Ser Cys Asp
1               5                   10                  15

Gly Gly Gly His Phe Pro Pro Thr Ile Gln Leu Leu Cys Leu Val Ser
                20                  25                  30

Gly Tyr Thr Pro Gly Thr Ile Gln Ile Thr Trp Leu Glu Asp Gly Gln
            35                  40                  45

Val Met Asp Val Asp Leu Ser Thr Ala Ser Thr Thr Gln Glu Gly Glu
        50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Gly Lys Lys Cys Ala
            100
```

<210> SEQ ID NO 7
<211> LENGTH: 5
<212> TYPE: PRT
<213> ORGANISM: Homo sapiens

<400> SEQUENCE: 7

```
Ala Ser Thr Lys Gly
1               5
```

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

```
Val Cys Ser Arg Asp Phe Thr Pro
1               5
```

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

```
Arg Thr Val Ala Ala
1               5
```

<210> SEQ ID NO 10
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

```
Gly Gly Gly Ser
1
```

-continued

```
<210> SEQ ID NO 11
<211> LENGTH: 107
<212> TYPE: PRT
<213> ORGANISM: Homo sapiens

<400> SEQUENCE: 11

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Gln Pro Arg Glu Pro Gln Val Tyr Thr Leu Pro Pro Ser Arg Asp
1               5                   10                  15

Glu Leu Thr Lys Asn Gln Val Lys Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
```

```
                    50                  55                  60
Phe Leu Tyr Ser Leu Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
                100                 105

<210> SEQ ID NO 14
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gly Gln Pro Arg Glu Pro Gln Val Tyr Thr Leu Pro Pro Ser Arg Asp
  1               5                  10                  15

Glu Leu Thr Lys Asn Gln Val Ser Leu Thr Cys Leu Val Ser Gly Phe
                 20                  25                  30

Tyr Pro Ser Asp Ile Ala Val Glu Trp Glu Ser Asn Gly Gln Pro Glu
                 35                  40                  45

Asn Asn Tyr Lys Thr Thr Pro Pro Ile Leu Asp Ser Asp Gly Ser Phe
 50                  55                  60

Lys Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
                100                 105

<210> SEQ ID NO 15
<211> LENGTH: 15
<212> TYPE: PRT
<213> ORGANISM: Homo sapiens

<400> SEQUENCE: 15

Glu Pro Lys Ser Cys Asp Lys Thr His Thr Cys Pro Pro Cys Pro
  1               5                  10                  15

<210> SEQ ID NO 16
<211> LENGTH: 12
<212> TYPE: PRT
<213> ORGANISM: Homo sapiens

<400> SEQUENCE: 16

Glu Ser Lys Tyr Gly Pro Pro Cys Pro Ser Cys Pro
  1               5                  10

<210> SEQ ID NO 17
<211> LENGTH: 12
<212> TYPE: PRT
<213> ORGANISM: Homo sapiens

<400> SEQUENCE: 17

Glu Ser Lys Tyr Gly Pro Pro Cys Pro Pro Cys Pro
  1               5                  10

<210> SEQ ID NO 18
```

```
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Lys
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Leu Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

```
<210> SEQ ID NO 19
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Ser Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Ile Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 20
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Gln Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Lys
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Leu Leu Thr Val
```

180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 21
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Gln Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Ser Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Ile Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 22
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Ala Ser Thr Lys Gly Pro Thr Val Lys Ile Leu Gln Ser Ile Cys Asp
1               5                   10                  15

Gly Gly Gly His Phe Pro Pro Thr Ile Gln Leu Leu Cys Leu Val Ser
                20                  25                  30

Gly Tyr Thr Pro Gly Thr Ile Gln Ile Thr Trp Leu Glu Asp Gly Gln
            35                  40                  45

Val Met Asp Val Asp Leu Ser Thr Ala Ser Thr Thr Gln Glu Gly Glu
    50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Thr Lys Lys Cys Ala Ser Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Gln Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Asp Glu Leu Thr Lys Asn Gln Val Lys Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Leu Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330

<210> SEQ ID NO 23
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
tgggctgcct ggtcaag                                                  17

```
<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
gtcagtttga cctggttctt g                                              21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
caagaaccag gtcaaactga c                                              21

<210> SEQ ID NO 26
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
gaattggccg ccctagatg                                                 19

<210> SEQ ID NO 27
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
tgggctgcct ggtcaag                                                   17

<210> SEQ ID NO 28
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ggtgaggctg ctgtagagga                                                20

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 29
tcctctacag cagcctcacc                                        20

<210> SEQ ID NO 30
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
gaattggccg ccctagatg                                         19

<210> SEQ ID NO 31
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
gctctgggtt ccaggttc                                          18

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gatagaagcc gctgaccagg                                        20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
cctggtcagc ggcttctatc                                        20

<210> SEQ ID NO 34
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
gaattggccg ccctagatg                                         19

<210> SEQ ID NO 35
<211> LENGTH: 18
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 35
gctctgggtt ccaggttc                                                       18

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
tgtagagttt gaaggagccg t                                                   21

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
acggctcctt caaactctac a                                                   21

<210> SEQ ID NO 38
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
gaattggccg ccctagatg                                                      19

<210> SEQ ID NO 39
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gly Gln Pro Arg Glu Pro Gln Val Tyr Thr Leu Pro Pro Ser Arg Asp
1               5                   10                  15

Glu Leu Thr Lys Asn Gln Val Lys Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Ser Leu Thr Val Asp Lys Ser Arg Trp Gln Gln Gly
65                  70                  75                  80

Asn Val Phe Ser Cys Ser Val Met His Glu Ala Leu His Asn His Tyr
```

```
                    85                  90                  95

Thr Gln Lys Ser Leu Ser Leu Ser Pro Gly
            100                 105

<210> SEQ ID NO 40
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Ser Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Lys Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 41
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gly Gln Pro Arg Glu Pro Gln Val Tyr Thr Leu Pro Pro Ser Arg Asp
1               5                   10                  15

Glu Leu Thr Lys Asn Gln Val Lys Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Leu Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 42
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 42

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Ser Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Ile Leu Asp Ser Asp Gly Ser Phe
    50                  55                  60

Lys Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 43
<211> LENGTH: 7119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
agcttgacat tgattattga ctagttatta atagtaatca attacggggt cattagttca      60
tagcccatat atggagttcc gcgttacata acttacggta atggcccgc ctggctgacc      120 gcccaacgac ccccgcccat tgacgtcaat aatgacgtat gttcccatag taacgccaat     180
agggactttc cattgacgtc aatgggtgga gtatttacgg taaactgccc acttggcagt     240
acatcaagtg tatcatatgc caagtacgcc ccctattgac gtcaatgacg gtaaatggcc     300
cgcctggcat tatgcccagt acatgacctt atgggacttt cctacttggc agtacatcta     360
cgtattagtc atcgctatta ccatggtgat gcggttttgg cagtacatca atgggcgtgg     420
atagcggttt gactcacggg gatttccaag tctccacccc attgacgtca atgggagttt     480
gttttggcac caaaatcaac gggactttcc aaaatgtcgt aacaactccg ccccattgac     540
gcaaatgggc ggtaggcgtg tacggtggga ggtctatata agcagagctc gtttagtgaa     600
ccgtcagatc gcctggagac gccatccacg ctgttttgac ctccatagaa gacaccggga     660
ccgatccagc ctccgcggcc gggaacggtg cattggaacg cggattcccc gtgccaagag     720
tgacgtaagt accgcctata gagtctatag gcccaccccc ttggcttctt atgcatgcta     780
tactgttttt ggcttggggt ctatacaccc ccgcttcctc atgttatagg tgatggtata     840
gcttagccta taggtgtggg ttattgacca ttattgacca ctcccctatt ggtgacgata     900
ctttccatta ctaatccata acatggctct ttgccacaac tctctttatt ggctatatgc     960
caatacactg tccttcagag actgacacgg actctgtatt tttacaggat ggggtctcat    1020
ttattattta caaattcaca tatacaacac caccgtcccc agtgcccgca gttttttatta  1080 aacataacgt gggatctcca cgcgaatctc gggtacgtgt tccggaacgg tggagggcag    1140
tgtagtctga gcagtactcg ttgctgccgc gcgcgccacc agacataata gctgacagac    1200
taacagactg ttcctttcca tgggtctttt ctgcagtcac cgtccttgac acgggatccg    1260

```
cggccgccac catgggttgg agcctcatct tgctcttcct tgtcgctgtt gctacgcgtg    1320
tcctgtccga ggtgcagctg ttggagtctg ggggaggctt ggtccagcct ggggggtccc    1380
tgagactctc ctgtgcagcc tctggattca ccttcagtga ctatattatg cactgggtcc    1440
gccaggctcc agggaagggg ctggagtggg tctcagttat tagtagttct ggtggcgaca    1500
catcctacgc agactccgtg aagggccgat tcaccatctc cagagacaat tccaagaaca    1560
cgctgtatct gcaaatgaac agcctgagag ccgaggacac ggccgtgtat tactgtgcga    1620
aagtcctcgc gggttacttc gactggttac cctttgacta ctggggccag ggaaccctgg    1680
tcaccgtctc gagcgcctcc accaagggcc catcggtctt ccccctggca ccctcctcca    1740
agagcacctc tgggggcaca gcggccctgg gctgcctggt caaggactac ttccccgaac    1800
cggtgacggt gtcgtggaac tcaggcgccc tgaccagcgg cgtgcacacc ttcccggctg    1860
tcctacagtc ctcaggactc tactccctca gcagcgtggt gaccgtgccc tccagcagct    1920
tgggcaccca gacctacatc tgcaacgtga atcacaagcc cagcaacacc aaggtggaca    1980
agaaagttga gcccaaatct tgtgacaaga ctcacacatg cccaccgtgc ccagcacctg    2040
aactcctggg gggaccgtca gtcttcctct tccccccaaa acccaaggac accctcatga    2100
tctcccggac ccctgaggtc acatgcgtgg tggtggacgt gagccacgaa gaccctgagg    2160
tcaagttcaa ctggtacgtg gacggcgtgg aggtgcataa tgccaagaca aagccgcggg    2220
aggagcagta caacagcacg taccgtgtgg tcagcgtcct caccgtcctg caccaggact    2280
ggctgaatgg caaggagtac aagtgcaagg tctccaacaa agccctccca gcccccatcg    2340
agaaaaccat ctccaaagcc aaagggcagc ccgagaacc acaggtgtac accctgcccc    2400
catcccggga tgagctgacc aagaaccagg tcaaactgac ctgcctggtc aaaggcttct    2460
atcccagcga catcgccgtg gagtgggaga gcaatgggca gccggagaac aactacaaga    2520
ccacgcctcc cgtgttggac tccgacggct ccttcttcct ctacagcctc tcaccgtgg    2580 acaagagcag gtggcagcag gggaacgtct tctcatgctc cgtgatgcat gaggctctgc    2640
acaaccacta cacgcagaag agcctctccc tgtctccggg ttagtaatta attaatgcat    2700
ctagggcggc caattccgcc cctctccctc ccccccccct aacgttactg gccgaagccg    2760
cttggaataa ggccggtgtg cgtttgtcta tatgtgattt tccaccatat tgccgtcttt    2820
tggcaatgtg agggcccgga aacctggccc tgtcttcttg acgagcattc ctaggggtct    2880
ttcccctctc gccaaaggaa tgcaaggtct gttgaatgtc gtgaaggaag cagttcctct    2940
ggaagcttct tgaagacaaa caacgtctgt agcgaccctt gcaggcagc ggaacccccc     3000 acctggcgac aggtgcctct gcggccaaaa gccacgtgta taagatacac ctgcaaaggc    3060
ggcacaaccc cagtgccacg ttgtgagttg atagttgtg gaaagagtca atggctctc     3120 ctcaagcgta ttcaacaagg ggctgaagga tgcccagaag gtaccccatt gtatgggatc    3180
tgatctgggg cctcggtgca catgctttac atgtgtttag tcgaggttaa aaaaacgtct    3240
aggccccccg aaccacgggg acgtggtttt cctttgaaaa acacgatgat aagcttgcca    3300
caagctagca tggttcgacc attgaactgc atcgtcgccg tgtcccaaaa tatgggatt    3360 ggcaagaacg gagacctacc ctggcctccg ctcaggaacg agttcaagta cttccaaaga    3420
atgaccacaa cctcttcagt ggaaggtaaa cagaatctgg tgattatggg taggaaaacc    3480
tggttctcca ttcctgagaa gaatcgacct ttaaaggaca gaattaatat agttctcagt    3540
agagaactca aagaaccacc acgaggagct cattttcttg ccaaaagttt ggatgatgcc    3600
ttaagactta ttgaacaacc ggaattggca agtaaagtag acatggtttg gatagtcgga    3660
```

```
ggcagttctg tttaccagga agccatgaat caaccaggcc acctcagact ctttgtgaca    3720
aggatcatgc aggaatttga aagtgacacg ttttcccag aaattgattt ggggaaatat    3780
aaacttctcc cagaataccc aggcgtcctc tctgaggtcc aggaggaaaa aggcatcaag    3840
tataagtttg aagtctacga gaagaaagac taatcgagaa ttgtctagac tgcccgggtg    3900
gcatccctgt gacccctccc cagtgcctct cctggtcgtg aaggtgcta ctccagtgcc    3960
caccagcctt gtcctaataa aattaagttg catcattttg tttgactagg tgtccttgta    4020
taatattatg gggtggaggc gggtggtatg gagcaagggg caggttggga agacaacctg    4080
tagggccttc agggtctatt gggaaccagg ctggagtgca gtggcacgat cttggctcgc    4140
tgcaatctcc gcctcctggg ttcaagcgat tctcctgcct cagtctcccg aatagttggg    4200
attccaggca tgcacgacca ggctcagcta attttgtat ttttggtaga acgggggttt    4260
caccatattg gccagtctgg tctccatctc ctgacctcag gtaatccgcc cgcctcggcc    4320
tcccaaattg ctgggattac aggtatgagc cactgggccc ttccctgtcc tgtgattta    4380
aaataattat accagcagaa ggacgtccag acacagcatg ggctacctgg ccatgcccag    4440
ccagttggac atttgagttg tttgcttggc actgtcctct catcaattca ctggccgtcg    4500
ttttacaacg tcgtgactgg gaaaaccctg gcgttaccca acttaatcgc cttgcagcac    4560
atccccnttt cgccagctgg cgtaatagcg aagaggcccg caccgatcgc ccttcccaac    4620
agttgcgcag cctgaatggc gaatggcgcc tgatgcggta tttttctcctt acgcatctgt    4680
gcggtatttc acaccgcata tggtgcactc tcagtacaat ctgctctgat gccgcatagt    4740
taagccagcc ccgacacccg ccaacacccg ctgacgcgcc ctgacgggct tgtctgctcc    4800
cggcatccgc ttacagacaa gctgtgaccg tctccgggag ctgcatgtgt cagaggtttt    4860
caccgtcatc accgaaacgc gcgagacgaa agggcctcgt gatacgccta ttttataggg    4920
ttaatgtcat gataataatg gtttcttaga cgtcaggtgg cacttttcgg ggaaatgtgc    4980
gcggaacccc tatttgttta ttttctaaa tacattcaaa tatgtatccg ctcatgagac    5040
aataaccctg ataaatgctt caataatatt gaaaaaggaa gagtatgagt attcaacatt    5100
tccgtgtcgc ccttattccc tttttgcgg cattttgcct tcctgttttt gctcacccag    5160
aaacgctggt gaaagtaaaa gatgctgaag atcagttggg tgcacgagtg ggttacatcg    5220
aactggatct caacagcggt aagatccttg agagttttcg ccccgaagaa cgttttccaa    5280
tgatgagcac ttttaaagtt ctgctatgtg gcgcggtatt atcccgtatt gacgccgggc    5340
aagagcaact cggtcgccgc atacactatt ctcagaatga cttggttgag tactcaccag    5400
tcacagaaaa gcatcttacg gatggcatga cagtaagaga attatgcagt gctgccataa    5460
ccatgagtga taacactgcg gccaacttac ttctgacaac gatcggagga ccgaaggagc    5520
taaccgcttt tttgcacaac atgggggatc atgtaactcg ccttgatcgt tgggaaccgg    5580
agctgaatga agccatacca aacgacgagc gtgacaccac gatgcctgta gcaatggcaa    5640
caacgttgcg caaactatta actggcgaac tacttactct agcttcccgg caacaattaa    5700
tagactggat ggaggcggat aaagttgcag gaccacttct gcgctcggcc cttccggctg    5760
gctggtttat tgctgataaa tctgagccg gtgagcgtgg gtctcgcggt atcattgcag    5820
cactggggcc agatggtaag ccctcccgta tcgtagttat ctacacgacg gggagtcagg    5880
caactatgga tgaacgaaat agacagatcg ctgagatagg tgcctcactg attaagcatt    5940
ggtaactgtc agaccaagtt tactcatata ctttagat tgatttaaaa cttcatttt    6000
```

```
aatttaaaag gatctaggtg aagatccttt ttgataatct catgaccaaa atcccttaac      6060
gtgagttttc gttccactga gcgtcagacc ccgtagaaaa gatcaaagga tcttcttgag      6120
atcctttttt tctgcgcgta atctgctgct tgcaaacaaa aaaaccaccg ctaccagcgg      6180
tggtttgttt gccggatcaa gagctaccaa ctcttttccc gaaggtaact ggcttcagca      6240
gagcgcagat accaaatact gttcttctag tgtagccgta gttaggccac cacttcaaga      6300
actctgtagc accgcctaca tacctcgctc tgctaatcct gttaccagtg gctgctgcca      6360
gtggcgataa gtcgtgtctt accgggttgg actcaagacg atagttaccg gataaggcgc      6420
agcggtcggg ctgaacgggg ggttcgtgca cacagcccag cttggagcga acgacctaca      6480
ccgaactgag atacctacag cgtgagctat gagaaagcgc cacgcttccc gaagggagaa      6540
aggcggacag gtatccggta agcggcaggg tcggaacagg agagcgcacg agggagcttc      6600 caggggaaa cgcctggtat ctttatagtc ctgtcgggtt tcgccacctc tgacttgagc      6660
gtcgattttt gtgatgctcg tcaggggggc ggagcctatg gaaaaacgcc agcaacgcgg      6720
cctttttacg gttcctggcc ttttgctggc cttttgctca catgttcttt cctgcgttat      6780
cccctgattc tgtggataac cgtattaccg cctttgagtg agctgatacc gctcgccgca      6840
gccgaacgac cgagcgcagc gagtcagtga gcgaggaagc ggaagagcgc ccaatacgca      6900
aaccgcctct ccccgcgcgt tggccgattc attaatgcag ctggcacgac aggtttcccg      6960
actggaaagc gggcagtgag cgcaacgcaa ttaatgtgag ttagctcact cattaggcac      7020
cccaggcttt acactttatg cttccggctc gtatgttgtg tggaattgtg agcggataac      7080
aatttcacac aggaaacagc tatgaccatg attacgcca                            7119
```

<210> SEQ ID NO 44
<211> LENGTH: 6489
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

```
agcttgacat tgattattga ctagttatta atagtaatca attacggggt cattagttca       60
tagcccatat atggagttcc gcgttacata acttacggta aatggcccgc ctggctgacc      120
gcccaacgac ccccgcccat tgacgtcaat aatgacgtat gttcccatag taacgccaat      180
agggactttc cattgacgtc aatgggtgga gtatttacgg taaactgccc acttggcagt      240
acatcaagtg tatcatatgc caagtacgcc ccctattgac gtcaatgacg gtaaatggcc      300
cgcctggcat tatgcccagt acatgacctt atgggacttt cctacttggc agtacatcta      360
cgtattagtc atcgctatta ccatggtgat gcggttttgg cagtacatca atgggcgtgg      420
atagcggttt gactcacggg gatttccaag tctccacccc attgacgtca atgggagttt      480
gttttggcac caaaatcaac gggactttcc aaaatgtcgt aacaactccg ccccattgac      540
gcaaatgggc ggtaggcgtg tacggtggga ggtctatata agcagagctc gtttagtgaa      600
ccgtcagatc gcctggagac gccatccacg ctgttttgac ctccatagaa gacaccggga      660
ccgatccagc ctccgcggcc gggaacggtg cattggaacg cggattcccc gtgccaagag      720
tgacgtaagt accgcctata gagtctatag gcccaccccc ttggcttctt atgcatgcta      780
tactgttttt ggcttggggt ctatacaccc ccgcttcctc atgttatagg tgatggtata      840
gcttagccta taggtgtggg ttattgacca ttattgacca ctcccctatt ggtgacgata      900
```

```
ctttccatta ctaatccata acatggctct tgccacaac tctctttatt ggctatatgc    960
caatacactg tccttcagag actgacacgg actctgtatt tttacaggat ggggtctcat   1020
ttattattta caaattcaca tatacaacac caccgtcccc agtgcccgca gtttttatta   1080
aacataacgt gggatctcca cgcgaatctc gggtacgtgt tccggaacgg tggagggcag   1140
tgtagtctga gcagtactcg ttgctgccgc gcgcgccacc agacataata gctgacagac   1200
taacagactg ttccttttca tgggtctttt ctgcagtcac cgtccttgac acgggatccg   1260
cggccgccat ggagacagac acactcctgc tatgggtact gctgctctgg gttccaggtt   1320
ccaccggtga caagactcac acatgcccac cgtgcccagc acctgaactc ctgggggac    1380
cgtcagtctt cctcttcccc ccaaaaccca aggacaccct catgatctcc cggacccctg   1440
aggtcacatg cgtggtggtg gacgtgagcc acgaagaccc tgaggtcaag ttcaactggt   1500
acgtggacgg cgtggaggtg cataatgcca agacaaagcc gcgggaggag cagtacaaca   1560
gcacgtaccg tgtggtcagc gtcctcaccg tcctgcacca ggactggctg aatggcaagg   1620
agtacaagtg caaggtctcc aacaaagccc tcccagcccc catcgagaaa accatctcca   1680
aagccaaagg gcagccccga gaaccacagg tgtacaccct gcccccatcc cgggatgagc   1740
tgaccaagaa ccaggtcagc ctgacctgcc tggtcagcgg cttctatccc agcgacatcg   1800
ccgtggagtg ggagagcaat gggcagccgg agaacaacta caagaccacg cctcccatct   1860
tggactccga cggctccttc aaactctaca gcaagctcac cgtggacaag agcaggtggc   1920
agcaggggaa cgtcttctca tgctccgtga tgcatgaggc tctgcacaac cactacacgc   1980
agaagagcct ctccctgtct ccgggttagt aattaattaa tgcatctagg gcggccaatt   2040
ccgcccctct ccctcccccc ccctaacgt tactggccga agccgcttgg aataaggccg   2100
gtgtgcgttt gtctatatgt tattttccac catattgccg tcttttggca atgtgagggc   2160
ccggaaacct ggccctgtct tcttgacgag cattcctagg ggtctttccc ctctcgccaa   2220
aggaatgcaa ggtctgttga atgtcgtgaa ggaagcagtt cctctggaag cttcttgaag   2280
acaaacaacg tctgtagcga ccctttgcag gcagcggaac cccccacctg gcgacaggtg   2340
cctctgcggc caaaagccac gtgtataaga tacacctgca aaggcggcac aaccccagtg   2400
ccacgttgtg agttggatag ttgtggaaag agtcaaatgg ctctcctcaa gcgtattcaa   2460
caaggggctg aaggatgccc agaaggtacc ccattgtatg ggatctgatc tggggcctcg   2520
gtgcacatgc tttacatgtg tttagtcgag gttaaaaaaa cgtctaggcc ccccgaacca   2580
cggggacgtg gttttccttt gaaaaacacg atgataatat ggccacaacc atggttaccg   2640
agtacaagcc cacggtgcgc ctcgccaccc gcgacgacgt ccccagggcc gtacgcaccc   2700
tcgccgccgc gttcgccgac taccccgcca cgcgccacac cgtcgatccg gaccgccaca   2760
tcgagcgggt caccgagctg caagaactct tcctcacgcg cgtcgggctc gacatcggca   2820
aggtgtgggt cgcggacgac ggcgccgcgg tggcggtctg gaccacgccg gagagcgtcg   2880
aagcgggggc ggtgttcgcc gagatcggcc cgcgcatggc cgagttgagc ggttcccggc   2940
tggccgcgca gcaacagatg gaaggcctcc tggcgccgca ccggcccaag gagcccgcgt   3000
ggttcctggc caccgtcggc gtctcgcccg accaccaggg caagggtctg ggcagcgccg   3060
tcgtgctccc cggagtggag gcggccgagc gcgccggggt gcccgccttc ctggagacct   3120
ccgcgccccg caacctcccc ttctacgagc ggctcggctt caccgtcacc gccgacgtcg   3180
aggtgcccga aggaccgcgc acctggtgca tgacccgcaa gcccggtgcc tgagtcgatg   3240
```

-continued

```
ataatcgatt agactgcccg ggtggcatcc ctgtgacccc tccccagtgc ctctcctggt     3300
cgtggaaggt gctactccag tgcccaccag ccttgtccta ataaaattaa gttgcatcat     3360
tttgtttgac taggtgtcct tgtataatat tatggggtgg aggcgggtgg tatggagcaa     3420
ggggcaggtt gggaagacaa cctgtagggc cttcagggtc tattgggaac caggctggag     3480
tgcagtggca cgatcttggc tcgctgcaat ctccgcctcc tgggttcaag cgattctcct     3540
gcctcagtct cccgaatagt tgggattcca ggcatgcacg accaggctca gctaattttt     3600 gtattttttgg tagagacggg gtttcaccat attggccagt ctggtatcca tctcctgacc     3660
tcaggtaatc cgcccgcctc ggcctcccaa attgctggga ttacaggtat gagccactgg     3720
gcccttccct gtcctgtgat tttaaaataa ttataccagc agaaggacgt ccagacacag     3780
catgggctac ctggccatgc ccagccagtt ggacatttga gttgtttgct tggcactgtc     3840
ctctcatcaa ttcgagctca ctggccgtcg ttttacaacg tcgtgactgg gaaaaccctg     3900
gcgttaccca acttaatcgc cttgcagcac atccccctttt cgccagctgg cgtaatagcg     3960
aagaggcccg caccgatcgc ccttcccaac agttgcgcag cctgaatggc gaatggcgcc     4020
tgatgcggta ttttctcctt acgcatctgt gcggtatttc acaccgcata tggtgcactc     4080
tcagtacaat ctgctctgat gccgcatagt taagccagcc ccgacacccg ccaacacccg     4140
ctgacgcgcc ctgacgggct tgtctgctcc cggcatccgc ttacagacaa gctgtgaccg     4200
tctccgggag ctgcatgtgt cagaggtttt caccgtcatc accgaaacgc gcgagacgaa     4260
agggcctcgt gatacgccta tttttatagg ttaatgtcat gataataatg gtttcttaga     4320
cgtcaggtgg cacttttcgg ggaaatgtgc gcggaacccc tatttgttta ttttttctaaa     4380 tacattcaaa tatgtatccg ctcatgagac aataaccctg ataaatgctt caataatatt     4440
gaaaaaggaa gagtatgagt attcaacatt tccgtgtcgc ccttattccc ttttttgcgg     4500
cattttgcct tcctgttttt gctcacccag aaacgctggt gaaagtaaaa gatgctgaag     4560
atcagttggg tgcacgagtg ggttacatcg aactggatct caacagcggt aagatccttg     4620
agagttttcg ccccgaagaa cgttttccaa tgatgagcac ttttaaagtt ctgctatgtg     4680
gcgcggtatt atcccgtatt gacgccgggc aagagcaact cggtcgccgc atacactatt     4740
ctcagaatga cttggttgag tactcaccag tcacagaaaa gcatcttacg gatggcatga     4800
cagtaagaga attatgcagt gctgccataa ccatgagtga taacactgcg gccaacttac     4860
ttctgacaac gatcggagga ccgaaggagc taaccgcttt tttgcacaac atgggggatc     4920
atgtaactcg ccttgatcgt tgggaaccgg agctgaatga agccatacca aacgacgagc     4980
gtgacaccac gatgcctgta gcaatggcaa caacgttgcg caaactatta actggcgaac     5040
tacttactct agcttcccgg caacaattaa tagactggat ggaggcggat aaagttgcag     5100
gaccacttct gcgctcggcc cttccggctg gctggtttat tgctgataaa tctggagccg     5160
gtgagcgtgg ttcccgcggt atcattgcag cactggggcc agatggtaag ccctcccgta     5220
tcgtagttat ctacacgacg gggagtcagg caactatgga tgaacgaaat agacagatcg     5280
ctgagatagg tgcctcactg attaagcatt ggtaactgtc agaccaagtt tactcatata     5340
tactttagat tgatttaaaa cttcatttt aatttaaaag gatctaggtg aagatccttt     5400
ttgataatct catgaccaaa atcccttaac gtgagttttc gttccactga gcgtcagacc     5460
ccgtagaaaa gatcaaagga tcttcttgag atccttttt tctgcgcgta atctgctgct     5520
tgcaaacaaa aaaaccaccg ctaccagcgg tggtttgttt gccggatcaa gagctaccaa     5580
ctctttttcc gaaggtaact ggcttcagca gagcgcagat accaaatact gttcttctag     5640
```

```
tgtagccgta gttaggccac cacttcaaga actctgtagc accgcctaca tacctcgctc    5700
tgctaatcct gttaccagtg gctgctgcca gtggcgataa gtcgtgtctt accgggttgg    5760
actcaagacg atagttaccg gataaggcgc agcggtcggg ctgaacgggg ggttcgtgca    5820
cacagcccag cttggagcga acgacctaca ccgaactgag atacctacag cgtgagctat    5880
gagaaagcgc cacgcttccc gaagggagaa aggcggacag gtatccggta agcggcaggg    5940
tcggaacagg agagcgcacg agggagcttc caggggggaaa cgcctggtat ctttatagtc    6000
ctgtcgggtt tcgccacctc tgacttgagc gtcgattttt gtgatgctcg tcagggggggc    6060 ggagcctatg gaaaaacgcc agcaacgcgg ccttttttacg gttcctggcc ttttgctggc    6120
cttttgctca catgttcttt cctgcgttat ccctgattc tgtggataac cgtattaccg    6180
cctttgagtg agctgatacc gctcgccgca gccgaacgac cgagcgcagc gagtcagtga    6240
gcgaggaagc ggaagggcgc ccaatacgca aaccgcctct ccccgcgcgt tggccgattc    6300
attaatgcag ctggcacgac aggtttcccg actggaaagc gggcagtgag cgcaacgcaa    6360
ttaatgtgag ttagctcact cattaggcac cccaggcttt acactttatg cttccggctc    6420
gtatgttgtg tggaattgtg agcggataac aatttcacac aggaaacagc tatgaccatg    6480
attacgcca                                                           6489
```

<210> SEQ ID NO 45
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Ala Ser Thr Lys Gly Pro Thr Val Lys Ile Leu Gln Ser Ser Cys Asp
1               5                   10                  15

Gly Gly Gly His Phe Pro Pro Thr Ile Gln Leu Leu Cys Leu Val Ser
            20                  25                  30

Gly Tyr Thr Pro Gly Thr Ile Asn Ile Thr Trp Leu Glu Asp Gly Gln
        35                  40                  45

Val Met Asp Val Asp Leu Ser Thr Ala Ser Thr Thr Gln Glu Gly Glu
    50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Thr Lys Lys Cys Ala
            100
```

<210> SEQ ID NO 46
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Arg Thr Val Ala Ala Pro Thr Val Lys Ile Leu Gln Ser Ser Cys Asp
1               5                   10                  15
```

```
Gly Gly Gly His Phe Pro Pro Thr Ile Gln Leu Leu Cys Leu Val Ser
            20                  25                  30

Gly Tyr Thr Pro Gly Thr Ile Asn Ile Thr Trp Leu Glu Asp Gly Gln
        35                  40                  45

Val Met Asp Val Asp Leu Ser Thr Ala Ser Thr Thr Gln Glu Gly Glu
50                      55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln His Thr Phe
                85                  90                  95

Glu Asp Ser Thr Lys Lys Cys Ala
            100

<210> SEQ ID NO 47
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Ala Ser Thr Lys Gly Pro Thr Val Lys Ile Trp Gln Ser Ser Cys Asp
1               5                   10                  15

Gly Gly Gly His Phe Pro Pro Thr Ile Gln Leu Leu Cys Leu Val Ser
            20                  25                  30

Gly Tyr Thr Pro Gly Thr Ile Gln Ile Thr Trp Leu Glu Asp Gly Gln
        35                  40                  45

Val Met Asp Val Asp Leu Ser Thr Ala Ser Thr Thr Gln Glu Gly Glu
50                      55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Thr Lys Lys Cys Ala
            100

<210> SEQ ID NO 48
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Arg Thr Val Ala Ala Pro Thr Val Lys Ile Leu Gln Ser Ser Cys Asp
1               5                   10                  15

Gly Gly Gly His Phe Pro Pro Thr Ile Gln Leu Gly Cys Leu Val Ser
            20                  25                  30

Gly Tyr Thr Pro Gly Thr Ile Gln Ile Thr Trp Leu Glu Asp Gly Gln
        35                  40                  45

Val Met Asp Val Asp Leu Ser Thr Ala Ser Thr Thr Gln Glu Gly Glu
    50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
```

```
                        85                  90                  95

Glu Asp Ser Thr Lys Lys Cys Ala
            100

<210> SEQ ID NO 49
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ala Ser Thr Lys Gly Pro Thr Val Lys Ile Leu Gln Ser Thr Cys Asp
1               5                   10                  15

Gly Gly Gly His Phe Pro Pro Thr Ile Gln Leu Leu Cys Leu Val Ser
            20                  25                  30

Gly Tyr Thr Pro Gly Thr Ile Gln Ile Thr Trp Leu Glu Asp Gly Gln
        35                  40                  45

Val Met Asp Val Asp Leu Ser Thr Ala Ser Thr Thr Gln Glu Gly Glu
    50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Thr Lys Lys Cys Ala
            100

<210> SEQ ID NO 50
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Arg Thr Val Ala Ala Pro Thr Val Lys Ile Leu Gln Ser Ser Cys Asp
1               5                   10                  15

Gly Gly Gly His Phe Pro Pro Thr Ile Gln Leu Leu Cys Leu Val Ser
            20                  25                  30

Gly Tyr Thr Pro Gly Thr Ile Gln Ile Thr Trp Leu Glu Asp Gly Gln
        35                  40                  45

Val Met Asp Val Asp Leu Ser Thr Ala Ser Thr Thr Gln Glu Gly Glu
    50                  55                  60

Leu Ala Ser Thr Gln Ser Glu Leu Thr Leu Ser Gln Lys His Trp Leu
65                  70                  75                  80

Ser Asp Arg Thr Tyr Thr Cys Gln Val Thr Tyr Gln Gly His Thr Phe
                85                  90                  95

Glu Asp Ser Ser Lys Lys Cys Ala
            100

<210> SEQ ID NO 51
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 51

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ile Met His Trp Val Arg Gln Ala Pro Gly Lys Gly Leu Glu Trp Val
        35                  40                  45

Ser Val Ile Ser Ser Ser Gly Asp Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Ala Gly Tyr Phe Asp Trp Leu Pro Phe Asp Tyr Trp
            100                 105                 110

Gly Gln Gly Thr Leu Val Thr Val Ser Ser Ala Ser Thr Lys Gly Pro
        115                 120                 125

Thr Val Lys Ile Leu Gln Ser Ile Cys Asp Gly Gly His Phe Pro
130                 135                 140

Pro Thr Ile Gln Leu Leu Cys Leu Val Ser Gly Tyr Thr Pro Gly Thr
145                 150                 155                 160

Ile Gln Ile Thr Trp Leu Glu Asp Gly Gln Val Met Asp Val Asp Leu
                165                 170                 175

Ser Thr Ala Ser Thr Thr Gln Glu Gly Glu Leu Ala Ser Thr Gln Ser
            180                 185                 190

Glu Leu Thr Leu Ser Gln Lys His Trp Leu Ser Asp Arg Thr Tyr Thr
        195                 200                 205

Cys Gln Val Thr Tyr Gln Gly His Thr Phe Glu Asp Ser Thr Lys Lys
    210                 215                 220

Cys Ala Ser Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Lys Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

```
Thr Pro Pro Val Leu Asp Ser Asp Gly Ser Phe Phe Leu Tyr Ser Ser
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
            450

<210> SEQ ID NO 52
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asp Ile Gln Met Thr Gln Ser Pro Ala Thr Leu Ser Leu Ser Pro Gly
1               5                   10                  15

Glu Thr Ala Thr Leu Ser Cys Arg Ala Ser Gln Ser Val Ser Tyr Tyr
            20                  25                  30

Leu Ala Trp Tyr Gln Gln Lys Pro Gly Gln Ala Pro Arg Leu Leu Ile
            35                  40                  45

Tyr Asp Thr Phe Asn Arg Ala Thr Gly Ile Pro Ala Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Trp Leu Thr Phe Gly Gly Gly Thr Lys Val Glu Ile Lys Arg Thr Val
            100                 105                 110

Ala Ala Pro Thr Val Lys Ile Leu Gln Ser Ser Cys Asp Gly Gly Gly
            115                 120                 125

His Phe Pro Pro Thr Ile Gln Leu Leu Cys Leu Val Ser Gly Tyr Thr
        130                 135                 140

Pro Gly Thr Ile Gln Ile Thr Trp Leu Glu Asp Gly Gln Val Met Asp
145                 150                 155                 160

Val Asp Leu Ser Thr Ala Ser Thr Thr Gln Glu Gly Glu Leu Ala Ser
                165                 170                 175

Thr Gln Ser Glu Leu Thr Leu Ser Gln Lys His Trp Leu Ser Asp Arg
            180                 185                 190

Thr Tyr Thr Cys Gln Val Thr Tyr Gln Gly His Thr Phe Glu Asp Ser
            195                 200                 205

Gly Lys Lys Cys Ala
        210

<210> SEQ ID NO 53
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Glu Val Gln Leu Leu Glu Ser Gly Gly Gly Leu Val Gln Pro Gly Gly
```

```
              1               5                  10                 15
        Ser Leu Arg Leu Ser Cys Ala Ala Ser Gly Phe Thr Phe Ser Ile Tyr
                        20                 25                 30

Arg Met Gln Trp Val Arg Gln Ala Pro Gly Lys Gly Leu Glu Trp Val
                        35                 40                 45

Ser Gly Ile Ser Pro Ser Gly Thr Thr Trp Tyr Ala Asp Ser Val
                        50                 55                 60

Lys Gly Arg Phe Thr Ile Ser Arg Asp Asn Ser Lys Asn Thr Leu Tyr
        65                  70                 75                 80

Leu Gln Met Asn Ser Leu Arg Ala Glu Asp Thr Ala Val Tyr Tyr Cys
                        85                 90                 95

Ala Arg Trp Ser Gly Ser Gly Tyr Ala Phe Asp Ile Trp Gly Gln
                        100                105                110

Gly Thr Met Val Thr Val Ser Ser Ala Ser Thr Lys Gly Pro Ser Val
                        115                120                125

Phe Pro Leu Ala Pro Ser Ser Lys Ser Thr Ser Gly Gly Thr Ala Ala
                        130                135                140

Leu Gly Cys Leu Val Lys Asp Tyr Phe Pro Glu Pro Val Thr Val Ser
        145                 150                155                160

Trp Asn Ser Gly Ala Leu Thr Ser Gly Val His Thr Phe Pro Ala Val
                        165                170                175

Leu Gln Ser Ser Gly Leu Tyr Ser Leu Ser Ser Val Val Thr Val Pro
                        180                185                190

Ser Ser Ser Leu Gly Thr Gln Thr Tyr Ile Cys Asn Val Asn His Lys
                        195                200                205

Pro Ser Asn Thr Lys Val Asp Lys Lys Val Glu Pro Lys Ser Cys Asp
                        210                215                220

Lys Thr His Thr Cys Pro Pro Cys Pro Ala Pro Glu Leu Leu Gly Gly
        225                 230                235                240

Pro Ser Val Phe Leu Phe Pro Pro Lys Pro Lys Asp Thr Leu Met Ile
                        245                250                255

Ser Arg Thr Pro Glu Val Thr Cys Val Val Val Asp Val Ser His Glu
                        260                265                270

Asp Pro Glu Val Lys Phe Asn Trp Tyr Val Asp Gly Val Glu Val His
                        275                280                285

Asn Ala Lys Thr Lys Pro Arg Glu Glu Gln Tyr Asn Ser Thr Tyr Arg
                        290                295                300

Val Val Ser Val Leu Thr Val Leu His Gln Asp Trp Leu Asn Gly Lys
        305                 310                315                320

Glu Tyr Lys Cys Lys Val Ser Asn Lys Ala Leu Pro Ala Pro Ile Glu
                        325                330                335

Lys Thr Ile Ser Lys Ala Lys Gly Gln Pro Arg Glu Pro Gln Val Tyr
                        340                345                350

Thr Leu Pro Pro Ser Arg Asp Glu Leu Thr Lys Asn Gln Val Ser Leu
                        355                360                365

Thr Cys Leu Val Ser Gly Phe Tyr Pro Ser Asp Ile Ala Val Glu Trp
                        370                375                380

Glu Ser Asn Gly Gln Pro Glu Asn Asn Tyr Lys Thr Thr Pro Pro Val
        385                 390                395                400

Leu Asp Ser Asp Gly Ser Phe Lys Leu Tyr Ser Lys Leu Thr Val Asp
                        405                410                415

Lys Ser Arg Trp Gln Gln Gly Asn Val Phe Ser Cys Ser Val Met His
                        420                425                430
```

-continued

Glu Ala Leu His Asn His Tyr Thr Gln Lys Ser Leu Ser Leu Ser Pro
                435                 440                 445
Gly

<210> SEQ ID NO 54
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Asp Ile Gln Met Thr Gln Ser Pro Leu Ser Leu Ser Ala Ser Val Gly
1               5                  10                  15

Asp Arg Val Thr Ile Thr Cys Gln Ala Ser Arg Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Thr Gly Val Pro Ser Arg Phe Gly Gly
    50                  55                  60

Ser Gly Ser Gly Thr Asp Phe Ser Phe Thr Ile Gly Ser Leu Gln Pro
65                  70                  75                  80

Glu Asp Glu Ala Thr Tyr Tyr Cys Gln Gln Phe Asp Ser Leu Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ser Gly Gly Gly
1

<210> SEQ ID NO 56
<211> LENGTH: 5
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Gly Gly Gly Ser
1               5

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Gly Gly Gly Gly
1               5

<210> SEQ ID NO 58
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Gly Gly Gly Gly Ser
1               5

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ser Gly Gly Gly Gly Gly
1               5

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Gly Gly Gly Gly Gly Ser
1               5

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

```
          Synthetic peptide"

<400> SEQUENCE: 61

Ser Gly Gly Gly Gly Gly Gly
1               5

<210> SEQ ID NO 62
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This region may encompass 0-4 'Gly Gly
      Gly Xaa Xaa' repeating units"
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 62

Gly Gly Gly Xaa Xaa Gly Gly Gly Xaa Xaa Gly Gly Gly Xaa Xaa Gly
1               5                   10                  15

Gly Gly Xaa Xaa Gly Gly Gly Gly Ser
            20                  25

<210> SEQ ID NO 63
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (6)..(25)
<223> OTHER INFORMATION: /note="This region may encompass 0-4 'Xaa Gly
      Gly Gly Ser' repeating units"
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
```

```
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 63

Gly Gly Gly Gly Ser Xaa Gly Gly Gly Ser Xaa Gly Gly Gly Ser Xaa
1               5                   10                  15

Gly Gly Gly Ser Xaa Gly Gly Gly Ser
            20                  25

<210> SEQ ID NO 64
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This region may encompass 0-4 'Gly Gly
      Gly Pro Ser' repeating units"

<400> SEQUENCE: 64

Gly Gly Gly Pro Ser Gly Gly Gly Pro Ser Gly Gly Gly Pro Ser Gly
1               5                   10                  15

Gly Gly Pro Ser Gly Gly Gly Gly Ser
            20                  25

<210> SEQ ID NO 65
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This region may encompass 0-4 'Gly Gly
      Gly Gly Gln' repeating units"

<400> SEQUENCE: 65

Gly Gly Gly Gly Gln Gly Gly Gly Gly Gln Gly Gly Gly Gly Gln Gly
1               5                   10                  15

Gly Gly Gly Gln Gly Gly Gly Gly Ser
            20                  25

<210> SEQ ID NO 66
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This region may encompass 0-4 'Gly Gly
      Gly Gly Ala' repeating units"

<400> SEQUENCE: 66

Gly Gly Gly Gly Ala Gly Gly Gly Gly Ala Gly Gly Gly Gly Ala Gly
1               5                   10                  15
```

Gly Gly Gly Ala Gly Gly Gly Gly Ser
            20                  25

<210> SEQ ID NO 67
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (6)..(25)
<223> OTHER INFORMATION: /note="This region may encompass 0-4 'Pro Gly
      Gly Gly Ser' repeating units"

<400> SEQUENCE: 67

Gly Gly Gly Gly Ser Pro Gly Gly Gly Ser Pro Gly Gly Gly Ser Pro
1               5                   10                  15

Gly Gly Gly Ser Pro Gly Gly Gly Ser
            20                  25

<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Gly Gly Gly Gly Ala Gly Gly Gly Gly Ala Gly Gly Gly Gly Ser
1               5                   10                  15

<210> SEQ ID NO 69
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Gly Gly Gly Gln Gly Gly Gly Gly Gln Gly Gly Gly Gly Ser
1               5                   10                  15

<210> SEQ ID NO 70
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gly Gly Gly Pro Ser Gly Gly Gly Pro Ser Gly Gly Gly Gly Ser
1               5                   10                  15

<210> SEQ ID NO 71
<211> LENGTH: 15
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 71

Gly Gly Gly Gly Ser Pro Gly Gly Gly Ser Pro Gly Gly Gly Ser
1               5                   10                  15

<210> SEQ ID NO 72
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 73
<211> LENGTH: 107
<212> TYPE: PRT
<213> ORGANISM: Homo sapiens

<400> SEQUENCE: 73

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 74
<211> LENGTH: 106
<212> TYPE: PRT
<213> ORGANISM: Homo sapiens

<400> SEQUENCE: 74

Gly Gln Pro Lys Ala Ala Pro Ser Val Thr Leu Phe Pro Pro Ser Ser
1               5                   10                  15
```

Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 75
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Glu Val Gln Leu Val Glu Ser Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Lys Val
            115                 120                 125

Ser Val Phe Val Pro Pro Arg Asp Gly Phe Phe Gly Asn Pro Arg Lys
130                 135                 140

Ser Lys Leu Ile Cys Gln Ala Thr Gly Phe Ser Pro Arg Gln Ile Gln
145                 150                 155                 160

Val Ser Trp Leu Arg Glu Gly Lys Gln Val Gly Ser Gly Val Thr Thr
            165                 170                 175

Asp Gln Val Gln Ala Glu Ala Lys Glu Ser Gly Pro Thr Thr Tyr Lys
            180                 185                 190

Val Thr Ser Thr Leu Thr Ile Lys Glu Ser Asp Trp Leu Gly Gln Ser
            195                 200                 205

Met Phe Thr Cys Arg Val Asp His Arg Gly Leu Thr Phe Gln Gln Gln
            210                 215                 220

Ala Ser Ser Met Cys His His His His His
225                 230                 235

<210> SEQ ID NO 76
<211> LENGTH: 216

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Lys Val Ser Val Phe Val Pro Pro Arg Asp Gly Phe Phe Gly Asn
        115                 120                 125

Pro Arg Lys Ser Lys Leu Ile Cys Gln Ala Thr Gly Phe Ser Pro Arg
    130                 135                 140

Gln Ile Gln Val Ser Trp Leu Arg Glu Gly Lys Gln Val Gly Ser Gly
145                 150                 155                 160

Val Thr Thr Asp Gln Val Gln Ala Glu Ala Lys Glu Ser Gly Pro Thr
                165                 170                 175

Thr Tyr Lys Val Thr Ser Thr Leu Thr Ile Lys Glu Ser Asp Trp Leu
            180                 185                 190

Gly Gln Ser Met Phe Thr Cys Arg Val Asp His Arg Gly Leu Thr Phe
        195                 200                 205

Gln Gln Gln Ala Ser Ser Met Cys
    210                 215

<210> SEQ ID NO 77
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ser Arg Asp Phe Thr
1               5

<210> SEQ ID NO 78
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gly Gln Pro Lys Ala Ala
```

<210> SEQ ID NO 79
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Thr Val
        115                 120                 125

Lys Ile Leu Gln Ser Ile Cys Asp Gly Gly His Phe Pro Pro Thr
    130                 135                 140

Ile Gln Leu Leu Cys Leu Val Ser Gly Tyr Thr Pro Gly Thr Ile Gln
145                 150                 155                 160

Ile Thr Trp Leu Glu Asp Gly Gln Val Met Asp Val Asp Leu Ser Thr
                165                 170                 175

Ala Ser Thr Thr Gln Glu Gly Glu Leu Ala Ser Thr Gln Ser Glu Leu
            180                 185                 190

Thr Leu Ser Gln Lys His Trp Leu Ser Asp Arg Thr Tyr Thr Cys Gln
        195                 200                 205

Val Thr Tyr Gln Gly His Thr Phe Glu Asp Ser Thr Lys Lys Cys Ala
    210                 215                 220

Ser Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

```
Val Tyr Thr Leu Pro Pro Ser Arg Asp Glu Leu Thr Lys Asn Gln Val
        355                 360                 365

Lys Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Leu Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 80
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Thr Val Lys Ile Leu Gln Ser Ser Cys Asp Gly Gly His Phe
        115                 120                 125

Pro Pro Thr Ile Gln Leu Leu Cys Leu Val Ser Gly Tyr Thr Pro Gly
    130                 135                 140

Thr Ile Gln Ile Thr Trp Leu Glu Asp Gly Gln Val Met Asp Val Asp
145                 150                 155                 160

Leu Ser Thr Ala Ser Thr Thr Gln Glu Gly Glu Leu Ala Ser Thr Gln
                165                 170                 175

Ser Glu Leu Thr Leu Ser Gln Lys His Trp Leu Ser Asp Arg Thr Tyr
            180                 185                 190

Thr Cys Gln Val Thr Tyr Gln Gly His Thr Phe Glu Asp Ser Gly Lys
        195                 200                 205

Lys Cys Ala
    210

<210> SEQ ID NO 81
<211> LENGTH: 214
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81
```

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 82
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82
```

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala

```
            85                  90                  95
Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Ser Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Ile Leu
385                 390                 395                 400

Asp Ser Asp Gly Ser Phe Lys Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 83
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ile Met His Trp Val Arg Gln Ala Pro Gly Lys Gly Leu Glu Trp Val
        35                  40                  45

Ser Val Ile Ser Ser Ser Gly Gly Asp Thr Ser Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Ala Gly Tyr Phe Asp Trp Leu Pro Phe Asp Tyr Trp
            100                 105                 110

Gly Gln Gly Thr Leu Val Thr Val Ser Ser Ala Ser Thr Lys Gly Pro
        115                 120                 125

Thr Val Lys Ile Leu Gln Ser Ile Cys Asp Gly Gly His Phe Pro
130                 135                 140

Pro Thr Ile Gln Leu Leu Cys Leu Val Ser Gly Tyr Thr Pro Gly Thr
145                 150                 155                 160

Ile Gln Ile Thr Trp Leu Glu Asp Gly Gln Val Met Asp Val Asp Leu
            165                 170                 175

Ser Thr Ala Ser Thr Thr Gln Glu Gly Glu Leu Ala Ser Thr Gln Ser
        180                 185                 190

Glu Leu Thr Leu Ser Gln Lys His Trp Leu Ser Asp Arg Thr Tyr Thr
            195                 200                 205

Cys Gln Val Thr Tyr Gln Gly His Thr Phe Glu Asp Ser Thr Lys Lys
210                 215                 220

Cys Ala Ser Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Ala Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Lys Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Ser
                405                 410                 415
```

```
Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 84
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Arg Met Gln Trp Val Arg Gln Ala Pro Gly Lys Gly Leu Glu Trp Val
        35                  40                  45

Ser Gly Ile Ser Pro Ser Gly Gly Thr Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Trp Ser Gly Gly Ser Gly Tyr Ala Phe Asp Ile Trp Gly Gln
        100                 105                 110

Gly Thr Met Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Ala Tyr Arg
    290                 295                 300

Val Val Ser Val Leu Thr Val Leu His Gln Asp Trp Leu Asn Gly Lys
```

```
            305                 310                 315                 320
        Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Ser Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Lys Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly

<210> SEQ ID NO 85
<211> LENGTH: 679
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Asn Ile Lys Asp Thr
                        20                  25                  30

Tyr Ile His Trp Val Arg Gln Ala Pro Gly Lys Gly Leu Glu Trp Val
                        35                  40                  45

Ala Arg Ile Tyr Pro Thr Asn Gly Tyr Thr Arg Tyr Ala Asp Ser Val
                        50                  55                  60

Lys Gly Arg Phe Thr Ile Ser Ala Asp Thr Ser Lys Asn Thr Ala Tyr
        65                  70                  75                  80

Leu Gln Met Asn Ser Leu Arg Ala Glu Asp Thr Ala Val Tyr Tyr Cys
                        85                  90                  95

Ser Arg Trp Gly Gly Asp Gly Phe Tyr Ala Met Asp Tyr Trp Gly Gln
                        100                 105                 110

Gly Thr Leu Val Thr Val Ser Ser Ala Ser Thr Lys Gly Pro Ser Val
                        115                 120                 125

Phe Pro Leu Ala Pro Ser Ser Lys Ser Thr Ser Gly Gly Thr Ala Ala
                        130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                        195                 200                 205
```

```
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Ser Gly Gly Gly Ser Glu Val Gln Leu Leu Glu Ser Gly Gly
450                 455                 460
Gly Leu Val Gln Pro Gly Gly Ser Leu Arg Leu Ser Cys Ala Ala Ser
465                 470                 475                 480
Gly Phe Thr Phe Ser Ile Tyr Arg Met Gln Trp Val Arg Gln Ala Pro
                485                 490                 495
Gly Lys Gly Leu Glu Trp Val Ser Gly Ile Ser Pro Ser Gly Gly Thr
            500                 505                 510
Thr Trp Tyr Ala Asp Ser Val Lys Gly Arg Phe Thr Ile Ser Arg Asp
        515                 520                 525
Asn Ser Lys Asn Thr Leu Tyr Leu Gln Met Asn Ser Leu Arg Ala Glu
530                 535                 540
Asp Thr Ala Val Tyr Tyr Cys Ala Arg Trp Ser Gly Gly Ser Gly Tyr
545                 550                 555                 560
Ala Phe Asp Ile Trp Gly Gln Gly Thr Met Val Thr Val Ser Ser Ala
                565                 570                 575
Ser Thr Lys Gly Pro Thr Val Lys Ile Leu Gln Ser Ile Cys Asp Gly
            580                 585                 590
Gly Gly His Phe Pro Pro Thr Ile Gln Leu Leu Cys Leu Val Ser Gly
        595                 600                 605
Tyr Thr Pro Gly Thr Ile Gln Ile Thr Trp Leu Glu Asp Gly Gln Val
610                 615                 620
Met Asp Val Asp Leu Ser Thr Ala Ser Thr Thr Gln Glu Gly Glu Leu
```

```
                625                 630                 635                 640
Ala Ser Thr Gln Ser Glu Leu Thr Leu Ser Gln Lys His Trp Leu Ser
                    645                 650                 655

Asp Arg Thr Tyr Thr Cys Gln Val Thr Tyr Gln Gly His Thr Phe Glu
            660                 665                 670

Asp Ser Thr Lys Lys Cys Ala
        675

<210> SEQ ID NO 86
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Asp Ile Gln Met Thr Gln Ser Pro Leu Ser Leu Ser Ala Ser Val Gly
1               5                   10                  15

Asp Arg Val Thr Ile Thr Cys Gln Ala Ser Arg Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Thr Gly Val Pro Ser Arg Phe Gly Gly
    50                  55                  60

Ser Gly Ser Gly Thr Asp Phe Ser Phe Thr Ile Gly Ser Leu Gln Pro
65                  70                  75                  80

Glu Asp Glu Ala Thr Tyr Tyr Cys Gln Gln Phe Asp Ser Leu Pro His
                85                  90                  95

Thr Phe Gly Gln Gly Thr Lys Leu Glu Ile Lys Arg Thr Val Ala Ala
            100                 105                 110

Pro Thr Val Lys Ile Leu Gln Ser Ser Cys Asp Gly Gly Gly His Phe
        115                 120                 125

Pro Pro Thr Ile Gln Leu Leu Cys Leu Val Ser Gly Tyr Thr Pro Gly
    130                 135                 140

Thr Ile Gln Ile Thr Trp Leu Glu Asp Gly Gln Val Met Asp Val Asp
145                 150                 155                 160

Leu Ser Thr Ala Ser Thr Thr Gln Glu Gly Glu Leu Ala Ser Thr Gln
                165                 170                 175

Ser Glu Leu Thr Leu Ser Gln Lys His Trp Leu Ser Asp Arg Thr Tyr
            180                 185                 190

Thr Cys Gln Val Thr Tyr Gln Gly His Thr Phe Glu Asp Ser Gly Lys
        195                 200                 205

Lys Cys Ala
    210

<210> SEQ ID NO 87
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 88
<211> LENGTH: 679
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Arg Met Gln Trp Val Arg Gln Ala Pro Gly Lys Gly Leu Glu Trp Val
        35                  40                  45

Ser Gly Ile Ser Pro Ser Gly Gly Thr Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ser Gly Gly Ser Gly Tyr Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225             230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305             310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Ser Gly Gly Gly Gly Ser Glu Val Gln Leu Val Glu Ser Gly Gly
    450                 455                 460

Gly Leu Val Gln Pro Gly Gly Ser Leu Arg Leu Ser Cys Ala Ala Ser
465                 470                 475                 480

Gly Phe Asn Ile Lys Asp Thr Tyr Ile His Trp Val Arg Gln Ala Pro
            485                 490                 495

Gly Lys Gly Leu Glu Trp Val Ala Arg Ile Tyr Pro Thr Asn Gly Tyr
            500                 505                 510

Thr Arg Tyr Ala Asp Ser Val Lys Gly Arg Phe Thr Ile Ser Ala Asp
            515                 520                 525

Thr Ser Lys Asn Thr Ala Tyr Leu Gln Met Asn Ser Leu Arg Ala Glu
            530                 535                 540

Asp Thr Ala Val Tyr Tyr Cys Ser Arg Trp Gly Gly Asp Gly Phe Tyr
545                 550                 555                 560

Ala Met Asp Tyr Trp Gly Gln Gly Thr Leu Val Thr Val Ser Ser Ala
```

```
            565                 570                 575
Ser Thr Lys Gly Pro Thr Val Lys Ile Leu Gln Ser Ile Cys Asp Gly
            580                 585                 590

Gly Gly His Phe Pro Pro Thr Ile Gln Leu Leu Cys Leu Val Ser Gly
        595                 600                 605

Tyr Thr Pro Gly Thr Ile Gln Ile Thr Trp Leu Glu Asp Gly Gln Val
    610                 615                 620

Met Asp Val Asp Leu Ser Thr Ala Ser Thr Thr Gln Glu Gly Glu Leu
625                 630                 635                 640

Ala Ser Thr Gln Ser Glu Leu Thr Leu Ser Gln Lys His Trp Leu Ser
                645                 650                 655

Asp Arg Thr Tyr Thr Cys Gln Val Thr Tyr Gln Gly His Thr Phe Glu
            660                 665                 670

Asp Ser Thr Lys Lys Cys Ala
            675

<210> SEQ ID NO 89
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Asp Glu Asp Glu
1

<210> SEQ ID NO 90
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 90

His His His His His His
1               5

<210> SEQ ID NO 91
<211> LENGTH: 113
<212> TYPE: PRT
<213> ORGANISM: Homo sapiens

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
                100                 105                 110
Pro

<210> SEQ ID NO 92
<211> LENGTH: 106
<212> TYPE: PRT
<213> ORGANISM: Pan sp.

<400> SEQUENCE: 92

Val Cys Ser Arg Asp Phe Thr Pro Thr Val Lys Val Leu Gln Ser Ser
1               5                   10                  15

Cys Asp Gly Gly Gly His Phe Pro Pro Thr Ile Gln Leu Leu Cys Leu
                20                  25                  30

Val Ser Gly Tyr Thr Pro Gly Thr Ile Asn Ile Thr Trp Leu Glu Asp
            35                  40                  45

Gly Gln Val Met Asp Val Asp Leu Ser Thr Ala Ser Ala Thr Gln Glu
50                  55                  60

Gly Glu Leu Ala Ser Thr Gln Ser Glu Leu Thr Leu Ser Gln Lys His
65                  70                  75                  80

Trp Leu Ser Asp Arg Thr Tyr Thr Cys Gln Val Thr Tyr Gln Gly Gly
                85                  90                  95

Thr Phe Glu Asp Ser Thr Lys Lys Cys Ala
                100                 105

<210> SEQ ID NO 93
<211> LENGTH: 102
<212> TYPE: PRT
<213> ORGANISM: Mus sp.

<400> SEQUENCE: 93

Asn Ile Thr Glu Pro Thr Leu Glu Leu Leu His Ser Ser Cys Asp Pro
1               5                   10                  15

Asn Ala Phe His Ser Thr Ile Gln Leu Tyr Cys Phe Ile Tyr Gly His
                20                  25                  30

Ile Leu Asn Asp Val Ser Val Ser Trp Leu Met Asp Asp Arg Glu Ile
            35                  40                  45

Thr Asp Thr Leu Ala Gln Thr Val Leu Ile Lys Glu Glu Gly Lys Leu
50                  55                  60

Ala Ser Thr Cys Ser Lys Leu Asn Ile Thr Glu Gln Gln Trp Met Ser
65                  70                  75                  80

Glu Ser Thr Phe Thr Cys Lys Val Thr Ser Gln Gly Val Asp Tyr Leu
                85                  90                  95

Ala His Thr Arg Arg Cys
            100

<210> SEQ ID NO 94
<211> LENGTH: 103
<212> TYPE: PRT
<213> ORGANISM: Rattus sp.

<400> SEQUENCE: 94

Asn Ile Thr Lys Pro Thr Val Asp Leu Leu His Ser Ser Cys Asp Pro
1               5                   10                  15

Asn Ala Phe His Ser Thr Ile Gln Leu Tyr Cys Phe Val Tyr Gly His
                20                  25                  30

Ile Gln Asn Asp Val Ser Ile His Trp Leu Met Asp Asp Arg Lys Ile
            35                  40                  45
```

```
Tyr Glu Thr His Ala Gln Asn Val Leu Ile Lys Glu Glu Gly Lys Leu
        50                   55                 60

Ala Ser Thr Tyr Ser Arg Leu Asn Ile Thr Gln Gln Gln Trp Met Ser
 65                  70                   75                   80

Glu Ser Thr Phe Thr Cys Lys Val Thr Ser Gln Gly Gly Asn Tyr Trp
                 85                  90                  95

Ala His Thr Arg Arg Cys Ser
                100
```

<210> SEQ ID NO 95
<211> LENGTH: 107
<212> TYPE: PRT
<213> ORGANISM: Oryctolagus sp.

<400> SEQUENCE: 95

```
Ala Cys Ser Val Ser Phe Thr Pro Pro Ala Val Arg Leu Phe His Ser
 1               5                  10                  15

Ser Cys Asp Pro Arg Glu Asn Asp Thr Tyr Thr Val Gln Leu Leu Cys
                20                  25                  30

Leu Ile Ser Gly Tyr Thr Pro Gly Asp Ile Glu Val Thr Trp Leu Val
             35                  40                  45

Asp Gly Gln Lys Asp Pro Asn Met Phe Ser Ile Thr Ala Gln Pro Arg
 50                  55                  60

Gln Glu Gly Lys Leu Ala Ser Thr His Ser Glu Leu Asn Ile Thr Gln
 65                  70                  75                   80

Gly Glu Trp Ala Ser Lys Arg Thr Tyr Thr Cys Arg Val Ala Tyr Gln
                 85                  90                  95

Gly Glu Leu Phe Glu Ala His Ala Arg Glu Cys
                100                 105
```

<210> SEQ ID NO 96
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

```
Lys Leu Glu Leu Lys Arg Thr Val Ala Ala Pro Ser Val Phe Ile Phe
 1               5                  10                  15
```

<210> SEQ ID NO 97
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

```
Lys Leu Glu Leu Lys Arg Thr Val Ala Ala Pro Thr Val Lys Ile Leu
 1               5                  10                  15
```

<210> SEQ ID NO 98
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Lys Leu Glu Leu Lys Gly Gln Pro Lys Ala Ala Pro Thr Val Lys Ile
1               5                   10                  15

Leu

<210> SEQ ID NO 99
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Lys Leu Glu Leu Lys Ser Arg Asp Phe Thr Pro Thr Val Lys Ile Leu
1               5                   10                  15

<210> SEQ ID NO 100
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Lys Leu Glu Leu Lys Gly Gly Gly Gly Ser Pro Thr Val Lys Ile Leu
1               5                   10                  15

<210> SEQ ID NO 101
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Lys Leu Glu Leu Lys Gly Gly Gly Gly Ser Gly Pro Thr Val Lys Ile
1               5                   10                  15

Leu

<210> SEQ ID NO 102
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Arg Thr Val Ala Ala Pro
1               5

<210> SEQ ID NO 103
<211> LENGTH: 6
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 103

Ser Arg Asp Phe Thr Pro
1               5

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Gln Pro Lys Ala Ala Pro
1               5

<210> SEQ ID NO 105
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gly Gly Gly Gly Ser Pro
1               5

<210> SEQ ID NO 106
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Gly Gly Ser Gly Pro
1               5
```

BISPECIFIC ANTIBODY PLATFORM

CROSS-REFERENCE TO RELATED APPLICATION

This application is the National Stage of International Application No. PCT/US2016/066865, filed on Dec. 15, 2016, which claims the benefit of priority to U.S. Provisional Appl. No. 62/269,664, filed Dec. 18, 2015, the contents of both of which are incorporated by reference in their entirety herein.

BACKGROUND

There is increasing interest in the use of bispecific antibodies as biologics drugs due, in large part, to the potential of achieving novel mechanisms of action that cannot be achieved with a combination of two conventional monospecific antibodies. Efficient methods for generating bispecific antibodies are therefore sought after. Initial attempts to produce bispecific antibodies as biologics drugs involved chemical conjugation of monospecific antibodies and fusion of mAb-expressing cells, but low efficiency and the necessity of purification from abundant side products are disadvantages of these strategies. Advanced methods in protein engineering and molecular biology have enabled the generation of a variety of new bispecific antibody formats. However, altered biochemical/biophysical properties, serum half-life, or stability of these engineered bispecific antibody formats can be unfavorable. Thus, an efficient platform for the generation of bispecific antibodies that might overcome some of these problems would be useful.

SUMMARY

This application relates to an antibody platform technology that can convert any two antibodies that bind to different epitopes into a bispecific antibody. This platform technology involves, in part, Fc regions that are engineered in their CH3 domains by lysine repositioning to drive heterodimerization of the two heavy chains of the bispecific antibody. In addition, this technology involves a modification of one of the two Fab arms of the bispecific antibody so as to prevent mispairing of light chains in the bispecific antibody. Specifically, the CH1 and CL domains of one of the Fab arms of the bispecific antibody are substituted with an IgE CH2 domain or an IgM CH2 domain. In some instances, the CH1 and CL domains of one of the Fab arms of the bispecific antibody are substituted with a fragment of an IgE CH2 domain (or an IgM CH2 domain), wherein the fragment can still dimerize with the IgE CH2 domain (or the IgM CH2 domain).

In one aspect, this disclosure provides an antibody or antigen-binding fragment thereof that comprises a first heavy chain variable domain (first VH) and a first light chain variable domain (first VL), wherein the first VH and the first VL pair to form a first variable region that binds specifically to a first epitope of a first antigen. The first VH is either directly linked or linked via a linker to a first polypeptide comprising an amino acid sequence that is at least 80% identical to amino acids 9-107 of the amino acid sequence of the CH2 domain of human immunoglobulin E (IgE) (SEQ ID NO:1). The first VL is either directly linked or linked via a linker to a second polypeptide comprising an amino acid sequence that is at least 80% identical to amino acids 9-107 of the amino acid sequence of the CH2 domain of human IgE (SEQ ID NO:1). The first polypeptide and the second polypeptide pair to form a dimer.

In certain embodiments of this aspect, the first polypeptide and/or the second polypeptide is directly linked to an Fc domain. In certain instances, the Fc domain comprises a CH2 and CH3 domain of an IgG1 antibody. In certain instances, the Fc domain comprises a CH2 and CH3 domain of an IgG4 antibody. In certain instances, the Fc domain comprises a CH2 of an IgG4 antibody and a CH3 domain of an IgG1 antibody. In some of all of these embodiments, the Fc domain comprises a hinge region of an IgG4 antibody (e.g., IgG4P—i.e., IgG4 hinge region with the S228P mutation). In some embodiments, the first polypeptide and/or the second polypeptide comprise the amino acid sequence set forth in SEQ ID NO:1. In some embodiments, the first polypeptide and/or the second polypeptide comprise an amino acid sequence that is at least 90% identical to amino acids 9-107 of the amino acid sequence set forth in SEQ ID NO:1. In certain embodiments, the first polypeptide and/or the second polypeptide comprise amino acids 9-107 of the amino acid sequence set forth in SEQ ID NO:1. In some embodiments, the first polypeptide comprises an amino acid sequence that is at least 80% identical to the amino acid sequence set forth in SEQ ID NO:5. In a specific embodiment, the first polypeptide comprises the amino acid sequence set forth in SEQ ID NO:5. In some embodiments, the second polypeptide comprises an amino acid sequence that is at least 80% identical to the amino acid sequence set forth in SEQ ID NO:6. In a specific embodiment, the second polypeptide comprises an amino acid sequence that is identical to the amino acid sequence set forth in SEQ ID NO:6. In some embodiments, the first polypeptide and/or the second polypeptide differ from the amino acid sequence set forth in amino acids 9-107 of SEQ ID NO:1 at twelve or fewer amino acid residues. In some embodiments, the first polypeptide and/or the second polypeptide contain an amino acid other than cysteine at at least one of the two cysteine residues of SEQ ID NO:1 that do not form an intrachain disulfide bond. In certain embodiments, the first polypeptide and the second polypeptide each contain a mutation of the N-linked glycosylation site in the IgE CH2 domain or fragment thereof such that the N-linked glycosylation site is not glycosylated (e.g., the asparagine and/or threonine residue is substituted with another amino acid). In certain embodiments, the first polypeptide or the second polypeptide contain a mutation of the N-linked glycosylation site in the IgE CH2 domain or fragment thereof such that the N-linked glycosylation site is not glycosylated. In certain embodiments, the antibody or antigen-binding fragment thereof comprises a second heavy chain variable domain (second VH) and a second light chain variable domain (second VL), wherein the second VH and the second VL pair to form a second variable region that binds specifically to a second epitope of the first antigen or to a second antigen. In certain embodiments, the second VH is either (i) directly linked or (ii) linked via a linker to a CH1 domain and the second VL is either (i) directly linked or (ii) linked via a linker to a CL domain. In certain embodiments, the disclosure provides a polynucleotide or polynucleotides encoding the antibody or antigen-binding fragment described above. In some embodiments, expression vectors are provided comprising the polynucleotide or polynucleotides described above. In other embodiments, host cells comprising the polynucleotide or polynucleotides or the expression vectors are provided. In yet other embodiments, provided are methods of making the antibody or antigen-binding fragment described above comprising culturing the host cells described above under conditions that result in the expression of the antibody or antigen-binding fragment described above and isolating the antibody or antigen-binding fragment from the cell culture. In certain embodiments, the isolated antibody or antigen-binding fragment is formulated as a sterile composition for administration to a human subject in need thereof.

In a second aspect, the disclosure provides an antibody or antigen-binding fragment thereof comprising a first VH and a first VL, wherein the first VH and the first VL pair to form a first variable region that binds specifically to a first epitope of a first antigen. The first VH is either (i) directly linked or (ii) linked via a linker to a first polypeptide comprising an amino acid sequence that is at least 80% identical to amino acids 7-112 of the amino acid sequence of the CH2 domain of human immunoglobulin M (IgM) (SEQ ID NO:2). The first VL is either (i) directly linked or (ii) linked via a linker to a second polypeptide comprising an amino acid sequence that is at least 80% identical to amino acids 7-112 of the amino acid sequence of the CH2 domain of human IgM (SEQ ID NO:2). The first polypeptide and the second polypeptide pair to form a dimer.

In certain embodiments of this aspect, the first polypeptide and/or the second polypeptide is directly linked to an Fc domain. In certain instances, the Fc domain comprises a CH2 and CH3 domain of an IgG1 antibody. In certain instances, the Fc domain comprises a CH2 and CH3 domain of an IgG4 antibody. In certain instances, the Fc domain comprises a CH2 of an IgG4 antibody and a CH3 domain of an IgG1 antibody. In some of all of these embodiments, the Fc domain comprises a hinge region of an IgG4 antibody (e.g., IgG4P—i.e., IgG4 hinge region with the S228P mutation). In some embodiments, the first polypeptide and/or the second polypeptide comprise the amino acid sequence set forth in SEQ ID NO:2. In some embodiments, the first polypeptide and/or the second polypeptide comprise an amino acid sequence that is at least 90% identical to amino acids 7-112 of the amino acid sequence set forth in SEQ ID NO:2. In certain embodiments, the first polypeptide and/or the second polypeptide comprise amino acids 7-112 of the amino acid sequence set forth in SEQ ID NO:2. In some embodiments, the first polypeptide and/or the second polypeptide differ from the amino acid sequence set forth in amino acids 7-112 of SEQ ID NO:2 at twelve or fewer amino acid residues. In some embodiments, the first polypeptide and/or the second polypeptide contain an amino acid other than cysteine at the cysteine residue of SEQ ID NO:2 that does not form an intrachain disulfide bond. In certain embodiments, the first polypeptide and the second polypeptide each contain a mutation of the N-linked glycosylation site in the IgM CH2 domain or fragment thereof such that the N-linked glycosylation site is not glycosylated (e.g., the asparagine and/or serine residue is substituted with another amino acid). In certain embodiments, the first polypeptide or the second polypeptide contain a mutation of the N-linked glycosylation site in the IgM CH2 domain or fragment thereof such that the N-linked glycosylation site is not glycosylated. In certain embodiments, the antibody or antigen-binding fragment thereof comprises a second heavy chain variable domain (second VH) and a second light chain variable domain (second VL), wherein the second VH and the second VL pair to form a second variable region that binds specifically to a second epitope of the first antigen or to a second antigen. In certain embodiments, the second VH is either (i) directly linked or (ii) linked via a linker to a CH1 domain and the second VL is either (i) directly linked or (ii) linked via a linker to a CL domain. In certain embodiments, the disclosure provides a polynucleotide or polynucleotides encoding the antibody or antigen-binding fragment described above. In some embodiments, expression vectors are provided comprising the polynucleotide or polynucleotides described above. In other embodiments, host cells comprising the polynucleotide or polynucleotides or the expression vectors are provided. In yet other embodiments, provided are methods of making the antibody or antigen-binding fragment described above comprising culturing the host cells described above under conditions that result in the expression of the antibody or antigen-binding fragment described above and isolating the antibody or antigen-binding fragment from the cell culture. In certain embodiments, the isolated antibody or antigen-binding fragment is formulated as a sterile composition for administration to a human subject in need thereof.

In another aspect, the disclosure provides a bispecific antibody that comprises a first fragment antigen-binding (first Fab) comprising a first VH and a first VL, wherein the first VH and the first VL pair to form a first variable region. The first VH is either (i) directly linked or (ii) linked via a linker to a first polypeptide comprising an amino acid sequence that is at least 80% identical to amino acids 9-107 of the amino acid sequence of the CH2 domain of human immunoglobulin E (IgE) (SEQ ID NO:1). The first VL is either (i) directly linked or (ii) linked via a linker to a second polypeptide comprising an amino acid sequence that is at least 80% identical to amino acids 9-107 of the amino acid sequence of the CH2 domain of human IgE (SEQ ID NO:1). The bispecific antibody further comprises a second Fab comprising a second VH and a second VL, wherein the second VH and the second VL pair to form a second variable region, and wherein the second VH is either (i) directly linked or (ii) linked via a linker to a CH1 domain and the second VL is either (i) directly linked or (ii) linked via a linker to a CL domain. The first Fab and the second Fab specifically bind to different antigens or to different epitopes of the same antigen and the first Fab is connected to the second Fab.

In some embodiments of this aspect, the first Fab is connected to the second Fab by a linker. In certain embodiments, the first Fab is connected to the second Fab by a heterologous polypeptide. In some embodiments, the heterologous polypeptide is human serum albumin. In some embodiments, the heterologous polypeptide is an XTEN (e.g., AE144, AE288). In some embodiments, the first Fab is connected to the second Fab by polyethylene glycol (PEG). In certain embodiments, the first polypeptide and/or the second polypeptide each comprise the amino acid sequence set forth in SEQ ID NO:1. In some embodiments, the first polypeptide and/or the second polypeptide comprise an amino acid sequence that is at least 90% identical to amino acids 9-107 of the amino acid sequence set forth in SEQ ID NO:1. In certain embodiments, the first polypeptide and/or the second polypeptide comprise amino acids 9-107 of the amino acid sequence set forth in SEQ ID NO:1. In some embodiments, the first polypeptide comprises an amino acid sequence that is at least 80% identical to the amino acid sequence set forth in SEQ ID NO:5. In some embodiments, the first polypeptide comprises the amino acid sequence set forth in SEQ ID NO:5. In certain embodiments, the second polypeptide comprises an amino acid sequence that is at least 80% identical to the amino acid sequence set forth in SEQ ID NO:6. In some embodiments, the second polypeptide comprises the amino acid sequence set forth in SEQ ID NO:6. In certain embodiments, the first polypeptide and/or the second polypeptide differ from the amino acid sequence set forth in amino acids 9-107 of SEQ ID NO:1 at twelve amino acid residues or fewer. In other embodiments, the first polypeptide and/or the second polypeptide contain an amino acid other than cysteine at at least one of the two cysteine residues of SEQ ID NO:1 that can form an interchain disulfide bond. In certain embodiments, the first polypeptide and/or the second polypeptide contain a mutation of the N-linked glycosylation site in the IgE CH2 domain or fragment thereof such that the N-linked glycosylation site is not glycosylated. For example, the asparagine and/or threonine of the IgE CH2 domain N-linked glycosylation site may be substituted with another amino acid to prevent glycosylation of this motif. In certain embodiments, the disclosure provides a polynucleotide or polynucleotides encoding the bispecific antibody described above. In some embodiments, expression vectors are provided comprising the bispecific antibody described above. In other embodiments, host cells comprising the bispecific antibody or the expression vectors are provided. In yet other embodiments, provided are methods of making the bispecific antibody comprising culturing the host cells described above under conditions that result in the expression of the bispecific antibody and isolating the bispecific antibody from the cell culture. In certain embodiments, the isolated bispecific antibody is formulated as a sterile composition for administration to a human subject in need thereof.

In another aspect, this disclosure provides a bispecific antibody comprising a first fragment antigen-binding (first Fab) comprising a first VH and a first VL, wherein the first VH and the first VL pair to form a first variable region. The first VH is either (i) directly linked or (ii) linked via a linker to a first polypeptide comprising an amino acid sequence that is at least 80% identical to amino acids 7-112 of the amino acid sequence of the CH2 domain of human immunoglobulin M (IgM) (SEQ ID NO:2). The first VL is either (i) directly linked or (ii) linked via a linker to a second polypeptide comprising an amino acid sequence that is at least 80% identical to amino acids 7-112 of the amino acid sequence of the CH2 domain of human IgM (SEQ ID NO:2). The bispecific antibody further comprises a second Fab comprising a second VH and a second VL. The second VH and the second VL pair to form a second variable region, and wherein the second VH is either (i) directly linked or (ii) linked via a linker to a CH1 domain and the second VL is either (i) directly linked or (ii) linked via a linker to a CL domain. The first Fab and the second Fab specifically bind to different antigens or to different epitopes of the same antigen. The first Fab is connected to the second Fab.

In some embodiments of this aspect, the first Fab is connected to the second Fab by a linker. In certain embodiments, the first Fab is connected to the second Fab by a heterologous polypeptide. In some embodiments, the heterologous polypeptide is human serum albumin. In some embodiments, the heterologous polypeptide is an XTEN (e.g., AE144, AE288). In some embodiments, the first Fab is connected to the second Fab by polyethylene glycol (PEG). In certain embodiments, the first polypeptide and/or the second polypeptide each comprise the amino acid sequence set forth in SEQ ID NO:2. In some embodiments, the first polypeptide and/or the second polypeptide comprise an amino acid sequence that is at least 90% identical to amino acids 7-112 of the amino acid sequence set forth in SEQ ID NO:2. In certain embodiments, the first polypeptide and/or the second polypeptide comprise amino acids 7-112 of the amino acid sequence set forth in SEQ ID NO:2. In certain embodiments, the first polypeptide and/or the second polypeptide differ from the amino acid sequence set forth in amino acids 7-112 of SEQ ID NO:2 at twelve amino acid residues or fewer. In other embodiments, the first polypeptide and/or the second polypeptide contain an amino acid other than cysteine at the cysteine residue of SEQ ID NO:2 that can form an interchain disulfide bond. In certain embodiments, the first polypeptide and/or the second polypeptide contain a mutation of the N-linked glycosylation site in the IgM CH2 domain or fragment thereof such that the N-linked glycosylation site is not glycosylated. For example, the asparagine and/or serine of the IgM CH2 domain N-linked glycosylation site may be substituted with another amino acid to prevent glycosylation of this motif. In certain embodiments, the disclosure provides a polynucleotide or polynucleotides encoding the bispecific antibody described above. In some embodiments, expression vectors are provided comprising the bispecific antibody described above. In other embodiments, host cells comprising the bispecific antibody or the expression vectors are provided. In yet other embodiments, provided are methods of making the bispecific antibody comprising culturing the host cells described above under conditions that result in the expression of the bispecific antibody and isolating the bispecific antibody from the cell culture. In certain embodiments, the isolated bispecific antibody is formulated as a sterile composition for administration to a human subject in need thereof.

In another aspect, this disclosure provides a tetravalent bispecific antibody that comprises a whole IgG antibody that specifically binds to a first epitope of a first antigen, the whole IgG antibody comprising a first CH3 domain and a second CH3 domain; and a first Fab and a second Fab. The first Fab comprises a first heavy chain variable domain (first VH) and a first light chain variable domain (first VL), wherein the first VH and the first VL pair to form a first variable region that binds specifically to a second epitope of the first antigen or to a second antigen. The second Fab comprises a second heavy chain variable domain (second VH) and a second light chain variable domain (second VL), wherein the second VH and the second VL pair to form a second variable region that binds specifically to the same epitope as the first Fab. The first VH is either (i) directly linked or (ii) linked via a linker to a first polypeptide comprising an amino acid sequence that is at least 80% identical to amino acids 9-107 of the amino acid sequence of the CH2 domain of human immunoglobulin E (IgE) (SEQ ID NO:1). The first VL is either (i) directly linked or (ii) linked via a linker to a second polypeptide comprising an amino acid sequence that is at least 80% identical to amino acids 9-107 of the amino acid sequence of the CH2 domain of human IgE (SEQ ID NO:1). The second VH is either (i) directly linked or (ii) linked via a linker to a third polypeptide comprising an amino acid sequence that is at least 80% identical to amino acids 9-107 of the amino acid sequence of the CH2 domain of human IgE (SEQ ID NO:1). The second VL is either (i) directly linked or (ii) linked via a linker to a fourth polypeptide comprising an amino acid sequence that is at least 80% identical to amino acids 9-107 of the amino acid sequence of the CH2 domain of human IgE (SEQ ID NO:1). The first Fab is connected to the C-terminus of the first CH3 domain of the whole IgG antibody and the second Fab is connected to the C-terminus of the second CH3 domain of the whole IgG antibody.

In some embodiments of this aspect, the first Fab is connected to the C-terminus of the first CH3 domain of the whole antibody through a first linker and the second Fab is connected to the C-terminus of the second CH3 domain of the whole antibody through a second linker. In certain embodiments, the first linker links the C-terminus of the first CH3 domain of the whole antibody and the N-terminus of the first VH. In certain embodiments, the first linker links the C-terminus of the first CH3 domain of the whole antibody and the N-terminus of the first VL. In certain embodiments, the first linker links the C-terminus of the first CH3 domain of the whole antibody and the N-terminus of the first polypeptide. In certain embodiments, the first linker links the C-terminus of the first CH3 domain of the whole antibody and the N-terminus of the second polypeptide. In certain embodiments, the second linker links the C-terminus of the first CH3 domain of the whole antibody and the N-terminus of the second VH. In certain embodiments, the second linker links the C-terminus of the first CH3 domain of the whole antibody and the N-terminus of the second VL. In certain embodiments, the second linker links the C-terminus of the first CH3 domain of the whole antibody and the N-terminus of the third polypeptide. In certain embodiments, the second linker links the C-terminus of the first CH3 domain of the whole antibody and the N-terminus of the fourth polypeptide. In certain embodiments, the first and second linkers are peptide linkers. In some embodiments, the first polypeptide, the second polypeptide, the third polypeptide, and/or the fourth polypeptide comprise the amino acid sequence set forth in SEQ ID NO:1. In certain embodiments, the first polypeptide, the second polypeptide, the third polypeptide, and/or the fourth polypeptide comprise an amino acid sequence that is at least 90% identical to amino acids 9-107 of the amino acid sequence set forth in SEQ ID NO:1. In some embodiments, the first polypeptide, the second polypeptide, the third polypeptide, and/or the fourth polypeptide comprise amino acids 9-107 of the amino acid sequence set forth in SEQ ID NO:1. In some embodiments, the first polypeptide and the third polypeptide each comprise an amino acid sequence that is at least 80% identical to the amino acid sequence set forth in SEQ ID NO:5. In certain embodiments, the first polypeptide and the third polypeptide each comprise the amino acid sequence set forth in SEQ ID NO:5. In certain embodiments, the second polypeptide and the fourth polypeptide each comprise an amino acid sequence that is at least 80% identical to the amino acid sequence set forth in SEQ ID NO:6. In some embodiments, the second polypeptide and the fourth polypeptide each comprise the amino acid sequence set forth in SEQ ID NO:6. In certain embodiments, the first polypeptide, the second polypeptide, the third polypeptide and/or the fourth polypeptide differ from the amino acid sequence set forth in amino acids 9-107 of SEQ ID NO:1 at least twelve amino acid residues. In certain embodiments, the disclosure provides a polynucleotide or polynucleotides encoding the bispecific antibody described above. In some embodiments, expression vectors are provided comprising the bispecific antibody described above. In other embodiments, host cells comprising the bispecific antibody or the expression vectors are provided. In yet other embodiments, provided are methods of making the bispecific antibody comprising culturing the host cells described above under conditions that result in the expression of the bispecific antibody and isolating the bispecific antibody from the cell culture. In certain embodiments, the isolated bispecific antibody is formulated as a sterile composition for administration to a human subject in need thereof.

In another aspect, this disclosure provides a tetravalent bispecific antibody comprising a whole IgG antibody that specifically binds to a first epitope of a first antigen, the whole IgG antibody comprising a first CH3 domain and a second CH3 domain; and a first Fab and a second Fab. The first Fab comprises a first heavy chain variable domain (first VH) and a first light chain variable domain (first VL), wherein the first VH and the first VL pair to form a first variable region that binds specifically to a second epitope of the first antigen or to a second antigen. The second Fab comprises a second heavy chain variable domain (second VH) and a second light chain variable domain (second VL), wherein the second VH and the second VL pair to form a second variable region that binds specifically to the same epitope as the first Fab. The first VH is either (i) directly linked or (ii) linked via a linker to a first polypeptide comprising an amino acid sequence that is at least 80% identical to amino acids 7-112 of the amino acid sequence of the CH2 domain of human immunoglobulin M (IgM) (SEQ ID NO:2). The first VL is either (i) directly linked or (ii) linked via a linker to a second polypeptide comprising an amino acid sequence that is at least 80% identical to amino acids 7-112 of the amino acid sequence of the CH2 domain of human IgM (SEQ ID NO:2). The second VH is either (i) directly linked or (ii) linked via a linker to a third polypeptide comprising an amino acid sequence that is at least 80% identical to amino acids 7-112 of the amino acid sequence of the CH2 domain of human IgM (SEQ ID NO:2). The second VL is either (i) directly linked or (ii) linked via a linker to a fourth polypeptide comprising an amino acid sequence that is at least 80% identical to amino acids 7-112 of the amino acid sequence of the CH2 domain of human IgM (SEQ ID NO:2). The first Fab is connected to the C-terminus of the first CH3 domain of the whole IgG antibody and the second Fab is connected to the C-terminus of the second CH3 domain of the whole IgG antibody.

In some embodiments of this aspect, the first Fab is connected to the C-terminus of the first CH3 domain of the whole antibody through a first linker and the second Fab is connected to the C-terminus of the second CH3 domain of the whole antibody through a second linker. In certain embodiments, the first linker links the C-terminus of the first CH3 domain of the whole antibody and the N-terminus of the first VH. In certain embodiments, the first linker links the C-terminus of the first CH3 domain of the whole antibody and the N-terminus of the first VL. In certain embodiments, the first linker links the C-terminus of the first CH3 domain of the whole antibody and the N-terminus of the first polypeptide. In certain embodiments, the first linker links the C-terminus of the first CH3 domain of the whole antibody and the N-terminus of the second polypeptide. In certain embodiments, the second linker links the C-terminus of the first CH3 domain of the whole antibody and the N-terminus of the second VH. In certain embodiments, the second linker links the C-terminus of the first CH3 domain of the whole antibody and the N-terminus of the second VL. In certain embodiments, the second linker links the C-terminus of the first CH3 domain of the whole antibody and the N-terminus of the third polypeptide. In certain embodiments, the second linker links the C-terminus of the first CH3 domain of the whole antibody and the N-terminus of the fourth polypeptide. In certain embodiments, the first and second linkers are peptide linkers. In some embodiments, the first polypeptide, the second polypeptide, the third polypeptide, and/or the fourth polypeptide comprise the amino acid sequence set forth in SEQ ID NO:2. In certain embodiments, the first polypeptide, the second polypeptide, the third polypeptide, and/or the fourth polypeptide comprise an amino acid sequence that is at least 90% identical to amino acids 7-112 of the amino acid sequence set forth in SEQ ID NO:2. In some embodiments, the first polypeptide, the second polypeptide, the third polypeptide, and/or the fourth polypeptide comprise amino acids 7-112 of the amino acid sequence set forth in SEQ ID NO:2. In certain embodiments, the first polypeptide, the second polypeptide, the third polypeptide and/or the fourth polypeptide differ from the amino acid sequence set forth in amino acids 7-112 of SEQ ID NO:2 at at least twelve amino acid residues. In certain embodiments, the disclosure provides a polynucleotide or polynucleotides encoding the bispecific antibody described above. In some embodiments, expression vectors are provided comprising the bispecific antibody described above. In other embodiments, host cells comprising the bispecific antibody or the expression vectors are provided. In yet other embodiments, provided are methods of making the bispecific antibody comprising culturing the host cells described above under conditions that result in the expression of the bispecific antibody and isolating the bispecific antibody from the cell culture. In certain embodiments, the isolated bispecific antibody is formulated as a sterile composition for administration to a human subject in need thereof.

In another aspect, the disclosure relates to a tetravalent bispecific antibody comprising a first Fab and a second Fab, wherein the first Fab comprises a first heavy chain variable domain (first VH) and a first light chain variable domain (first VL), wherein the first VH and the first VL pair to form a first variable region that binds specifically to a first epitope of a first antigen, and wherein the second Fab comprises a second heavy chain variable domain (second VH) and a second light chain variable domain (second VL), wherein the second VH and the second VL pair to form a second variable region that binds specifically to the first epitope of the first antigen. The tetravalent bispecific antibody also comprises a whole antibody comprising a first heavy chain comprising a first IgG CH2 domain and a first IgG CH3 domain, a second heavy chain comprising a second IgG CH2 domain and a second IgG CH3 domain, a first light chain, and a second light chain, wherein the antibody comprises a third VH and third VL and a fourth VH and a fourth VL, wherein the third VH and the third VL pair to form a third variable region that binds specifically to an epitope of a second antigen, and wherein the fourth VH and the fourth VL pair to form a fourth variable region that binds specifically to the same epitope of the second antigen. The third VH is either (i) directly linked or (ii) linked via a linker to a first polypeptide comprising an amino acid sequence that is at least 80% identical to amino acids 9-107 of the amino acid sequence of the CH2 domain of human immunoglobulin E (IgE) (SEQ ID NO:1). The third VL is either (i) directly linked or (ii) linked via a linker to a second polypeptide comprising an amino acid sequence that is at least 80% identical to amino acids 9-107 of the amino acid sequence of the CH2 domain of human IgE (SEQ ID NO:1). The fourth VH is either (i) directly linked or (ii) linked via a linker to a third polypeptide comprising an amino acid sequence that is at least 80% identical to amino acids 9-107 of the amino acid sequence of the CH2 domain of human IgE (SEQ ID NO:1). The fourth VL is either (i) directly linked or (ii) linked via a linker to a fourth polypeptide comprising an amino acid sequence that is at least 80% identical to amino acids 9-107 of the amino acid sequence of the CH2 domain of human IgE (SEQ ID NO:1). The first polypeptide is connected to the N-terminus of the first IgG CH2 domain and the third polypeptide is connected to the N-terminus of the second IgG CH2 domain. The first Fab is connected to the C-terminus of the first IgG CH3 domain and the second Fab is connected to the C-terminus of the second IgG CH3 domain.

In some embodiments of this aspect, the first Fab is connected to the C-terminus of the first CH3 domain of the whole antibody through a first linker and the second Fab is connected to the C-terminus of the second CH3 domain of the whole antibody through a second linker. In certain embodiments, the first and second linkers are peptide linkers. In some embodiments, the first polypeptide, the second polypeptide, the third polypeptide, and/or the fourth polypeptide comprise the amino acid sequence set forth in SEQ ID NO:1. In certain embodiments, the first polypeptide, the second polypeptide, the third polypeptide, and/or the fourth polypeptide comprise an amino acid sequence that is at least 90% identical to amino acids 9-107 of the amino acid sequence set forth in SEQ ID NO:1. In some embodiments, the first polypeptide, the second polypeptide, the third polypeptide, and/or the fourth polypeptide comprise amino acids 9-107 of the amino acid sequence set forth in SEQ ID NO:1. In some embodiments, the first polypeptide and the third polypeptide each comprise an amino acid sequence that is at least 80% identical to the amino acid sequence set forth in SEQ ID NO:5. In certain embodiments, the first polypeptide and the third polypeptide each comprise the amino acid sequence set forth in SEQ ID NO:5. In certain embodiments, the second polypeptide and the fourth polypeptide each comprise an amino acid sequence that is at least 80% identical to the amino acid sequence set forth in SEQ ID NO:6. In some embodiments, the second polypeptide and the fourth polypeptide each comprise the amino acid sequence set forth in SEQ ID NO:6. In certain embodiments, the first polypeptide, the second polypeptide, the third polypeptide and/or the fourth polypeptide differ from the amino acid sequence set forth in amino acids 9-107 of SEQ ID NO:1 at at least twelve amino acid residues. In certain embodiments, the disclosure provides a polynucleotide or polynucleotides encoding the bispecific antibody described above. In some embodiments, expression vectors are provided comprising the bispecific antibody described above. In other embodiments, host cells comprising the bispecific antibody or the expression vectors are provided. In yet other embodiments, provided are methods of making the bispecific antibody comprising culturing the host cells described above under conditions that result in the expression of the bispecific antibody and isolating the bispecific antibody from the cell culture. In certain embodiments, the isolated bispecific antibody is formulated as a sterile composition for administration to a human subject in need thereof.

In another aspect, the disclosure relates to a tetravalent bispecific antibody comprising a first Fab and a second Fab, wherein the first Fab comprises a first heavy chain variable domain (first VH) and a first light chain variable domain (first VL), wherein the first VH and the first VL pair to form a first variable region that binds specifically to a first epitope of a first antigen, and wherein the second Fab comprises a second heavy chain variable domain (second VH) and a second light chain variable domain (second VL), wherein the second VH and the second VL pair to form a second variable region that binds specifically to the first epitope of the first antigen. The tetravalent bispecific antibody also comprises a whole antibody comprising a first heavy chain comprising a first IgG CH2 domain and a first IgG CH3 domain, a second heavy chain comprising a second IgG CH2 domain and a second IgG CH3 domain, a first light chain, and a second light chain, wherein the antibody comprises a third VH and third VL and a fourth VH and a fourth VL, wherein the third VH and the third VL pair to form a third variable region that binds specifically to an epitope of a second antigen, and wherein the fourth VH and the fourth VL pair to form a fourth variable region that binds specifically to the same epitope of the second antigen. The third VH is either (i) directly linked or (ii) linked via a linker to a first polypeptide comprising an amino acid sequence that is at least 80% identical to amino acids 7-112 of the amino acid sequence of the CH2 domain of human immunoglobulin M (IgM) (SEQ ID NO:2). The third VL is either (i) directly linked or (ii) linked via a linker to a second polypeptide comprising an amino acid sequence that is at least 80% identical to amino acids 7-112 of the amino acid sequence of the CH2 domain of human IgM (SEQ ID NO:2). The fourth VH is either (i) directly linked or (ii) linked via a linker to a third polypeptide comprising an amino acid sequence that is at least 80% identical to amino acids 7-112 of the amino acid sequence of the CH2 domain of human IgM (SEQ ID NO:2). The fourth VL is either (i) directly linked or (ii) linked via a linker to a fourth polypeptide comprising an amino acid sequence that is at least 80% identical to amino acids 7-112 of the amino acid sequence of the CH2 domain of human IgM (SEQ ID NO:2). The first polypeptide is connected to the N-terminus of the first IgG CH2 domain and the third polypeptide is connected to the N-terminus of the second IgG CH2 domain. The first Fab is connected to the C-terminus of the first IgG CH3 domain and the second Fab is connected to the C-terminus of the second IgG CH3 domain.

In some embodiments of this aspect, the first Fab is connected to the C-terminus of the first CH3 domain of the whole antibody through a first linker and the second Fab is connected to the C-terminus of the second CH3 domain of the whole antibody through a second linker. In certain embodiments, the first and second linkers are peptide linkers. In some embodiments, the first polypeptide, the second polypeptide, the third polypeptide, and/or the fourth polypeptide comprise the amino acid sequence set forth in SEQ ID NO:2. In certain embodiments, the first polypeptide, the second polypeptide, the third polypeptide, and/or the fourth polypeptide comprise an amino acid sequence that is at least 90% identical to amino acids 7-112 of the amino acid sequence set forth in SEQ ID NO:2. In some embodiments, the first polypeptide, the second polypeptide, the third polypeptide, and/or the fourth polypeptide comprise amino acids 7-112 of the amino acid sequence set forth in SEQ ID NO:2. In certain embodiments, the first polypeptide, the second polypeptide, the third polypeptide and/or the fourth polypeptide differ from the amino acid sequence set forth in amino acids 7-112 of SEQ ID NO:2 at at least twelve amino acid residues. In certain embodiments, the disclosure provides a polynucleotide or polynucleotides encoding the bispecific antibody described above. In some embodiments, expression vectors are provided comprising the bispecific antibody described above. In other embodiments, host cells comprising the bispecific antibody or the expression vectors are provided. In yet other embodiments, provided are methods of making the bispecific antibody comprising culturing the host cells described above under conditions that result in the expression of the bispecific antibody and isolating the bispecific antibody from the cell culture. In certain embodiments, the isolated bispecific antibody is formulated as a sterile composition for administration to a human subject in need thereof.

In yet another aspect, the disclosure provides a heterodimerization module comprising a first IgG1 CH3 domain having an amino acid sequence that is at least 80% identical to the sequence set forth in SEQ ID NO:11, wherein the amino acids at positions 364 and 370 are lysines and the amino acid at position 409 is a serine; and a second IgG1 CH3 domain having an amino acid sequence that is at least 80% identical to the sequence set forth in SEQ ID NO:11, wherein the amino acid at position 370 is a serine and the amino acids at positions 405 and 409 are lysines. The amino acid positions are based on the EU numbering system. The first IgG1 CH3 domain and the second IgG1 CH3 pair to form a heterodimer.

In certain embodiments of this aspect, the heterodimerization module includes a first IgG1 CH2 domain and a second IgG1 CH2 domain, wherein the first IgG1 CH2 domain is either (i) directly linked or (ii) linked via a linker to the N-terminus of the first IgG1 CH3 domain and the second IgG1 CH2 domain is either (i) directly linked or (ii) linked via a linker to the N-terminus of the second IgG1 CH3 domain.

In some embodiments, the heterodimerization module includes a first Fab comprising two polypeptide chains, wherein the C-terminus of one of the two polypeptide chains of the Fab is linked to the N-terminus of a first hinge region, and wherein the first hinge region is linked to the N-terminus of the first IgG1 CH2 domain.

In other embodiments, the heterodimerization module comprises a linker that links the C-terminus of the first IgG1 CH3 domain to the N-terminus of a second hinge region that is linked to the N-terminus of the second IgG1 CH2 domain. In certain embodiments, the heterodimerization module includes a second Fab linked via a second hinge region to the N-terminus of the second IgG1 CH2 domain.

In certain embodiments, the heterodimerization module comprises a VH domain, a CH1 domain, a VL domain, and a CL domain. The C-terminus of the VH domain is linked to the N-terminus of the CH1 domain, the C-terminus of the CH1 domain is linked to the N-terminus of a first hinge region, and the C-terminus of the first hinge region is linked to the N-terminus of the first IgG1 CH2 domain that is directly linked to the first IgG1 CH3 domain. The C-terminus of the VL domain is linked to the N-terminus of the CL domain, the C-terminus of the CL domain is linked to the N-terminus of a second hinge region, and the C-terminus of the second hinge region is linked to the N-terminus of the second IgG1 CH2 domain that is directly linked to the second IgG1 CH3 domain. The VH domain and the VL domain pair to form a variable region that binds specifically to an antigen.

In certain embodiments, the heterodimerization module comprises a first VH and a first VL and a second VH and a second VL. The first VH and the first VL pair to form a first variable region that binds specifically to a first antigen. The second VH and the second VL pair to form a second variable region that binds specifically to a different epitope of the first antigen or to a second antigen. In some instances, the amino acid sequence of the first VL is identical to the amino acid sequence of the second VL.

In certain embodiments, the heterodimerization module comprises a first IgG4 CH2 domain and a second IgG4 CH2 domain, wherein the first IgG4 CH2 domain is either (i) directly linked or (ii) linked via a linker to the N-terminus of the first IgG1 CH3 domain and the second IgG4 CH2 domain is either (i) directly linked or (ii) linked via a linker to the N-terminus of the second IgG1 CH3 domain. In some instances, the heterodimerization module includes a first Fab comprising two polypeptide chains, wherein the C-terminus of one of the two polypeptide chains of the Fab is linked to the N-terminus of a first IgG4 hinge region, and wherein the first IgG4 hinge region is linked to the N-terminus of the first IgG4 CH2 domain. In some instances, the first IgG4 hinge region comprises the S228P mutation (EU numbering). In some instances, the heterodimerization module includes a linker that links the C-terminus of the first IgG1 CH3 domain to the N-terminus of a second IgG4 hinge region that is linked to the N-terminus of the second IgG4 CH2 domain. In certain instances, the second IgG4 hinge region comprises the S228P mutation (EU numbering). In some instances, the heterodimerization module includes a second Fab linked via a second IgG4 hinge region to the N-terminus of the second IgG4 CH2 domain. In certain instances, the second IgG4 hinge region comprises the S228P mutation (EU numbering).

In some embodiments, the heterodimerization module comprises a VH domain, a CH1 domain, a VL domain, and a CL domain. The C-terminus of the VH domain is linked to the N-terminus of the CH1 domain, the C-terminus of the CH1 domain is linked to the N-terminus of a first IgG4 hinge region, and the C-terminus of the first IgG4 hinge region is linked to the N-terminus of the first IgG4 CH2 domain that is directly linked to the first IgG1 CH3 domain. The C-terminus of the VL domain is linked to the N-terminus of the CL domain, the C-terminus of the CL domain is linked to the N-terminus of a second IgG4 hinge region, and the C-terminus of the second IgG4 hinge region is linked to the N-terminus of the second IgG4 CH2 domain that is directly linked to the second IgG1 CH3 domain. The VH domain and the VL domain pair to form a variable region that binds specifically to an antigen. In some instances, the first IgG4 hinge region and the second IgG4 hinge region each comprise the S228P mutation (EU numbering).

In some embodiments, the heterodimerization module comprises a first VH and a first VL and a second VH and a second VL. The first VH and the first VL pair to form a first variable region that binds specifically to a first antigen. The second VH and the second VL pair to form a second variable region that binds specifically to a different epitope of the first antigen or to a second antigen. In some instances, the amino acid sequence of the first VL is identical to the amino acid sequence of the second VL.

In certain embodiments, the disclosure features a polynucleotide or polynucleotides that encode the above-described heterodimerization module. In some instances, an expression vector or expression vectors comprising the polynucleotide or polynucleotides are featured. In other instances, host cells are provided that comprise the polynucleotide or polynucleotides or expression vector or vectors. In some instances, methods of producing the heterodimerization module are encompassed. The methods involve culturing the host cells under conditions that result in expression of the heterodimerization module and isolation thereof.

In another aspect, the disclosure relates to a heterodimerization module comprising a first IgG1 CH3 domain having an amino acid sequence that is at least 80% identical to the sequence set forth in SEQ ID NO:11, wherein the amino acids at positions 364 and 370 are lysines and the amino acid at position 409 is a leucine; and a second IgG1 CH3 domain having an amino acid sequence that is at least 80% identical to the sequence set forth in SEQ ID NO:11, wherein the amino acid at position 370 is a serine, the amino acid at position 397 is an isoleucine, and the amino acids at positions 405 and 409 are lysines. The amino acid positions are based on the EU numbering system. The first IgG1 CH3 domain and the second IgG1 CH3 pair to form a heterodimer.

In certain embodiments of this aspect, the heterodimerization module includes a first IgG1 CH2 domain and a second IgG1 CH2 domain, wherein the first IgG1 CH2 domain is either (i) directly linked or (ii) linked via a linker to the N-terminus of the first IgG1 CH3 domain and the second IgG1 CH2 domain is either (i) directly linked or (ii) linked via a linker to the N-terminus of the second IgG1 CH3 domain.

In some embodiments, the heterodimerization module includes a first Fab comprising two polypeptide chains, wherein the C-terminus of one of the two polypeptide chains of the Fab is linked to the N-terminus of a first hinge region, and wherein the first hinge region is linked to the N-terminus of the first IgG1 CH2 domain.

In other embodiments, the heterodimerization module comprises a linker that links the C-terminus of the first IgG1 CH3 domain to the N-terminus of a second hinge region that is linked to the N-terminus of the second IgG1 CH2 domain. In certain embodiments, the heterodimerization module includes a second Fab linked via a second hinge region to the N-terminus of the second IgG1 CH2 domain.

In certain embodiments, the heterodimerization module comprises a VH domain, a CH1 domain, a VL domain, and a CL domain. The C-terminus of the VH domain is linked to the N-terminus of the CH1 domain, the C-terminus of the CH1 domain is linked to the N-terminus of a first hinge region, and the C-terminus of the first hinge region is linked to the N-terminus of the first IgG1 CH2 domain that is directly linked to the first IgG1 CH3 domain. The C-terminus of the VL domain is linked to the N-terminus of the CL domain, the C-terminus of the CL domain is linked to the N-terminus of a second hinge region, and the C-terminus of the second hinge region is linked to the N-terminus of the second IgG1 CH2 domain that is directly linked to the second IgG1 CH3 domain. The VH domain and the VL domain pair to form a variable region that binds specifically to an antigen.

In certain embodiments, the heterodimerization module comprises a first VH and a first VL and a second VH and a second VL. The first VH and the first VL pair to form a first variable region that binds specifically to a first antigen. The second VH and the second VL pair to form a second variable region that binds specifically to a different epitope of the first antigen or to a second antigen. In some instances, the amino acid sequence of the first VL is identical to the amino acid sequence of the second VL.

In certain embodiments, the heterodimerization module comprises a first IgG4 CH2 domain and a second IgG4 CH2 domain, wherein the first IgG4 CH2 domain is either (i) directly linked or (ii) linked via a linker to the N-terminus of the first IgG1 CH3 domain and the second IgG4 CH2 domain is either (i) directly linked or (ii) linked via a linker to the N-terminus of the second IgG1 CH3 domain. In some instances, the heterodimerization module includes a first Fab comprising two polypeptide chains, wherein the C-terminus of one of the two polypeptide chains of the Fab is linked to the N-terminus of a first IgG4 hinge region, and wherein the first IgG4 hinge region is linked to the N-terminus of the first IgG4 CH2 domain. In some instances, the first IgG4 hinge region comprises the S228P mutation (EU numbering). In some instances, the heterodimerization module includes a linker that links the C-terminus of the first IgG1 CH3 domain to the N-terminus of a second IgG4 hinge region that is linked to the N-terminus of the second IgG4 CH2 domain. In certain instances, the second IgG4 hinge region comprises the S228P mutation (EU numbering). In some instances, the heterodimerization module includes a second Fab linked via a second IgG4 hinge region to the N-terminus of the second IgG4 CH2 domain. In certain instances, the second IgG4 hinge region comprises the S228P mutation (EU numbering).

In some embodiments, the heterodimerization module comprises a VH domain, a CH1 domain, a VL domain, and a CL domain. The C-terminus of the VH domain is linked to the N-terminus of the CH1 domain, the C-terminus of the CH1 domain is linked to the N-terminus of a first IgG4 hinge region, and the C-terminus of the first IgG4 hinge region is linked to the N-terminus of the first IgG4 CH2 domain that is directly linked to the first IgG1 CH3 domain. The C-terminus of the VL domain is linked to the N-terminus of the CL domain, the C-terminus of the CL domain is linked to the N-terminus of a second IgG4 hinge region, and the C-terminus of the second IgG4 hinge region is linked to the N-terminus of the second IgG4 CH2 domain that is directly linked to the second IgG1 CH3 domain. The VH domain and the VL domain pair to form a variable region that binds specifically to an antigen. In some instances, the first IgG4 hinge region and the second IgG4 hinge region each comprise the S228P mutation (EU numbering).

In some embodiments, the heterodimerization module comprises a first VH and a first VL and a second VH and a second VL. The first VH and the first VL pair to form a first variable region that binds specifically to a first antigen. The second VH and the second VL pair to form a second variable region that binds specifically to a different epitope of the first antigen or to a second antigen. In some instances, the amino acid sequence of the first VL is identical to the amino acid sequence of the second VL.

In certain embodiments, the disclosure features a polynucleotide or polynucleotides that encode the above-described heterodimerization module. In some instances, an expression vector or expression vectors comprising the polynucleotide or polynucleotides are featured. In other instances, host cells are provided that comprise the polynucleotide or polynucleotides or expression vector or vectors. In some instances, methods of producing the heterodimerization module are encompassed. The methods involve culturing the host cells under conditions that result in expression of the heterodimerization module and isolation thereof.

In another aspect, the disclosure provides a bispecific antibody that includes a first VH and a first VL, wherein the first VH and the first VL pair to form a first variable region that binds specifically to a first epitope of a first antigen. The first VH is either (i) directly linked or (ii) linked via a linker to a first polypeptide comprising an amino acid sequence that is at least 80% identical to amino acids 9-107 of the amino acid sequence of the CH2 domain of human immunoglobulin E (IgE) (SEQ ID NO:1). The first VL is either (i) directly linked or (ii) linked via a linker to a second polypeptide comprising an amino acid sequence that is at least 80% identical to amino acids 9-107 of the amino acid sequence of the CH2 domain of human IgE (SEQ ID NO:1). The first polypeptide and the second polypeptide pair to form a dimer. The bispecific antibody also includes a second VH and a second VL, wherein the second VH and the second VL pair to form a second variable region that binds specifically to a second epitope of the first antigen or to a second antigen. The second VH is either (i) directly linked or (ii) linked via a linker to a CH1 domain. The second VL is either (i) directly linked or (ii) linked via a linker to a CL domain. The CH1 domain and the CL domain pair to form a dimer. The bispecific antibody also includes a heterodimerization module comprising a first IgG1 CH3 domain having an amino acid sequence that is at least 80% identical to the sequence set forth in SEQ ID NO:11, wherein the amino acids at positions 364 and 370 are lysines and the amino acid at position 409 is a serine. The heterodimerization module also includes a second IgG1 CH3 domain having an amino acid sequence that is at least 80% identical to the sequence set forth in SEQ ID NO:11, wherein the amino acid at position 370 is a serine and the amino acids at positions 405 and 409 are lysines. The amino acid positions above are all based on the EU numbering system. (It is important to note that the IgE CH2 domain can be part of the polypeptide comprising the first IgG1 CH3 domain or the second IgG1 CH3 domain.)

In another aspect, the disclosure provides a bispecific antibody that includes a first VH and a first VL, wherein the first VH and the first VL pair to form a first variable region that binds specifically to a first epitope of a first antigen. The first VH is either (i) directly linked or (ii) linked via a linker to a first polypeptide comprising an amino acid sequence that is at least 80% identical to amino acids 9-107 of the amino acid sequence of the CH2 domain of human immunoglobulin E (IgE) (SEQ ID NO:1). The first VL is either (i) directly linked or (ii) linked via a linker to a second polypeptide comprising an amino acid sequence that is at least 80% identical to amino acids 9-107 of the amino acid sequence of the CH2 domain of human IgE (SEQ ID NO:1). The first polypeptide and the second polypeptide pair to form a dimer. The bispecific antibody also includes a second VH and a second VL, wherein the second VH and the second VL pair to form a second variable region that binds specifically to a second epitope of the first antigen or to a second antigen. The second VH is either (i) directly linked or (ii) linked via a linker to a CH1 domain. The second VL is either (i) directly linked or (ii) linked via a linker to a CL domain. The CH1 domain and the CL domain pair to form a dimer. The bispecific antibody also includes a heterodimerization module comprising a first IgG1 CH3 domain having an amino acid sequence that is at least 80% identical to the sequence set forth in SEQ ID NO:11, wherein the amino acids at positions 364 and 370 are lysines and the amino acid at position 409 is a leucine. The heterodimerization module also includes a second IgG1 CH3 domain having an amino acid sequence that is at least 80% identical to the sequence set forth in SEQ ID NO:11, wherein the amino acid at position 370 is a serine, the amino acid at position 397 is an isoleucine, and the amino acids at positions 405 and 409 are lysines. The amino acid positions above are all based on the EU numbering system. (It is important to note that the IgE CH2 domain can be part of the polypeptide comprising the first IgG1 CH3 domain or the second IgG1 CH3 domain.)

In some embodiments of the above two aspects, the bispecific antibody includes two IgG1 CH2 domains. In some embodiments of the above two aspects, the bispecific antibody includes two IgG4 CH2 domains. In some embodiments, a single polypeptide chain comprises the first VH, the first polypeptide, and the first IgG1 CH3 domain. In some embodiments, a single polypeptide chain comprises the first VH, the first polypeptide, and the second IgG1 CH3 domain. In other embodiments, a single polypeptide chain comprises the first VL, the second polypeptide, and the first IgG1 CH3 domain. In yet other embodiments, a single polypeptide chain comprises the first VL, the second polypeptide, and the second IgG1 CH3 domain. In some embodiments, a second single polypeptide chain comprises the second VH, the CH1 domain, and the second IgG1 CH3 domain. In some embodiments, a second single polypeptide chain comprises the second VH, the CH1 domain, and the first IgG1 CH3 domain. In some embodiments, a second single polypeptide chain comprises the second VL, the CL domain, and the second IgG1 CH3 domain. In some embodiments, a second single polypeptide chain comprises the second VL, the CL domain, and the first IgG1 CH3 domain. In some embodiments, the first polypeptide and/or the second polypeptide comprise the amino acid sequence set forth in SEQ ID NO:1. In certain embodiments, the first polypeptide and/or the second polypeptide comprise an amino acid sequence that is at least 90% identical to amino acids 9-107 of the amino acid sequence set forth in SEQ ID NO:1. In other embodiments, the first polypeptide and/or the second polypeptide comprise amino acids 9-107 of the amino acid sequence set forth in SEQ ID NO:1. In other embodiments, the first polypeptide comprises an amino acid sequence that is at least 80% identical to the amino acid sequence set forth in SEQ ID NO:5. In other embodiments, the first polypeptide comprises the amino acid sequence set forth in SEQ ID NO:5. In certain embodiments, the second polypeptide comprises an amino acid sequence that is at least 80% identical to the amino acid sequence set forth in SEQ ID NO:6. In some embodiments, the second polypeptide comprises the amino acid sequence set forth in SEQ ID NO:6. In certain embodiments, the first polypeptide and/or the second polypeptide differ from the amino acid sequence set forth in SEQ ID NO:1 at at least twelve amino acid residues. In some embodiments, the first polypeptide and the second polypeptide each contain an amino acid other than cysteine at at least one of the two cysteine residues of SEQ ID NO:1 that do not form intrachain disulfide bond. In certain embodiments, the first polypeptide and the second polypeptide have a mutation or mutations at the N-linked glycosylation site such that the first polypeptide and the second polypeptide are not glycosylated at the N-linked glycosylation site. In other embodiments, the first polypeptide or the second polypeptide have a mutation or mutations at the N-linked glycosylation site such that the first polypeptide and the second polypeptide are not glycosylated at the N-linked glycosylation site. These mutations can be of the asparagine or the threonine or serine of the N-linked glycosylation site to other amino acid(s).

In another aspect, the disclosure provides a bispecific antibody comprising a first VH and a first VL, wherein the first VH and the first VL pair to form a first variable region that binds specifically to a first epitope of a first antigen. The first VH is either (i) directly linked or (ii) linked via a linker to a first polypeptide comprising an amino acid sequence that is at least 80% identical to amino acids 7-112 of the amino acid sequence of the CH2 domain of human immunoglobulin M (IgM) (SEQ ID NO:2). The first VL is either (i) directly linked or (ii) linked via a linker to a second polypeptide comprising an amino acid sequence that is at least 80% identical to amino acids 7-112 of the amino acid sequence of the CH2 domain of human IgM (SEQ ID NO:2). The first polypeptide and the second polypeptide pair to form a dimer. The bispecific antibody also comprises a second VH and a second VL, wherein the second VH and the second VL pair to form a second variable region that binds specifically to a second epitope of the first antigen or to a second antigen. The second VH is either (i) directly linked or (ii) linked via a linker to a CH1 domain. The second VL is either (i) directly linked or (ii) linked via a linker to a CL domain, and wherein the CH1 domain and the CL domain pair to form a dimer. The bispecific antibody also comprises a heterodimerization module that includes a first IgG1 CH3 domain having an amino acid sequence that is at least 80% identical to the sequence set forth in SEQ ID NO:11, wherein the amino acids at positions 364 and 370 are lysines and the amino acid at position 409 is a serine; and a second IgG1 CH3 domain having an amino acid sequence that is at least 80% identical to the sequence set forth in SEQ ID NO:11, wherein the amino acid at position 370 is a serine and the amino acids at positions 405 and 409 are lysines. The amino acid positions above are based on the EU numbering system.

In another aspect, the disclosure relates to a bispecific antibody comprising a first VH and a first VL, wherein the first VH and the first VL pair to form a first variable region that binds specifically to a first epitope of a first antigen. The first VH is either (i) directly linked or (ii) linked via a linker to a first polypeptide comprising an amino acid sequence that is at least 80% identical to amino acids 7-112 of the amino acid sequence of the CH2 domain of human immunoglobulin M (IgM) (SEQ ID NO:2). The first VL is either (i) directly linked or (ii) linked via a linker to a second polypeptide comprising an amino acid sequence that is at least 80% identical to amino acids 7-112 of the amino acid sequence of the CH2 domain of human IgM (SEQ ID NO:2). The first polypeptide and the second polypeptide pair to form a dimer. The bispecific antibody also comprises a second VH and a second VL, wherein the second VH and the second VL pair to form a second variable region that binds specifically to a second epitope of the first antigen or to a second antigen. The second VH is either (i) directly linked or (ii) linked via a linker to a CH1 domain. The second VL is either (i) directly linked or (ii) linked via a linker to a CL domain, and wherein the CH1 domain and the CL domain pair to form a dimer. The bispecific antibody also comprises a heterodimerization module that includes a first IgG1 CH3 domain having an amino acid sequence that is at least 80% identical to the sequence set forth in SEQ ID NO:11, wherein the amino acids at positions 364 and 370 are lysines and the amino acid at position 409 is a leucine; and a second IgG1 CH3 domain having an amino acid sequence that is at least 80% identical to the sequence set forth in SEQ ID NO:11, wherein the amino acid at position 370 is a serine, the amino acid at position 397 is an isoleucine, and the amino acids at positions 405 and 409 are lysines. The amino acid positions above are based on the EU numbering system.

In some embodiments of the above two aspects, the bispecific antibody includes two IgG1 CH2 domains. In some embodiments of the above two aspects, the bispecific antibody includes two IgG4 CH2 domains. In some embodiments, a single polypeptide chain comprises the first VH and the first IgG1 CH3 domain. In some embodiments, a single polypeptide chain comprises the first VH and the second IgG1 CH3 domain. In other embodiments, a single polypeptide chain comprises the first VL and the first IgG1 CH3 domain. In yet other embodiments, a single polypeptide chain comprises the first VL and the second IgG1 CH3 domain. In some embodiments, single polypeptide chain comprises the second VH and the second IgG1 CH3 domain. In some embodiments, single polypeptide chain comprises the second VH and the first IgG1 CH3 domain. In some embodiments, single polypeptide chain comprises the second VH and the second IgG1 CH3 domain. In some embodiments, the first polypeptide and/or the second polypeptide comprise the amino acid sequence set forth in SEQ ID NO:2. In certain embodiments, the first polypeptide and/or the second polypeptide comprise an amino acid sequence that is at least 90% identical to amino acids 7-112 of the amino acid sequence set forth in SEQ ID NO:2. In other embodiments, the first polypeptide and/or the second polypeptide comprise amino acids 7-112 of the amino acid sequence set forth in SEQ ID NO:2. In certain embodiments, the first polypeptide and/or the second polypeptide differ from the amino acid sequence set forth in SEQ ID NO:2 at at least twelve amino acid residues. In some embodiments, the first polypeptide and the second polypeptide each contain an amino acid other than cysteine at the cysteine residue of SEQ ID NO:2 that does not form an intrachain disulfide bond. In certain embodiments, the first polypeptide and the second polypeptide have a mutation or mutations at the N-linked glycosylation site such that the first polypeptide and the second polypeptide are not glycosylated at the N-linked glycosylation site. In other embodiments, the first polypeptide or the second polypeptide have a mutation or mutations at the N-linked glycosylation site such that the first polypeptide and the second polypeptide are not glycosylated at the N-linked glycosylation site. These mutations can be of the asparagine or the threonine or serine of the N-linked glycosylation site to other amino acid(s). In certain embodiments, the disclosure provides a polynucleotide or polynucleotides encoding the bispecific antibody described above. In some embodiments, expression vectors are provided comprising the bispecific antibody described above. In other embodiments, host cells comprising the bispecific antibody or the expression vectors are provided. In yet other embodiments, provided are methods of making the bispecific antibody comprising culturing the host cells described above under conditions that result in the expression of the bispecific antibody and isolating the bispecific antibody from the cell culture. In certain embodiments, the isolated bispecific antibody is formulated as a sterile composition for administration to a human subject in need thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 3B is a bar graph showing molar ratios and relative amounts of the components that were estimated from LC-MS.

FIG. 3C is a depiction of the melting temperature of purified heterodimers that was determined by DSC.

FIG. 4A shows the expression of heterodimerization mutants and half-antibody formation. CHO cells were transfected with various ratios of mp4a and mp4b heavy chains, which contain the same Fab (M60-A02 anti EGFR). Half-antibody formation in the expressed proteins was analyzed by SDS PAGE

FIG. 5C is a sequence alignment of human IgG1 CH1/hinge and kappa constant with the Cε2 domain and the E-Fab heavy and light chain (SEQ ID NOs: 91, 73, 1, 3 and 4, respectively, in order of appearance). The sequences are aligned with IMGT numbering shown above, the 7 β-strands of the Ig-fold are indicated by arrows, the conserved Pro at the start of β-strand A is in bold and underlined. The agly mutation (N38Q) in E-Fabs and interchain disulfide cysteines are also in bold and underlined.

FIG. 5D is a sequence alignment of IgE CH2 domains from human (SEQ ID NO: 1), chimpanzee (SEQ ID NO: 92), mouse (SEQ ID NO: 93), rat (SEQ ID NO: 94), and rabbit (SEQ ID NO: 95). Identical residues are shown as dots.

FIG. 6A is a schematic representation of the strategy to test light chain pairing. The heavy chain of the Fab A (HCA) is fused to HSA, while the light chain of Fab B (LCB) was tagged at the N-terminus with GFP. Correct pairing of the chains can be checked by molecular weight of the Fabs.

FIG. 6C is an analysis of Fab-pairing by SDS-page. The anti-IGF-1R Fab C06 was built as E-fab and light chain pairing with another anti-IGF-1R Fab (G11) was tested as in FIG. 6B.

FIG. 8A is an analysis of EGFR/IGF-1R bispecific antibodies expressed in CHO-S cells and supernatants by SDS-PAGE. The E-bodies E0 and E2 contain the anti-EGFR as E-Fab, while the IgG1-heterodimer control contains no light chain solution.

FIG. 8C is a graph depicting binding of the bispecific antibodies to His-tagged EGFR. Undiluted supernatants from CHO-S cells were used in Octet binding after loading of his-tagged ligands (5 µg/mL).

CH3 domains by lysine repositioning to drive heterodimerization of the two heavy chains of a bispecific antibody. In another embodiment, the CH1 and CL domains of one of the Fab arms are substituted with an IgE CH2 domain (or an IgM CH2 domain), or a fragment thereof that can still pair with the IgE CH2 domain (or the IgM CH2 domain). This engineering of the Fabs can reduce or prevent mispairing of light chains in the bispecific antibody. This disclosure describes the design, engineering, and testing of a bispecific antibody platform, which can efficiently generate an asymmetric IgG from 2 antibodies by co-expression.

Solution to Light Chain Mispairing Problem

Figure 1:
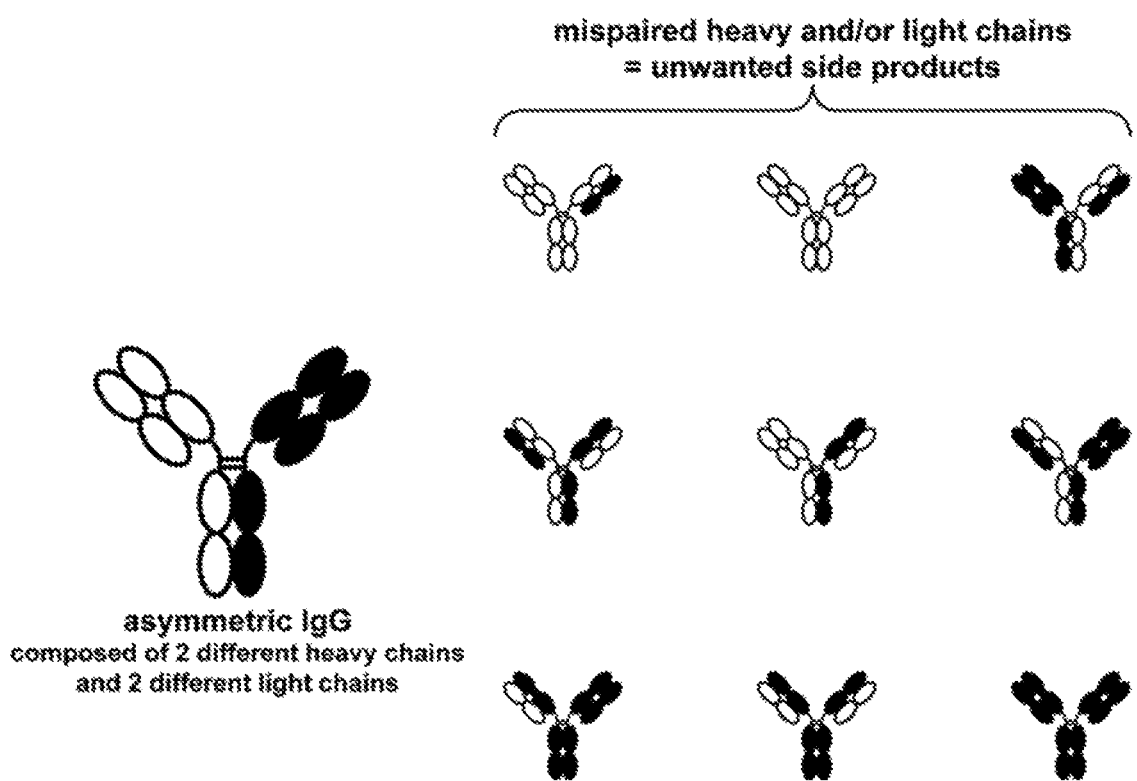
FIG. 1 is a diagrammatic representation of unwanted side products from mispairing in an asymmetric antibody. This figure shows that several unwanted side products can form by mispairing of light and/or heavy chains when two antibodies are co-expressed. The desired asymmetric antibody may represent a minor fraction, and purification of that desired antibody may present difficulties.

In order to achieve the correct assembly of the light chain (LC): heavy chain (HC) pairs in a bispecific antibody as illustrated in FIG. 1, the solution disclosed herein is to modify the amino acid sequence of the light chain and heavy chain such that the constant domains (i.e., the CL and CH1 domains) of these chains are replaced with an Ig-fold domain (or fragments thereof that can still form stable disulfide-linked dimers between the Ig-fold domains of the light and heavy chains).

In one instance the Ig-fold domain that replaces the CH1 and CL domains is the CH2 domain of IgE ("CH2E"), or a fragment thereof that can form stable disulfide-linked dimers with another CH2E. The amino acid sequence of an exemplary CH2E domain is provided below:

```
                                                   (SEQ ID NO: 1)
  1 VCSRDFTPPT VKILQSSCDG GGHFPPTIQL LCLVSGYTPG TINITWLEDG

51 QVMDVDLSTA STTQEGELAS TQSELTLSQK HWLSDRTYTC  QVTYQGHTFE

101 DSTKKCA
```

DETAILED DESCRIPTION

Bispecific antibodies are an emerging class of biologics drugs that hold the potential of achieving new therapeutic mechanisms of action. However, there are several challenges associated with expressing and properly forming a bispecific antibody. Specifically, two problems must be solved to efficiently express a bispecific antibody in the form of an asymmetric IgG composed of four different chains: the so-called heavy chain mispairing problem and the light chain mispairing problem. When there are two different heavy chains and two different light chains, they can mispair in several different permutations (see, FIG. 1). Thus, to form a properly paired bispecific antibody, the two heavy chains must form a heterodimer, and each heavy chain must pair with its cognate light chain. This disclosure provides a bispecific antibody platform that can convert any two antibodies that each bind different epitopes into a bispecific antibody in the form of an asymmetric IgG. The platform is based on a heavy chain heterodimerization strategy termed lysine repositioning, and a solution to the light chain mispairing problem that does not require engineering of the variable domains of antibodies. In one embodiment, the platform contains an Fc region, which is engineered in the In the sequence shown above, the two cysteines that can be involved in forming interchain disulfide bonds are boldened; the two cysteines that can form intradomain disulfide bonds are boldened and italicized; and the N-linked glycosylation site is underlined.

In another instance, the Ig-fold domain that replaces the CH1 and CL domains of the heavy and light chain is the CH2 domain of IgM ("CH2M"), or a fragment thereof that can form stable disulfide-linked dimers. The amino acid sequence of an exemplary CH2M domain is provided below:

```
                                                   (SEQ ID NO: 2)
  1 VIAELPPKVS VFVPPRDGFF GNPRKSKLIC QATGFSPRQI QVSWLREGKQ

51 VGSGVTTDQV QAEAKESGPT TYKVTSTLTI KESDWLGQSM FTCRVDHRGL

101 TFQQNASSMC VP
```

In the sequence shown above, the cysteine that can be involved in forming interchain disulfide bonds is boldened; the two cysteines that can form intradomain disulfide bonds are italicized; and the N-linked glycosylation site is underlined.

This disclosure provides several examples of antibodies making use of the solution to the light chain pairing problem. In one embodiment, the antibody features amino acid sequences having the formulas:

VH1 construct: VH1-L-X-CH2E (or CH2M); and

VL1 construct: VL1-L-X-CH2E (or CH2M), wherein "VH1" and "VL1" are the heavy chain variable domain and light chain variable domain that pair to form a first antigen-binding site for a first epitope; wherein "L" is an optional linker (described further below); wherein "X" is an optional elbow region (described further below); and wherein "CH2E" refers to SEQ ID NO:1 or a fragment thereof that can form stable disulfide-linked dimers with SEQ ID NO:1 (e.g., amino acids 9-107 of SEQ ID NO:1), and wherein "CH2M" refers to SEQ ID NO:2 or a fragment thereof that can form stable disulfide-linked dimers with SEQ ID NO:2 (e.g., amino acids 7-112 of SEQ ID NO:2). In certain embodiments, one or both "L" and "X" are absent in the VH1 and VL1 constructs.

In another embodiment, the antibody features amino acid sequences having the formulas:

VH1 construct: VH1-X-L-CH2E (or CH2M), and

VL1 construct: VL1-X-L-CH2E (or CH2M).

In a further embodiment, the antibody features amino acid sequences having the formulas:

VH1 construct: VH1-L-X-L-CH2E (or CH2M), and

VL1 construct: VL1-L-X-L-CH2E (or CH2M).

It is to be understood that when CH2E is used in a VH1 construct described above, CH2E is also used in the corresponding VL1 construct. Similarly, when CH2M is used in a VH1 construct described above, CH2M is also used in the corresponding VL1 constructs. The CH2E and CH2M domains in the paired VH1 and VL1 constructs described above may be identical in amino acid sequence; however, they need not be identical. They may, e.g., differ at 12 or fewer, 11 or fewer, 10 or fewer, 9 or fewer, 8 or fewer, 7, or fewer, 6 or fewer, 5 or fewer, 4 or fewer, 3 or fewer, 2 or fewer, or 1, 2, 3, 4, 5, 6, 7, 8, 9, 10, 11, or 12 amino acids. In certain embodiments, the CH2E domains of the VH1 and VL1 constructs described above are different at 12 or fewer, 11 or fewer, 10 or fewer, 9 or fewer, 8 or fewer, 7, or fewer, 6 or fewer, 5 or fewer, 4 or fewer, 3 or fewer, 2 or fewer, or 1 amino acid position(s) compared with SEQ ID NO:1. In certain embodiments, the CH2M domains of the VH1 and VL1 constructs described above are different at 12 or fewer, 11 or fewer, 10 or fewer, 9 or fewer, 8 or fewer, 7, or fewer, 6 or fewer, 5 or fewer, 4 or fewer, 3 or fewer, 2 or fewer, or 1 amino acid position(s) compared with SEQ ID NO:2. These differences may be the result of amino acid substitutions, deletions, and/or insertions. For example, the N-glycosylation site in SEQ ID NOs.: 1 or 2 can be modified (e.g., in the NIT sequence of SEQ ID NO:1, the N residue can be changed to Q or the T residue changed to A or C; in the NAS sequence in SEQ ID NO:2, the N residue can be changed to Q or the S residue changed to A or C). Alternatively, or in addition, one or more of the cysteines that form intradomain disulfide bonds may be mutated only in the CH2E (or CH2M) domain of one of the VH1 and VL1 constructs. In certain instances, the cysteine or cysteines involved in interchain disulfide bond formation in both the CH2E domains (or CH2M domains) of the VH1 and VL1 constructs are substituted (e.g., with a conservative amino acid). Also, mutations to prevent homodimerization of the CH2E domains (or CH2M domains) may be made (e.g., replacing serine at position 17 of SEQ ID NO:1 with e.g., isoleucine or threonine; and replacing threonine at position 103 of SEQ ID NO:1 with e.g., glycine or serine). The alignment of the IgE CH2 domains from human, chimpanzee, mouse, rat, and rabbit (FIG. 5D) identifies amino acid residues that are not conserved between all species and can likely be substituted without eliminating bioactivity.

In some instances the amino acid substitutions to the CH2E domain can be conservative. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

In some instances the amino acid substitutions to the CH2E domain can be non-conservative. Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

In certain embodiments, the CH2E domains of the VH1 and VL1 constructs described above are at least 75%, at least 80%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, or at least 99% identical to the amino acid sequence set forth in SEQ ID NO:1 and the CH2E domains of the VH1 and VL1 constructs can still pair together. In certain embodiments, the CH2E domains of the VH1 and VL1 constructs described above are at least 75%, at least 80%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, or at least 99% identical to the amino acid sequence set forth in SEQ ID NO:3 and the CH2E domains of the VH1 and VL1 constructs can still pair together.

In certain embodiments, if CH2M domains are employed in the VH1 and VL1 constructs described above, the CH2M domains are at least 75%, at least 80%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, or at least 99% identical to the amino acid sequence set forth in SEQ ID NO:2 and the CH2M domains of the VH1 and VL1 constructs can still pair together.

Percent identity between amino acid sequences can be determined using the BLAST 2.0 program. Sequence comparison can be performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et al., Nucleic Acids Research, 25:3389-3402 (1997).

In certain embodiments, the CH2E domain that is used in both the VH1 and VL1 constructs described above is 100% identical to SEQ ID NO:1. In some embodiments, the CH2E domain that is used in the VH1 and VL1 constructs described above is a fragment of SEQ ID NO:1, e.g., missing amino acids at the N and/or C-terminal of SEQ ID NO:1, and which can form stable disulfide-linked dimers with a polypeptide encoded by SEQ ID NO:1. For example, the fragments of SEQ ID NO:1 may be missing 20, 19, 18, 17, 16, 15, 14, 13, 12, 10, 9, 8, 7, 6, 5, 4, 3, 2, or 1 amino acid(s) at the N- and/or C-terminus of SEQ ID NO:1. In certain embodiments, the CH2E domain that is used in VH1 and VL1 constructs described above comprises or consists of amino acids 2-107, 3-107, 4-107, 5-107, 6-107, 7-107, 8-107, 9-107, 10-107, 11-107, 12-107, 13-107, 14-107, 15-107, 16-107, 17-107, 18-107, 19-107, or 20-107 of SEQ ID NO:1. In other embodiments, the CH2E domain that is used in VH1 and VL1 constructs described above comprises or consists of amino acids 2-106, 3-106, 4-106, 5-106, 6-106, 7-106, 8-106, 9-106, 10-106, 11-106, 12-106, 13-106, 14-106, 15-106, 16-106, 17-106, 18-106, 19-106, or 20-106 of SEQ ID NO:1. In yet other embodiments, the CH2E domain that is used in VH1 and VL1 constructs described above comprises or consists of amino acids 2-105, 3-105, 4-105, 5-105, 6-105, 7-105, 8-105, 9-105, 10-105, 11-105, 12-105, 13-105, 14-105, 15-105, 16-105, 17-105, 18-105, 19-105, or 20-105 of SEQ ID NO:1. In certain embodiments, the CH2E domain that is used in VH1 and VL1 constructs described above comprises or consists of amino acids 9-107, 9-106, 9-105, 9-104, 9-103, 9-102, 9-101, 9-100, 9-99, 9-98, or 9-97 of SEQ ID NO:1. In all of these embodiments, there may be one to twelve (1, 2, 3, 4, 5, 6, 7, 8, 9, 10, 11, or 12) substitutions compared to the amino sequence set forth in SEQ ID NO:1 in one or both CH2E domains used in the VH1 and VL1 constructs described above. For example, the N-linked glycosylation site may be mutated (e.g., asparagine of the NIT site may be substituted by glutamine or the threonine of the NIT site may be substituted by alanine or cysteine); one or both of the cysteines involved in interchain disulfide bond formation may be substituted with another amino acid (e.g., a conservative amino acid); or mutations may be introduced into CH2E that prevent formation of heavy chain:heavy chain or light chain:light chain dimers (when the CH2E domain is part of the heavy chain and light chain).

In certain embodiments, the CH2M domain that is used in VH1 and VL1 constructs described above is 100% identical to SEQ ID NO:2. In some embodiments, the CH2M domain that is used in VH1 and VL1 constructs described above is a fragment of SEQ ID NO:2, e.g., missing amino acids at the N and/or C-terminal of SEQ ID NO:2, and which can form stable disulfide-linked dimers with a polypeptide encoded by SEQ ID NO:2. For example, the fragments of SEQ ID NO:2 may be missing 20, 19, 18, 17, 16, 15, 14, 13, 12, 10, 9, 8, 7, 6, 5, 4, 3, 2, or 1 amino acid(s) at the N- and/or C-terminus of SEQ ID NO:2. In certain embodiments, the CH2M domain that is used in VH1 and VL1 constructs described above comprises or consists of amino acids 2-112, 3-112, 4-112, 5-112, 6-112, 7-112, 8-112, 9-112, 10-112, 11-112, 12-112, 13-112, 14-112, 15-112, 16-112, 17-112, 18-112, 19-112, or 20-112 of SEQ ID NO:2. In other embodiments, the CH2M domain that is used in VH1 and VL1 constructs described above comprises or consists of amino acids 2-111, 3-106, 4-111, 5-111, 6-111, 7-111, 8-111, 9-111, 10-111, 11-111, 12-111, 13-111, 14-111, 15-111, 16-111, 17-111, 18-111, 19-111, or 20-111 of SEQ ID NO:2. In yet other embodiments, the CH2M domain that is used in VH1 and VL1 constructs described above comprises or consists of amino acids 2-110, 3-110, 4-110, 5-110, 6-110, 7-110, 8-110, 9-110, 10-110, 11-110, 12-110, 13-110, 14-110, 15-110, 16-110, 17-110, 18-110, 19-110, or 20-110 of SEQ ID NO:2. In certain embodiments, the CH2M domain that is used in VH1 and VL1 constructs described above comprises or consists of amino acids 7-112, 7-111, 7-110, 7-109, 7-108, 7-107, 7-105, 7-104, 7-103, 7-102, 7-101, 7-100, or 7-99 of SEQ ID NO:1. In all of these embodiments, there may be one to twelve (1, 2, 3, 4, 5, 6, 7, 8, 9, 10, 11, or 12) substitutions compared to the amino sequence set forth in SEQ ID NO:2 in one or both CH2M domains used in the VH1 and VL1 constructs described above. For example, the N-linked glycosylation site may be mutated (e.g., asparagine of the NAS site may be substituted by glutamine or the serine of the NAS site may be substituted by alanine or cysteine); one or both of the cysteines involved in interchain disulfide bond formation may be substituted with another amino acid (e.g., a conservative amino acid); or mutations may be introduced into CH2M that prevent formation of heavy chain:heavy chain or light chain:light chain dimers (when the CH2M domain is part of the heavy chain and light chain).

In one embodiment, the CH2 domain used in the VH1 constructs described above is a CH2 domain of human immunoglobulin E, in which the N-glycosylation site is mutated to glutamine, and the first κ amino acids are replaced with the first 5 amino acids of a human IgG1 CH1 domain. The amino acid sequence of this CH2E domain is provided below:

```
                                                          (SEQ ID NO: 3)
  1 ASTKGPTVKI LQSSCDGGGH FPPTIQLLCL VSGYTPGTIQ ITWLEDGQVM

51 DVDLSTASTT QEGELASTQS ELTLSQKHWL SDRTYTCQVT YQGHTFEDST

101 KKCA
```

In one embodiment, the CH2 domain used in the VL1 constructs described above is a CH2 domain of human immunoglobulin E, in which the N-glycosylation site is mutated to glutamine, and the first 8 amino acids are replaced with the first 5 amino acids of a human kappa domain. The amino acid sequence of this CH2E domain is provided below:

```
                                                       (SEQ ID NO: 4)
  1 RTVAAPTVKI LQSSCDGGGH FPPTIQLLCL VSGYTPGTIQ ITWLEDGQVM

51 DVDLSTASTT QEGELASTQS ELTLSQKHWL SDRTYTCQVT YQGHTFEDST

101 KKCA
```

In another embodiment, the amino acid sequence of an exemplary CH2 domain of human immunoglobulin E to be used in a VH1 construct described above, and which is engineered to form a heterodimer with a VL1 construct described above, is made by replacing serine at position 17 of SEQ ID NO:1 with isoleucine. The amino acid sequence of this CH2E domain is provided below (note that in this sequence the N-linked glycosylation site is also mutated and the first eight amino acids of SEQ ID NO:1 are replaced with the first 5 amino acids of IgG1 CH1):

```
                                                       (SEQ ID NO: 5)
  1 ASTKGPTVKI LQSICDGGGH FPPTIQLLCL VSGYTPGTIQ ITWLEDGQVM

51 DVDLSTASTT QEGELASTQS ELTLSQKHWL SDRTYTCQVT YQGHTFEDST

101 KKCA
```

The amino acid sequence of an exemplary CH2 domain of human immunoglobulin E to be connected with a VL domain of a VL1 construct described above, and which is engineered to form a heterodimer with a VH1 construct described above, is made by replacing threonine at position 103 of SEQ ID NO:1 with glycine. The amino acid sequence of this CH2E domain is provided below (note that in this sequence the N-linked glycosylation site is also mutated and the first eight amino acids of SEQ ID NO:1 are replaced with the first 5 amino acids of the kappa chain):

```
                                                       (SEQ ID NO: 6)
  1 RTVAAPTVKI LQSSCDGGGH FPPTIQLLCL VSGYTPGTIQ ITWLEDGQVM

51 DVDLSTASTT QEGELASTQS ELTLSQKHWL SDRTYTCQVT YQGHTFEDSG

101 KKCA
```

In certain embodiments, the CH2E domain that is used in VH1 and VL1 constructs described above include C-terminal truncations of SEQ ID NOs.: 5 and/or 6. In certain instances, the C-terminal most 9, 8, 7, 6, 5, 4, 3, 2, or 1 amino acid of SEQ ID NO:5 and/or SEQ ID NO:6 is deleted. In a specific embodiment, the CH2E domain that is used in the VH1 constructs described above comprise or consist of amino acids 1-103, 1-102, 1-101, 1-100, 1-99, 1-98, 1-97, 1-96, or 1-95 of SEQ ID NO:5. In another specific embodiment, the CH2E domain that is used in the VL1 constructs described above comprise or consist of amino acids 1-103, 1-102, 1-101, 1-100, 1-99, 1-98, 1-97, 1-96, or 1-95 of SEQ ID NO:6. In yet other embodiments, the CH2E domain that is used in the VH1 constructs described above comprises or consists of amino acids 6-103, 7-103, 8-103, 9-103, or 10-103 of SEQ ID NO:5. In yet other embodiments, the CH2E domain that is used in the VL1 constructs described above comprises or consists of amino acids 6-103, 7-103, 8-103, 9-103, or 10-103 of SEQ ID NO:6. In certain embodiments, SEQ ID NO:5 and/or SEQ ID NO:6, or the fragments thereof described above, may additionally contain five or fewer, four or fewer, three or fewer, two or fewer or one further mutation relative to SEQ ID NO:1.

In certain embodiments, the antibodies described above further comprise a heavy chain variable domain "VH2" and a light chain variable domain "VL2", wherein the VH2 is connected to a CH1 domain and the VL2 domain is connected to a CL domain, and wherein the VH2 and VL2 pair to form a second antigen-binding site for a second epitope. In some embodiments, the antibodies described above further comprise two Fc domains. The Fc domains comprises a hinge region, a CH2 domain and a CH3 domain of an antibody. In certain instances, the hinge, CH2, and CH3 domains are from IgG1. In certain instances, the hinge and CH3 domains are from IgG4 and the CH2 domain from IgG1. In specific embodiments, when the hinge region is from IgG4, it includes the S228P (EU numbering) mutation. One of the two Fc domains of the antibody may be directly linked to one of the CH2E domains (or CH2M domain) of one of the two Fabs of the antibody, or may be linked via a linker. The Fc region may be linked to the VH1 construct or the VL1 construct. The Fc region may comprise any mutation(s) that increase heterodimerization between the heavy chains of the bispecific antibody relative to the same Fc regions without the mutation(s). For example, the Fc regions may comprise knobs-into-holes mutations, electrosteering mutations, or other mutations described in Table 2 of Example 1 of this application. In a specific embodiment, the Fc regions of the bispecific antibody include lysine repositioning mutations described herein.

In certain embodiments, the antibodies described above further comprise a heavy chain variable domain "VH2" and a light chain variable domain "VL2", wherein the VH2 is connected to a CH1 domain and the VL2 domain is connected to a CL domain, and wherein the VH2 and VL2 pair to form a second antigen-binding site for a second epitope, but the antibody lacks an Fc domain(s). The CH2E domain (or CH2M domain) linked to the VH1 or VL1 domain of the constructs described above can be linked to the antibody comprising the VH2 and VL2 domains. For example, the C-terminus of the CH2E domain (or CH2M domain) of the VH1 construct may be linked to the C-terminus of the CH1 domain that is connected to VH2, or the C-terminus of CH2E domain (or CH2M domain) of the VH1 construct may be linked to the N-terminus of the VH2 domain. Other exemplary configurations are for the C-terminus of the CH2E domain (or CH2M domain) of the VL1 construct may be linked to the C-terminus of the CH1 domain that is connected to VH2, or the C-terminus of the CH2E domain (or CH2M domain) of the VL1 construct may be linked to the N-terminus of the VH2 domain. Other exemplary configurations include the C-terminus of the CH2E domain (or CH2M domain) of the VH1 construct linked to the C-terminus of the CL domain that is connected to VL2, or the C-terminus of the CH2E domain (or CH2M domain) of the VH1 construct linked to the N-terminus of the VL2 domain. Further exemplary configurations are for the C-terminus of the CH2E domain (or CH2M domain) of the VL1 construct to be linked to the C-terminus of the CL domain that is connected to VL2, or the C-terminus of the CH2E domain (or CH2M domain) of the VL1 construct to be linked to the N-terminus of the VL2 domain. In some instances, the linker between the CH2E domain (or CH2M domain) of the VH1 or VL1 construct and the second Fab is a peptide linker. In other instances, the linker between the CH2E domain (or CH2M domain) of the VH1 or VL1 construct and the second Fab is human serum albumin (HSA). In some instances, the linker between the CH2E domain (or CH2M domain) of the VH1 or VL1 construct and the second Fab is polyethylene glycol. In yet other instances, the linker between the CH2E domain of the VH1 or VL1 construct and the second Fab is an XTEN molecule (e.g., AE-144, AE-288).

In certain instances, the VH1 and VL1 constructs are part of a tetravalent bispecific antibody. These tetravalent antibodies comprise (i) a whole antibody, the variable domains of which bind one epitope of an antigen, and (ii) two Fabs that each bind another epitope of the same antigen or a different antigen. In some embodiments, the whole antibody is an IgG1. In other embodiments, the whole antibody is an IgG4(G1)—i.e., an antibody comprising the hinge and CH2 regions of IgG4 but the CH3 domain of IgG1. In certain embodiments, the whole antibody is an IgG4(G1)P—i.e., where the antibody is an IgG4(G1) except that the hinge region has the S228P (EU numbering) mutation. The two Fabs are linked to the C-terminus of the CH3 domains of the whole antibody. The two Fabs may be linked to the CH3 domain of the whole antibody either via the N-terminus of one of the two variable domains (i.e., VH or VL) of each Fab or via the C-terminus of one of the constant domains of each of the two Fabs. If the Fab constant domain is not replaced by CH2E or CH2M domains, the linkage may be to either the C-terminus of the CH1 domain or the C-terminus of the CL domain. If the Fab constant domains are replaced with the CH2E domains (or CH2M domains), the linkage can be to the C-terminus of the CH2E domain (or CH2M domain)). The tetravalent bispecific antibodies can include the CH2E domains (or CH2M domains) detailed above either in the two arms of the whole antibody or in the two Fabs. Note that, in this instance, the term "whole antibody" is used differently than its usual meaning (i.e., an antibody comprising four chains: VL1-CL, VH1-CH1-hinge-CH2-CH3, VL2-CL, and VH2-CH1-hinge-CH2-CH3) to also include an antibody comprising four chains: VL1-CH2E (or CH2M), VH1-CH2E(or CH2M)-hinge-CH2-CH3, VL2-CH2E(or CH2M), and VH2-CH2E(or CH2M)-hinge-CH2-CH3.

There is no particular limitation on the linkers that can be used in the constructs described above. In some embodiments, the linker is a peptide linker. Any arbitrary single-chain peptide comprising about one to 25 residues (e.g., 2, 3, 4, 5, 6, 7, 8, 9, 10, 11, 12, 13, 14, 15, 16, 17, 18, 19, 20 amino acids) can be used as a linker. In certain instances, the linker contains only glycine and/or serine residues. Examples of such peptide linkers include: Gly; Ser; Gly Ser; Gly Gly Ser; Ser Gly Gly; Gly Gly Gly Ser (SEQ ID NO: 10); Ser Gly Gly Gly (SEQ ID NO:55); Gly Gly Gly Gly Ser (SEQ ID NO:56); Ser Gly Gly Gly Gly (SEQ ID NO:57); Gly Gly Gly Gly Gly Ser (SEQ ID NO:58); Ser Gly Gly Gly Gly Gly (SEQ ID NO:59); Gly Gly Gly Gly Gly Gly Ser (SEQ ID NO:60); Ser Gly Gly Gly Gly Gly Gly (SEQ ID NO:61); (Gly Gly Gly Gly Ser)n (SEQ ID NO:56)n, wherein n is an integer of one or more; and (Ser Gly Gly Gly Gly)n(SEQ ID NO:57)n, wherein n is an integer of one or more. In other embodiments, the linker peptides are modified such that the amino acid sequence GSG (that occurs at the junction of traditional Gly/Ser linker peptide repeats) is not present. For example, the peptide linker comprise an amino acid sequence selected from the group consisting of: (GGGXX)nGGGGS (SEQ ID NO:62) and GGGGS(XGGG-S)n(SEQ ID NO:63), where X is any amino acid that can be inserted into the sequence and not result in a polypeptide comprising the sequence GSG, and n is O to 4. In one embodiment, the sequence of a linker peptide is (GGGX1X2)nGGGGS and X1 is P and X2 is S and n is O to 4 (SEQ ID NO:64). In another embodiment, the sequence of a linker peptide is (GGGX1X2)nGGGGS and X1 is G and X2 is Q and n is O to 4 (SEQ ID NO:65). In another embodiment, the sequence of a linker peptide is (GGGX1X2)nGGGGS and X1 is G and X2 is A and n is O to 4 (SEQ ID NO:66). In yet another embodiment, the sequence of a linker peptide is GGGGS(XGGGS)n, and X is P and n is O to 4 (SEQ ID NO:67). In one embodiment, a linker peptide of the invention comprises or consists of the amino acid sequence (GGGGA)2GGGGS (SEQ ID NO:68). In another embodiment, a linker peptide comprises or consists of the amino acid sequence (GGGGQ)2GGGGS (SEQ ID NO:69). In yet another embodiment, a linker peptide comprises or consists of the amino acid sequence (GGGPS) 2GGGGS (SEQ ID NO:70). In a further embodiment, a linker peptide comprises or consists of the amino acid sequence GGGGS(PGGGS)2 (SEQ ID NO:71).

In certain embodiments, the linker is a synthetic compound linker (chemical cross-linking agent). Examples of cross-linking agents that are available on the market include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), di sulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl] sulfone (sulfo-BSOCOES).

The elbow region for the VH1 construct can be, e.g., a fragment of an IgG CH1 domain (e.g., one to ten, one to nine, one to eight, one to seven, one to six, one to five, one to four, one to three, or one to two consecutive amino acids from an IgG CH1 domain). In one embodiment the elbow domain is from IgG1 and comprises or consists of one to ten, one to nine, one to eight, one to seven, one to six, one to five, one to four, one to three, or one to two consecutive amino acids from the N or C-terminus of an IgG1 CH1 domain. The amino acid sequence of an IgG1 CH1 domain is provided below:

```
                                              (SEQ ID NO: 72)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKV
```

A non-limiting example of an elbow region for the VH1 constructs described above is ASTKG (SEQ ID NO:7). In one embodiment the VH1 construct comprises the following amino acid sequence:

```
                                                    (SEQ ID NO: 45)
  1 ASTKGPTVKI LQSSCDGGGH FPPTIQLLCL VSGYTPGTIN ITWLEDGQVM

51 DVDLSTASTT QEGELASTQS ELTLSQKHWL SDRTYTCQVT YQGHTFEDST

101 KKCA
``` wherein the first 8 amino acids of CH2E (VCSRDFTP (SEQ ID NO:8) are replaced with the first 5 amino acids of a human IgG1 CH2 domain (elbow region ASTKG (SEQ ID NO:7)). In another embodiment, the elbow region for the VH1 constructs described above is SRDFT (SEQ ID NO:77). In certain embodiments, the VH1 constructs have a linker but no elbow region. In such instances, the linker can be, e.g., SEQ ID NO:56 or SEQ ID NO:58.

The elbow region for the VL1 construct can be, e.g., a fragment of a kappa or lambda CL domain (e.g., one to ten, one to nine, one to eight, one to seven, one to six, one to five, one to four, one to three, one to two consecutive amino acids from the kappa or lambda domains). In one embodiment the elbow domain is from the kappa domain and comprises or consists of one to ten, one to nine, one to eight, one to seven, one to six, one to five, one to four, one to three, or one to two consecutive amino acids from the N or C-terminus of a kappa domain. The amino acid sequence of the human kappa CL domain is provided below:

```
                                          (SEQ ID NO: 73)
 RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC
```

The amino acid sequence of the human lambda CL domain is provided below (the elbow region is the first six amino acids, shown as bold/underlined):

```
                                          (SEQ ID NO: 74)
 GQPKAAPSVT LFPPSSEELQ ANKATLVCLI SDFYPGAVTV

AWKADSSPVK AGVETTTPSK QSNNKYAASS YLSLTPEQWK

SHRSYSCQVT HEGSTVEKTV APTECS
```

A non-limiting example of an elbow region for the VL1 constructs described above is RTVAA (SEQ ID NO:9). In one embodiment the VL1 construct comprises the following amino acid sequence:

wherein the first 8 amino acids of CH2E (VCSRDFTP (SEQ ID NO:8)) are replaced with the first 5 amino acids of a human kappa domain (elbow region RTVAA (SEQ ID NO:9)). In another embodiment, the elbow region for the VL1 constructs described above is GQPKAA (SEQ ID NO:78). In certain embodiments, the VL1 constructs have a linker but no elbow region. In such instances, the linker can be, e.g., SEQ ID NO:56 or SEQ ID NO:58.

Solution to Heavy Chain Mispairing Problem

This application also discloses lysine repositioning as an effective strategy for heavy chain heterodimerization. Based on structural analysis of the CH3 domains, modeling, and analysis of potential interface mutations, a strategy of lysine repositioning was devised to engineer asymmetric complementary CH3 interfaces (see, FIG. 2). Specifically, substitution of Lys409 (EU numbering) with Ser and Ser364 (EU numbering) with Lys in CH3 monomer A repositions the lysine from β-strand E to the adjacent antiparallel β-strand B. Conversely, substitution of Lys370 (EU numbering) with Ser and Phe405 (EU numbering) with Lys in CH3 monomer B repositions the Lysine from β-strand B to β-strand E. In other embodiments, the lysine repositioning involves the mutations of MP4 of Table 2. The repositioned lysines are stacked in the heterodimer, but impose steric and charge clashes in the homodimers, which prevent their formation, and therefore drive heterodimerization of the CH3 domains. Thus, by incorporating these changes into the CH3 domain of an antibody (e.g., CH3 of an IgG1 antibody) one can increase heterodimerization of the heavy chain of an antibody relative to an antibody without these mutations. This strategy was found to be a highly effective strategy for heavy chain heterodimerization with superior or comparable efficiency to published Fc heterodimerization mutations.

The amino acid sequence of a wild type human IgG1 CH3 domain is provided below:

```
                                                    (SEQ ID NO: 46)
  1 RTVAAPTVKI LQSSCDGGGH FPPTIQLLCL VSGYTPGTIN ITWLEDGQVM

51 DVDLSTASTT QEGELASTQS ELTLSQKHWL SDRTYTCQVT YQGHTFEDST

101 KKCA
```

```
                                                            (SEQ ID NO: 11)
  1 GQPREPQVYT LPPSRDELTK NQVSLTCLVK GFYPSDIAVE WESNGQPENN

51 YKTTPPVLDS DGSFFLYSKL TVDKSRWQQG NVFSCSVMHE ALHNHYTQKS

101 LSLSPGK
```

The amino acid sequence of a wild type human IgG4 CH3 domain is provided below:

```
                                                            (SEQ ID NO: 12)
  1 GQPREPQVYT LPPSQEEMTK NQVSLTCLVK GFYPSDIAVE WESNGQPENN

51 YKTTPPVLDS DGSFFLYSRL TVDKSRWQEG NVFSCSVMHE ALHNHYTQKS

101 LSLSLGK
```

In one embodiment one of the two CH3 domains of an Fc region of an antibody comprises the amino acid sequence set forth below:

```
                                                            (SEQ ID NO: 13)
  1 GQPREPQVYT LPPSRDELTK NQVKLTCLVK GFYPSDIAVE WESNGQPENN YKTTPPVLDS

61 DGSFFLYSLL TVDKSRWQQG NVFSCSVMHE ALHNHYTQKS LSLSPG
```

In this embodiment, the second of the two CH3 domains of an Fc region of an antibody comprises the amino acid sequence set forth below:

```
                                                            (SEQ ID NO: 14)
  1 GQPREPQVYT LPPSRDELTK NQVSLTCLVS GFYPSDIAVE WESNGQPENN YKTTPPILDS

61 DGSFKLYSKL TVDKSRWQQG NVFSCSVMHE ALHNHYTQKS LSLSPG
```

In some embodiments, the above-mentioned two CH3 domains may include five or fewer, four or fewer, three or fewer, two or fewer, or one amino acid substitution in one or both CH3 domains. For example, the CH3 domain can be mutated to alter one or more effector functions of an antibody. Non-limiting examples of positions (according to EU numbering) that can be modified in a CH3 domain to alter one or more effector functions include positions 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439. See also examples of possible sites for substitutions and examples of mutations in U.S. Pat. No. 8,586,713 B2 at column 10, lines 32-64. Other non-limiting examples of substitutions (listed according to EU numbering) that can be made in a CH3 domain to alter one or more effector functions include E345R, H433A, N434A, H435A, Y436D, Q438D, K439E, S440K, and/or K439E/S440K (see, Diebolder C A et al., *Science*, 343 (6176): 1260-1263 (2014)). Other substitutions that can be made to a CH3 domain include those that affect binding to protein A. Non-limiting examples of such substitutions include H435R, H435R, and/or Y436F (U.S. Pat. No. 8,586, 713 B2) (all EU numbering). Substitutions may also be made to introduce an artificial disulfide bond. Non-limiting examples of such substitutions include P445G, G446E, and K447C; P343C and A431C; and S375C and P396C (WO2011/003811 A1) (all EU numbering). The CH3 domain may be mutated to make changes to surface residues. This can be, e.g., for altering the isoelectric point (pI) of the antibody. Non-limiting examples of such substitutions include E345K, Q347E/K/R, R355E, R355Q, K392E, K392N, Q419E (US 2014/0294835 A1) (all EU numbering).

In some instances, the C-terminal of the CH3 domain can be truncated and/or modified. For example, one can delete K447 (EU numbering) and/or add the peptide DEDE or other amino acids to the C-terminus of the CH3 domain. In certain instances, the CH3 domain can be mutated to affect glycosylation of the domain. A non-limiting example of such a mutation is Y407E (EU numbering) (Rose et al., MAbs, 5(2):219-28 (2013)).

The CH3 domains described above can be part of an Fc domain. The Fc domain of a heavy chain of an antibody includes the hinge region, a CH2 domain and a CH3 domain. The CH3 domain may include mutations in addition to the lysine repositioning mutations discussed above. The hinge region in the Fc domain can be a hinge region of any antibody class. The hinge region of the IgG1, IgG2, and IgG4 antibodies generally extend from the amino acid at position 216 to the amino acid at position 230 (position numbering according to EU numbering). In certain embodiments, the hinge region is a hinge from an IgG1 antibody. In other embodiments, the hinge region is a hinge from an IgG4 antibody. When the hinge region is from the IgG4 class it may contain the S228P (EU numbering) mutation. Below are exemplary hinge regions that can be employed either in whole or in part (e.g., there can be N- and/or C-terminal truncations).

```
                                         (SEQ ID NO: 15)
    Human IgG1 hinge: EPKSCDKTHTCPPCP (SEQ ID NO: 16)
    Human IgG4 hinge: ESKYGPPCPSCP (SEQ ID NO: 17)
    Mutant human IgG4 (S228P) hinge: ESKYGPPCPPCP
```

In certain instances, 1, 2, 3, 4, or 5 amino acids may be deleted at the N- and/or C-terminus of the above hinge sequences. In certain instances, there could be four or fewer, three or fewer, two or fewer, one, two, three, or four amino acid substitutions, deletions, and/or insertions in the hinge sequences or N- and/or C-terminal truncations thereof.

The CH2 domain can be from any class of antibody. In certain embodiments, the CH2 domain is from an IgG1 antibody. In other embodiments, the CH2 domain is from an IgG4 antibody. The CH2 domains may contain one or more mutations. For example, the CH2 domain may have a mutation of the N-linked glycosylation site such that that site is not glycosylated. In certain embodiments, the asparagine in the N-linked glycosylation site of a CH2 domain is mutated to glutamine (e.g., Asn297Gln). In other embodiments, the threonine in the N-linked glycosylation site of a CH2 domain is mutated to alanine or cysteine (e.g., Thr299Ala or Thr299Cys). In other examples, the CH2 domain may be mutated to change the effector function, e.g., Leu234Ala/Leu235Ala, Pro329Gly, and/or. Pro331Ser. The CH2 domain can also be mutated to change binding to FcRn.

In certain embodiments, the constant domain is an IgG4P/IgG1 hybrid. In certain instances, the constant domain is an IgG4P/IgG1 (agly) hybrid. These hybrids include the hinge region and CH2 domain of IgG4 and the CH3 domain of IgG1. The hinge region of IgG4 has the S228P mutation. In the agly construct, it further includes one of an N297Q, T299A, or T299C mutation.

In one embodiment, one of the two Fc regions comprises the amino acid sequence set forth below (hinge region italicized; N-linked glycosylation site underlined; CH2 region in regular font; CH3 domain boldened):

```
                                            (SEQ ID NO: 18)
DKTHTCPPCP APELLGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSRDELTK NQVKLTCLVK GFYPSDIAVE

WESNGQPENN YKTTPPVLDS DGSFFLYSLL TVDKSRWQQG

NVFSCSVMHE ALHNHYTQKS LSLSPG
```

In this embodiment, the second of the two Fc regions comprises the amino acid sequence set forth below (hinge region italicized; N-linked glycosylation site underlined; CH2 region in regular font; CH3 domain boldened):

```
                                            (SEQ ID NO: 19)
DKTHTCPPCP APELLGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSRDELTK NQVSLTCLVS GFYPSDIAVE

WESNGQPENN YKTTPPILDS DGSFKLYSKL TVDKSRWQQG

NVFSCSVMHE ALHNHYTQKS LSLSPG
```

In another embodiment, one of the two Fc regions comprises the amino acid sequence set forth below (hinge region italicized; the mutated N-linked glycosylation site underlined; CH2 region in regular font; CH3 domain boldened):

```
                                            (SEQ ID NO: 20)
DKTHTCPPCP APELLGGPSV FLFPPKPKDT LMISRTPEVT

CVVVDVSHED PEVKFNWYVD GVEVHNAKTK PREEQYQSTY

RVVSVLTVLH QDWLNGKEYK CKVSNKALPA PIEKTISKAK

GQPREPQVYT LPPSRDELTK NQVKLTCLVK GFYPSDIAVE

WESNGQPENN YKTTPPVLDS DGSFFLYSLL TVDKSRWQQG

NVFSCSVMHE ALHNHYTQKS LSLSPG
```

In this embodiment, the second of the two Fc regions comprises the amino acid sequence set forth below (hinge region italicized; CH2 region in regular font with the mutated N-linked glycosylation site of the CH2 domain underlined; CH3 domain boldened):

```
                                            (SEQ ID NO: 21)
DKTHTCPPCP APELLGGPSV FLFPPKPKDT LMISRTPEVT

CVVVDVSHED PEVKFNWYVD GVEVHNAKTK PREEQYQSTY

RVVSVLTVLH QDWLNGKEYK CKVSNKALPA PIEKTISKAK

GQPREPQVYT LPPSRDELTK NQVSLTCLVS GFYPSDIAVE

WESNGQPENN YKTTPPILDS DGSFKLYSKL TVDKSRWQQG

NVFSCSVMHE ALHNHYTQKS LSLSPG
```

These Fc regions can include nine or fewer, eight or fewer, seven or fewer, six or fewer, five or fewer, four or fewer, three or fewer, two or fewer, one, two, three, four, five, six, seven eight, or nine amino acid substitutions, insertions, and/or deletions so long as the Fc domains can heterodimerize. The amino acid substitutions may be conservative or non-conservative amino acid substitutions.

Any of the CH3 domains and Fc domains described above can be part of a heavy chain that pairs with the light chains described above that have their CL domains replaced with a CH2E domain (or a CH2M domain). Specifically, the heavy chains can include a second CH2 domain that is directly linked, or linked via an intervening sequence, to a VH domain, wherein the second CH2 domain is a CH2E domain, or a fragment thereof that can dimerize with a CH2E domain. In certain instances, the heavy chains can include a second CH2 domain that is directly linked to or linked via an intervening sequence to a VH domain, wherein the second CH2 domain is a CH2M domain, or a fragment thereof that can dimerize with a CH2M domain. Any of the CH3 domains and Fc domains described above can also be part of a heavy chain that pairs with the light chains described above that have the CH1 and CL domains. In certain instances, any of the CH3 domains and Fc domains described above are part of a first heavy chain that pairs with the light chains described above that have their CL domains replaced with a CH2E domain (or a CH2M domain) and any of the CH3 domains and Fc domains described above are part of a second heavy chain that pairs with the light chains described above that include the CH1 and CL domains.

In one embodiment, the heavy chain comprises the following amino acid sequence:

```
                                                          (SEQ ID NO: 22)
ASTKGPTVKI LQSICDGGGH FPPTIQLLCL VSGYTPGTIQ ITWLEDGQVM DVDLSTASTT

QEGELASTQS ELTLSQKHWL SDRTYTCQVT YQGHTFEDST KKCASDKTHT CPPCPAPELL

GGPSVFLFPP KPKDTLMISR TPEVTCVVVD VSHEDPEVKF NWYVDGVEVH NAKTKPREEQ

YQSTYRVVSV LTVLHQDWLN GKEYKCKVSN KALPAPIEKT ISKAKGQPRE PQVYTLPPSR

DELTKNQVAI TCLVKGFYPS DIAVEWESNG QPENNYKTTP PVLDSDGSFF LYSILTVDKS

RWQQGNVFSC SVMHEALHNH YTQKSLSLSP G
```

In one embodiment, this heavy chain heterodimerizes with a light chain comprising the following amino acid sequence:

```
                                                          (SEQ ID NO: 6)
RTVAAPTVKI LQSSCDGGGH FPPTIQLLCL VSGYTPGTIQ

ITWLEDGQVM DVDLSTASTT QEGELASTQS ELTLSQKHWL

SDRTYTCQVT YQGHTFEDSG KKCA
```

These heavy and light chain sequences can each include nine or fewer, eight or fewer, seven or fewer, six or fewer, five or fewer, four or fewer, three or fewer, two or fewer, one, two, three, four, five, six, seven eight, or nine amino acid substitutions, insertions, and/or deletions so long as the heavy and light chains can heterodimerize. The amino acid substitutions may be conservative or non-conservative amino acid substitutions.

In some embodiments, the CH3 domains and Fc domains described above that heterodimerize can be part of a monovalent antibody. The monovalent antibody comprises an Fab that is linked directly or via an intervening linker sequence to one of the two Fc regions of the antibody; the other Fc region does not have an Fab region attached to it.

In other embodiments, the CH3 domains and Fc domains described above that heterodimerize can be part of a single chain Fc (scFc). In certain instances, the CH1 or CL domains of an Fab are linked directly or via an intervening linker to a first Fc region and the Fc region is linked to the second Fc region (e.g., the C-terminus of the CH3 domain of the first Fc region is linked to the N-terminus of the hinge region of the second Fc region).

In certain embodiments, the Fc domains described above that heterodimerize are directly linked, or linked via linker to an Fab. That is, the VH/CH1 containing part of the Fab is linked via its C-terminus to the N-terminus of the hinge region of a first Fc and the VL/CL containing part of the Fab is linked via its C-terminus to the N-terminus of the hinge region of a second Fc region.

In yet other embodiments, the CH3 domains and Fc domains described above that heterodimerize are part of an antibody comprising a first heavy chain and a second heavy chain, wherein the first and second heavy chains pair with a common light chain.

Nucleic Acids

This disclosure also encompasses nucleic acids encoding the heavy and light chains of the heterodimeric bispecific and monovalent antibodies described herein. Many nucleic acid sequences encoding immunoglobulin regions including the VH, VL, hinge, CH1, CH2, CH3, and CH4 regions are known in the art. See, e.g., Kabat et al. in SEQUENCES OF IMMUNOLOGICAL INTEREST, Public Health Service N.I.H., Bethesda, Md., 1991. Using the guidance provided herein, one of skill in the art could combine such nucleic acid sequences and/or other nucleic acid sequence known in the art to create nucleic acid sequences encoding the heterodimeric bispecific antibodies described herein.

In addition, nucleic acid sequences encoding heterodimeric bispecific antibodies described herein can be determined by one of skill in the art based on the amino acid sequences provided herein and knowledge in the art. Besides more traditional methods of producing cloned DNA segments encoding a particular amino acid sequence, companies now routinely produce chemically synthesized, genesized DNAs of any desired sequence to order, thus streamlining the process of producing such DNAs.

Methods of Making Bispecific Antibodies

The bispecific and monovalent antibodies described herein can be made using methods well known in the art. For example, nucleic acids encoding the four polypeptide chains of a bispecific antibody can be introduced into a host cell by a variety of known methods, e.g., transformation, transfection, electroporation, bombardment with nucleic acid-coated microprojectiles, etc. In some instances, the nucleic acids encoding the bispecific antibody can be inserted into a vector appropriate for expression in the host cells before being introduced into the host cells. Typically, such vectors can contain sequence elements enabling expression of the inserted nucleic acids at the RNA and protein levels. Such vectors are well known in the art, and many are commercially available. The host cells containing the nucleic acids can be cultured under conditions so as to enable the cells to express the nucleic acids. The resulting heterodimeric bispecific antibodies can be collected from the cell mass or the culture medium. Alternatively, the heterodimeric bispecific antibodies can be produced in vivo, for example in plant leaves (see, e.g., Scheller et al., Nature Biotechnol., 19: 573-577 (2001) and references cited therein), bird eggs (see, e.g., Zhu et al. (2005), Nature Biotechnol., 23: 1159-1169 (2005) and references cited therein), or mammalian milk (see, e.g., Laible et al., Reprod. Fertil. Dev. 25(1): 315 (2012)). The isolated antibodies can be formulated as a sterile composition for administration to a human subject.

Several kinds of host cells can be used including, e.g., bacterial cells such as *Escherichia coli* or *Bacillus stearothermophilus*, fungal cells such as *Saccharomyces cerevisiae* or *Pichia pastoris*, insect cells such as lepidopteran insect cells including *Spodoptera frupperda* cells, or mammalian cells such as Chinese hamster ovary (CHO) cells, baby hamster kidney (BHK) cells, monkey kidney cells, HeLa cells, human hepatocellular carcinoma cells, or 293 cells, among many others.

The following are examples of the practice of the invention. They are not to be construed as limiting the scope of the invention in any way.

EXAMPLES

The following examples are provided to better illustrate the claimed invention and are not to be interpreted as

Example 1: Engineering Heavy Chain Heterodimerization

Figure 2:
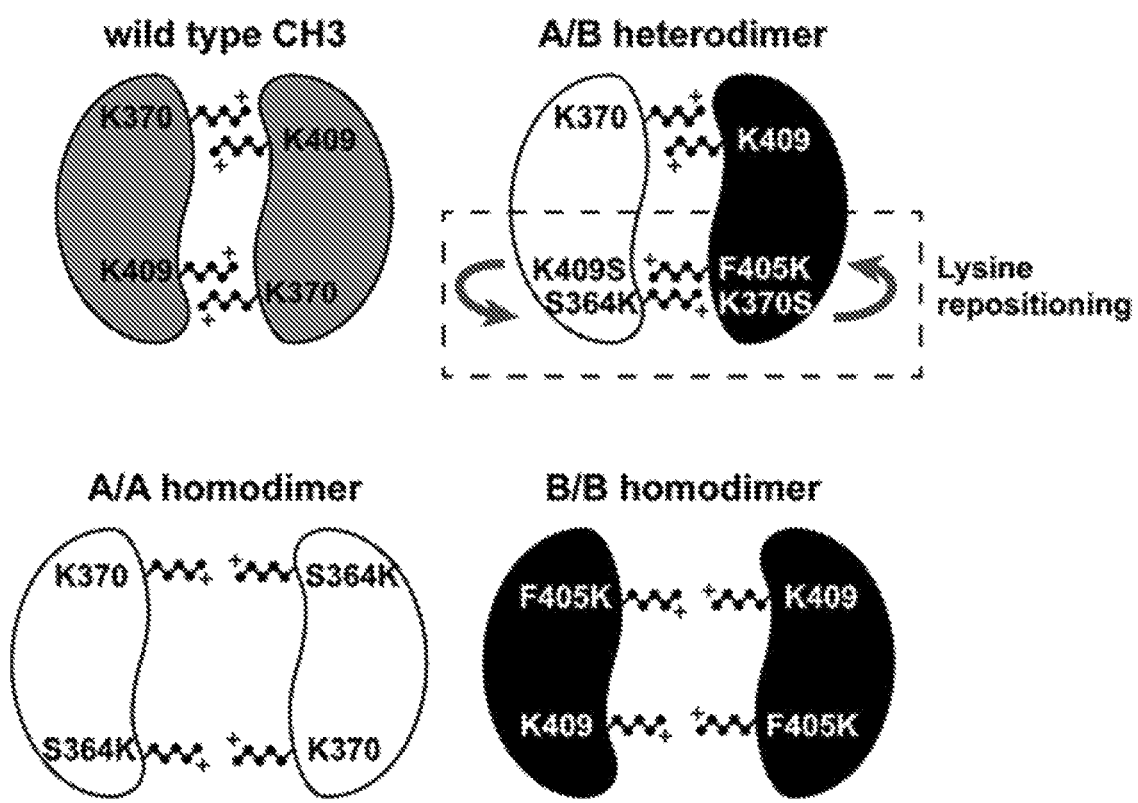
FIG. 2 is a diagrammatic representation of CH3 heterodimerization by lysine repositioning. Lysine 370 and Lysine 409 are stacked in the normal head-to-tail homodimer of wild-type CH3 domains of human IgG1. The mutations S364K/K409S in monomer A and K370S/F405K in monomer B reverse the orientation of the stacked on lysines, enabling the formation of the AB heterodimer but leading to clashes in the homodimers (bottom). Thus, lysine repositioning provides an effective strategy for heavy chain heterodimerization. The amino acid positions referred to above are based on EU numbering.

The CH3 domain is one of the main points of contact between the two heavy chains of an IgG. The two CH3 domains bind each other in a head-to-tail orientation with tight packing of contact residues at the interface. Heavy chain heterodimerization can be achieved by engineering the hydrophobic surface at the core of the contact between the two CH3 domains or by altering charged residues at the perimeter of the contact surface. In order to maintain the tight packing of hydrophobic contact residues, the perimeter of the CH3 interface was chosen for engineering asymmetry. Further design criteria for mutation of the CH3 domains included: (i) efficient drivers of heterodimerization; (ii) few mutations; and (iii) overall charge-neutral changes. Structural analysis of the CH3 domain and design of mutations was done using a crystal structure of human IgG1 Fc (PDB code 3AVE). A comparative analysis has shown high identity between multiple published structures of human Fc domains suggesting the choice of structure may not be critical for engineering the CH3. Based on modeling and analysis of potential interface mutations, a strategy of lysine repositioning was devised to engineer asymmetric complementary CH3 interfaces (FIG. 2). Substitution of Lys409 (EU numbering) with Ser and Ser364 (EU numbering) with Lys in monomer A repositions the Lysine from β-strand E to the adjacent antiparallel β-strand B. Conversely, substitution of Lys370 (EU numbering) with Ser and Phe405 (EU numbering) with Lys in monomer B repositions the Lysine from β-strand B to β-strand E. The repositioned lysines are stacked in the heterodimer, but impose steric and charge clashes in the homodimers, which should prevent their formation, and therefore drive heterodimerization.

To experimentally test the effectiveness of the heterodimerization by lysine repositioning, test antibodies were constructed as mono-mAbs, where one side is a full human IgG1 heavy chain and the other is a free Fc without Fab. The resulting heterodimer can easily be distinguished from the homodimers due to the significant difference in molecular weight, and heterodimerization can be evaluated by separation on SDS-PAGE. The anti-EGFR antibody M60-A02 was used in these test constructs. The mutations in the CH3 domains were generated by PCR-based mutagenesis using the primers listed in Table 1.

TABLE 1

Primers for generating the CH3 mutations S364K/K409S and K370S/F405K in human IgG1 by overlapping PCR.

| PCR | | forward primer | | reverse primer |
|---|---|---|---|---|
| S364K 5' | CO2-966 | TGGGCTGCCTGGTCAAG (SEQ ID NO: 23) | CO2-968 | gtcagTTTgacctggttcttg (SEQ ID NO: 24) |
| S364K 3' | CO2-967 | caagaaccaggtcAAActgac (SEQ ID NO: 25) | AV1-177 | GAATTGGCCGCCCTAGATG (SEQ ID NO: 26) |
| K409S 5' | CO2-966 | TGGGCTGCCTGGTCAAG (SEQ ID NO: 27) | CO2-972 | ggtgagGCTgctgtagagGA (SEQ ID NO: 28) |
| K409S 3' | CO2-971 | TCctctacagcAGCctcacc (SEQ ID NO: 29) | AV1-177 | GAATTGGCCGCCCTAGATG (SEQ ID NO: 30) |
| K370S 5' | CO2-548 | GCTCTGGGTTCCAGGTTC (SEQ ID NO: 31) | CO2-970 | gatagaagccGCTgaccagg (SEQ ID NO: 32) |
| K370S 3' | CO2-969 | cctggtcAGCggcttctatc (SEQ ID NO: 33) | AV1-177 | GAATTGGCCGCCCTAGATG (SEQ ID NO: 34) |
| F405K 5' | CO2-548 | GCTCTGGGTTCCAGGTTC (SEQ ID NO: 35) | CO2-974 | tgtagagTTTgaaggagccgt (SEQ ID NO: 36) |
| F403K 3' | CO2-973 | acggctccttcAAActctaca (SEQ ID NO: 37) | AV1-177 | GAATTGGCCGCCCTAGATG (SEQ ID NO: 38) |

The amplification was carried out using Q5 Hot Start High-Fidelity DNA Polymerase (NEB #M0493L), and the PCR products were used with the HiFi Gibson assembly kit (SGI #GA1100-50) to build the constructs.

In order the gain some insight into the individual effects of the repositioned lysines, constructs with individual mutations were built as well. These half-designs were named MP1 and MP2, respectively (Table 2).

TABLE 2

Constructs for testing Fc heterodimerization.

| Protein | Monomer A (anti-EGFR M60-A02) | | | Monomer B (human IgG1 Fc) | | |
|---|---|---|---|---|---|---|
| MP1 | pMP233 | M60-A02 mp1a | S364K | pMP234 | Fc mp1b | K370S |
| MP2 | pMP235 | M60-A02 mp2a | K409S | pMP236 | Fc mp2b | F405K |

TABLE 2-continued

Constructs for testing Fc heterodimerization.

| Protein | Monomer A (anti-EGFR M60-A02) | | | Monomer B (human IgG1 Fc) | | |
|---|---|---|---|---|---|---|
| MP3 | pMP237 | M60-A02 mp3a | S364K/K409S | pMP238 | Fc mp3b | K370S/F405K |
| MP4 | pMP254 | M60-A02 mp4a | S364K/K409L | pMP259 | Fc mp4b | K370S/V397I/F405K |
| ZW1 | pMP205 | M60-A02 zw1a | T350V/L351Y/F405A/T407V | pMP208 | Fc mzw1b | T350V/T366L/K392L/T394W |
| Knobs/Holes | pMP209 | M60-A02 hole | T366S/L368A/Y407V | pMP212 | Fc knob | T366W |
| electrost. steering | pMP213 | M60-A02 KD | K409D | pMP216 | Fc DK | D399K |
| wt IgG1 | pMP221 | M60-A02 wt IgG1 | none | pMP222 | Fc wt hu IgG1 | none |

The complete design has both lysines repositioned (pMP237 has the mutations S364K/K409S, and pMP238 has K370S/F405K) and should be most effective in driving heterodimerization. This design was named MP3. The peptide sequences of the CH3 domains of MP3 are shown below:

```
Amino Acid Sequence of the CH3 domain MP3
Monomer A (mutations are bold and underlined)
                                                            (SEQ ID NO: 39)
  1 GQPREPQVYT LPPSRDELTK NQVKLTCLVK GFYPSDIAVE WESNGQPENN YKTTPPVLDS

61 DGSFFLYSSL TVDKSRWQQG NVFSCSVMHE ALHNHYTQKS LSLSPG

Amino Acid Sequence of the CH3 domain MP3
Monomer B (mutations are bold and underlined)
                                                            (SEQ ID NO: 40)
  1 GQPREPQVYT LPPSRDELTK NQVSLTCLVS GFYPSDIAVE WESNGQPENN YKTTPPVLDS

61 DGSFKLYSKL TVDKSRWQQG NVFSCSVMHE ALHNHYTQKS LSLSPG
```

Additionally, several published CH3 heterodimerization mutations were generated for comparison (Atwell et al., *J. Mol. Biol.*, 270:26-35, 1997; Gunasekaran et al., *J. Biol. Chem.*, 285:19637-19646, 2010; Von Kreudenstein et al., mAbs 5:646-654, 2013). Furthermore, the constructs pMP221 and pMP222 were built to represent a wild-type IgG1 control. All constructs that were generated for this initial test of heterodimerization are summarized in Table 2, and all plasmids were verified by DNA sequencing.

Figure 3A:
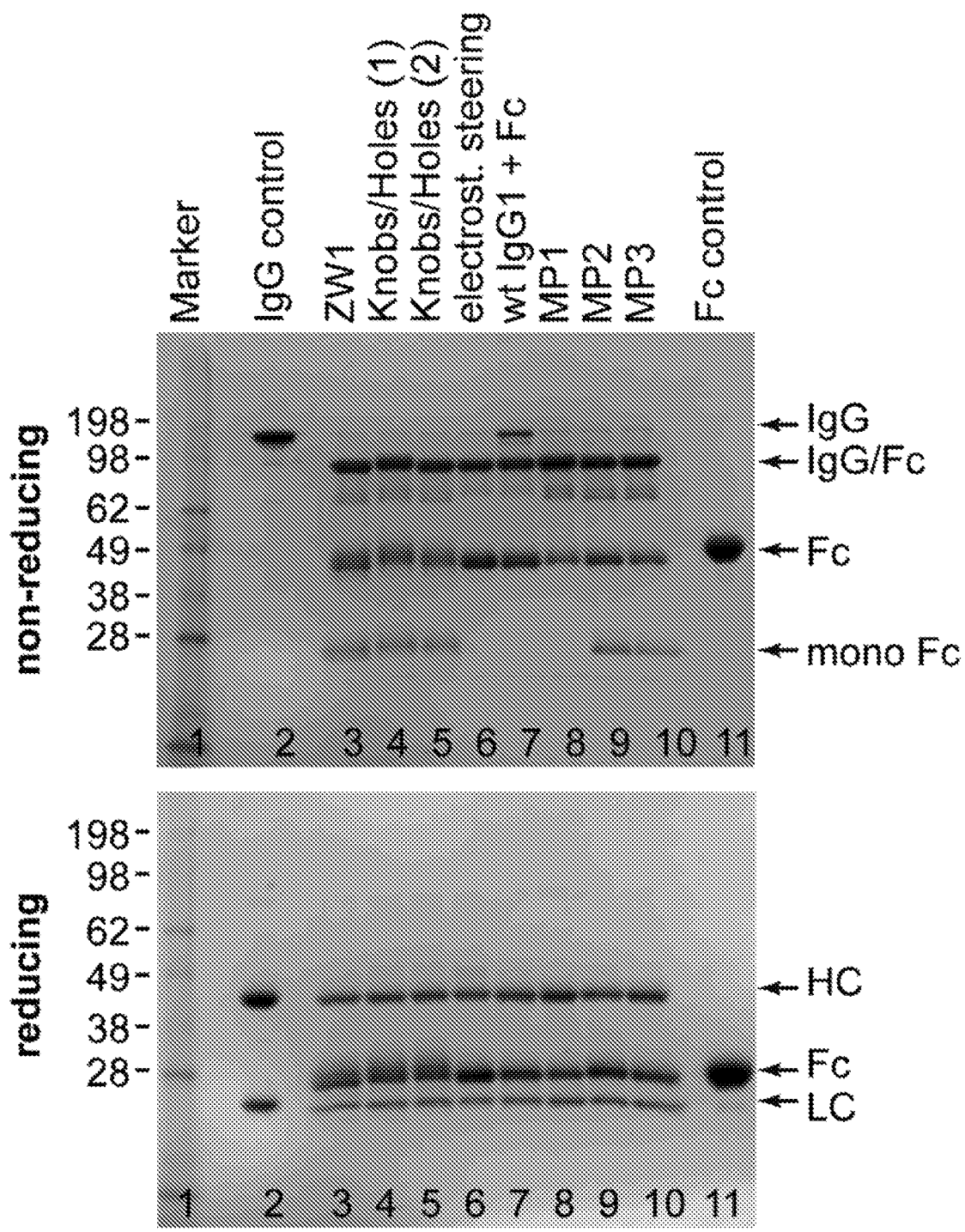
FIG. 3A is a depiction of SDS-PAGE analysis of IgG/Fc heterodimers. Aliquots of protein A-purified heterodimers were analyzed by SDS page. The heterodimer between IgG1 and Fc is the predominant species. Two fractions of Knobs-into-Holes were loaded. The half-design MP1 shows high amount of heterodimer, but lacks mutations to prevent formation of the Fc dimer and thus contains no Fc monomer.

The antibodies were expressed in CHO cells by transient transfection. All antibodies expressed well, producing titers between 100 and 200 mg/L after 9 days expression using CHO cells transfected at 6×10$^6$ cells/ml with Fectopro and DNA at a 2:1 ratio and temperature shift to 28° C. the next day. Supernatants were purified on a protein A column and aliquots were analyzed by SDS-PAGE (FIG. 3A). The heterodimer of IgG1 heavy chain and free Fc was predominantly found in all samples. In addition, the co-transfection of wild-type IgG1 and Fc also produced strong bands corresponding to both homodimers. These bands were significantly weaker in the published mutants and all lysine repositioning mutants. Thus, lysine repositioning and published mutations drive the formation of heavy chain heterodimers and reduce homodimerization. The protein A-purified material was further analyzed by mass spectrometry and the relative amounts of major components estimated. The amount of heterodimer in the samples ranged from 35% to 80%, being slightly higher in the lysine repositioning mutants MP1, MP2 and MP3 than in published designs (FIG. 3B). However, varying expression levels of the individual chains may influence these results making direct comparisons difficult. Importantly, the designs MP2 and MP3 as well as ZW1 and Knobs-into-holes mutations all contained monomeric Fc. The presence of monomeric Fc demonstrates that Fc dimers are destabilized by the mutations in CH3, and are therefore less like to form. Altogether, these results show that lysine repositioning is an efficient heavy chain heterodimerization strategy, which prevents homodimerization as efficiently as several published mutations.

After this initial testing, additional structural modeling was done to identify mutations that could improve the packing of interface residues. Such mutations could potentially increase the efficiency of heterodimerization or the stability of dimers, and would therefore be beneficial. Two changes were identified that could improve the original lysine repositioning design MP3. This new design was named MP4 and the amino acid changes are shown in Table 2. IgG1/Fc heterodimers with the MP4 mutations were expressed in CHO cells as described above and purified from supernatants by Protein A. Mass spectrometry analysis demonstrated that MP4 produced heterodimers between the IgG1 heavy chain and the free Fc as efficiently as MP3 (FIG. 3B).

All heterodimeric proteins were further purified on KappaSelect columns to remove the Fc dimers and monomers, followed by a polishing step on Tandem Superdex S200. This three-step purification yielded relatively pure heterodimers that were used for differential scanning calorimetry (DSC) to determine melting temperatures. The wild type IgG1 control showed the expected Tm of the CH3 domain of ~83° C. (FIG. 3C). The ZW1 design has a similar CH3 melting temperature (FIG. 3C), as it was extensively engineered in an iterative process to regain the thermal stability of wild type IgG1 (Von Kreudenstein et al., mAbs 5:646-654, 2013). The knobs-into-holes and electrostatic steering comparator molecules showed only one peak in DSC profiles, suggesting that the Tm of the CH3 domain is decreased to ~70° C. and the domain is melting with the CH2 and Fab domains, producing the single peak on DSC (FIG. 3C). The MP3 molecule showed only one peak at ~70° C. in DSC profiles as well, indicating the Tm of CH3 has similarly dropped (FIG. 3C). The proteins MP4 and MP4a3b (MP4 Monomer A and MP3 Monomer B) showed a shoulder on the right of the CH2/Fab peak (FIG. 3C), suggesting the mutation K409L confers slightly increased stability over the original mutation K409S, and that it may be possible to improve the Tm by further engineering. Nevertheless, the design MP4 has a decreased Tm compared to a wild-type IgG1 CH3 domain.

The peptide sequences of the CH3 domains of MP4 are shown below:

```
Sequence of the CH3 domain MP4 Monomer A
(mutations are bold and underlined)
                                                      (SEQ ID NO: 41)
  1 GQPREPQVYT LPPSRDELTK NQVKLTCLVK GFYPSDIAVE WESNGQPENN YKTTPPVLDS

61 DGSFFLYSLL TVDKSRWQQG NVFSCSVMHE ALHNHYTQKS LSLSPG

Sequence of the CH3 domain MP4 Monomer B
(mutations are bold and underlined)
                                                      (SEQ ID NO: 42)
  1 GQPREPQVYT LPPSRDELTK NQVSLTCLVS GFYPSDIAVE WESNGQPENN YKTTPPILDS

61 DGSFKLYSKL TVDKSRWQQG NVFSCSVMHE ALHNHYTQKS LSLSPG
```

The DNA sequences of the plasmids (pMP254 and pMP259) encoding MP4 are provided below:
DNA sequence of pMP254, anti-EGFRM60-A02 IgG1 heavy chain with MP4A mutations (S634K, K409L):

```
DNA sequence of pMP254, anti-EGFR M60-A02 IgG1
heavy chain with MP4A mutations (S634K, K409L):
                                                      (SEQ ID NO: 43)
    1 agcttgacat tgattattga ctagttatta atagtaatca attacggggt cattagttca 61 tagcccatat atggagttcc gcgttacata acttacggta aatggcccgc ctggctgacc 121 gcccaacgac ccccgcccat tgacgtcaat aatgacgtat gttcccatag taacgccaat 181 agggactttc cattgacgtc aatgggtgga gtatttacgg taaactgccc acttggcagt 241 acatcaagtg tatcatatgc caagtacgcc ccctattgac gtcaatgacg gtaaatggcc 301 cgcctggcat tatgcccagt acatgacctt atgggacttt cctacttggc agtacatcta 361 cgtattagtc atcgctatta ccatggtgat gcggttttgg cagtacatca atgggcgtgg 421 atagcggttt gactcacggg gatttccaag tctccacccc attgacgtca atgggagttt 481 gttttggcac caaaatcaac gggactttcc aaaatgtcgt aacaactccg ccccattgac 541 gcaaatgggc ggtaggcgtg tacggtggga ggtctatata agcagagctc gtttagtgaa 601 ccgtcagatc gcctggagac gccatccacg ctgttttgac ctccataaga gaccaccggga 661 ccgatccagc ctccgcggcc gggaacggtg cattggaacg cggattcccc gtgccaagag 721 tgacgtaagt accgcctata gagtctatag gcccacccc ttggcttctt atgcatgcta 781 tactgttttt ggcttggggt ctatacaccc ccgcttcctc atgttatagg tgatggtata 841 gcttagccta taggtgtggg ttattgacca ttattgacca ctccccctatt ggtgacgata 901 ctttccatta ctaatccata acatggctct ttgccacaac tctctttatt ggctatatgc 961 caatacactg tccttcgag actgacacgg actctgtatt tttacaggat ggggtctcat 1021 ttattattta caaattcaca tatacaacac caccgtcccc agtgcccgca gttttttatta 1081 aacataacgt gggatctcca cgcgaatctc gggtacgtgt tccggaacgg tggagggcag 1141 tgtagtctga gcagtactcg ttgctgccgc gcgcgccacc agacataata gctgacagac 1201 taacagactg ttcctttcca tgggtctttt ctgcagtcac cgtccttgac acgggatccg 1261 cggccgccac cATGGGTTGG AGCCTCATCT TGCTCTTCCT TGTCGCTGTT GCTACGCGTG

1321 TCCTGTCCGA GGTGCAGCTG TTGGAGTCTG GGGGAGGCTT GGTCCAGCCT GGGGGGTCCC

1381 TGAGACTCTC CTGTGCAGCC TCTGGATTCA CCTTCAGTGA CTATATTATG CACTGGGTCC
```

```
1441 GCCAGGCTCC AGGGAAGGGG CTGGAGTGGG TCTCAGTTAT TAGTAGTTCT GGTGGCGACA

1501 CATCCTACGC AGACTCCGTG AAGGGCCGAT TCACCATCTC CAGAGACAAT TCCAAGAACA

1561 CGCTGTATCT GCAAATGAAC AGCCTGAGAG CCGAGGACAC GGCCGTGTAT TACTGTGCGA

1621 AAGTCCTCGC GGGTTACTTC GACTGGTTAC CCTTTGACTA CTGGGGCCAG GGAACCCTGG

1681 TCACCGTCTC GAGCGCCTCC ACCAAGGGCC CATCGGTCTT CCCCCTGGCA CCCTCCTCCA

1741 AGAGCACCTC TGGGGGCACA GCGGCCCTGG GCTGCCTGGT CAAGGACTAC TTCCCCGAAC

1801 CGGTGACGGT GTCGTGGAAC TCAGGCGCCC TGACCAGCGG CGTGCACACC TTCCCGGCTG

1861 TCCTACAGTC CTCAGGACTC TACTCCCTCA GCAGCGTGGT GACCGTGCCC TCCAGCAGCT

1921 TGGGCACCCA GACCTACATC TGCAACGTGA ATCACAAGCC CAGCAACACC AAGGTGGACA

1981 AGAAAGTTGA GCCCAAATCT TGTGACAAGA CTCACACATG CCCACCGTGC CCAGCACCTG

2041 AACTCCTGGG GGGACCGTCA GTCTTCCTCT TCCCCCCAAA ACCCAAGGAC ACCCTCATGA

2101 TCTCCCGGAC CCCTGAGGTC ACATGCGTGG TGGTGGACGT GAGCCACGAA GACCCTGAGG

2161 TCAAGTTCAA CTGGTACGTG GACGGCGTGG AGGTGCATAA TGCCAAGACA AAGCCGCGGG

2221 AGGAGCAGTA CAACAGCACG TACCGTGTGG TCAGCGTCCT CACCGTCCTG CACCAGGACT

2281 GGCTGAATGG CAAGGAGTAC AAGTGCAAGG TCTCCAACAA AGCCCTCCCA GCCCCCATCG

2341 AGAAAACCAT CTCCAAAGCC AAAGGGCAGC CCCGAGAACC ACAGGTGTAC ACCCTGCCCC

2401 CATCCCGGGA TGAGCTGACC AAGAACCAGG TCAAACTGAC CTGCCTGGTC AAAGGCTTCT

2461 ATCCCAGCGA CATCGCCGTG GAGTGGGAGA GCAATGGGCA GCCGGAGAAC AACTACAAGA

2521 CCACGCCTCC CGTGTTGGAC TCCGACGGCT CCTTCTTCCT CTACAGCCTC CTCACCGTGG

2581 ACAAGAGCAG GTGGCAGCAG GGGAACGTCT TCTCATGCTC CGTGATGCAT GAGGCTCTGC

2641 ACAACCACTA CACGCAGAAG AGCCTCTCCC TGTCTCCGGG TTAGtaatta attaatgcat 2701 ctagggcggc caattccgcc cctctccctc ccccccccct aacgttactg gccgaagccg 2761 cttggaataa ggccggtgtg cgtttgtcta tatgtgattt tccaccatat tgccgtcttt 2821 tggcaatgtg agggcccgga aacctggccc tgtcttcttg acgagcattc ctaggggtct 2881 ttccctctc gccaaaggaa tgcaaggtct gttgaatgtc gtgaaggaag cagttcctct 2941 ggaagcttct tgaagacaaa caacgtctgt agcgaccctt gcaggcagc ggaaccccc 3001 acctggcgac aggtgcctct gcggccaaaa gccacgtgta taagatacac ctgcaaaggc 3061 ggcacaaccc cagtgccacg ttgtgagttg gatagttgtg gaaagagtca aatggctctc 3121 ctcaagcgta ttcaacaagg ggctgaagga tgcccagaag gtaccccatt gtatgggatc 3181 tgatctgggg cctcggtgca catgctttac atgtgtttag tcgaggttaa aaaaacgtct 3241 aggccccccg aaccacgggg acgtggtttt cctttgaaaa acacgatgat aagcttgcca 3301 caagctagca tggttcgacc attgaactgc atcgtcgccg tgtcccaaaa tatggggatt 3361 ggcaagaacg gagacctacc ctggcctccg ctcaggaacg agttcaagta cttccaaaga 3421 atgaccacaa cctcttcagt ggaaggtaaa cagaatctgg tgattatggg taggaaaacc 3481 tggttctcca ttcctgagaa gaatcgacct ttaaaggaca gaattaatat agttctcagt 3541 agagaactca aagaaccacc acgaggagct cattttcttg ccaaaagttt ggatgatgcc 3601 ttaagactta ttgaacaacc ggaattggca agtaaagtag acatggtttg gatagtcgga 3661 ggcagttctg tttaccagga agccatgaat caaccaggcc acctcagact ctttgtgaca 3721 aggatcatgc aggaatttga aagtgacacg ttttcccag aaattgattt ggggaaatat 3781 aaacttctcc cagaataccc aggcgtcctc tctgaggtcc aggaggaaaa aggcatcaag 3841 tataagtttg aagtctacga gaagaaagac taatcgagaa ttgtctagac tgcccgggtg
```

-continued

```
3901 gcatccctgt gacccctccc cagtgcctct cctggtcgtg aaggtgctca ctccagtgcc
3961 caccagcctt gtcctaataa aattaagttg catcattttg tttgactagg tgtccttgta
4021 taatattatg gggtggaggc gggtggtatg gagcaagggg caggttggga agacaacctg
4081 tagggccttc agggtctatt gggaaccagg ctggagtgca gtggcacgat cttggctcgc
4141 tgcaatctcc gcctcctggg ttcaagcgat tctcctgcct cagtctcccg aatagttggg
4201 attccaggca tgcacgacca ggctcagcta attttgtat ttttggtaga gacggggttt
4261 caccatattg gccagtctgg tctccatctc ctgacctcag gtaatccgcc cgcctcggcc
4321 tcccaaattg ctgggattac aggtatgagc cactgggccc ttccctgtcc tgtgatttta
4381 aaataattat accagcagaa ggacgtccag acacagcatg gctacctgg ccatgcccag
4441 ccagttggac atttgagttg tttgcttggc actgtcctct catcaattca ctggccgtcg
4501 ttttacaacg tcgtgactgg gaaaaccctg gcgttaccca acttaatcgc cttgcagcac
4561 atccccttt cgccagctgg cgtaatagcg aagaggcccg caccgatcgc ccttcccaac
4621 agttgcgcag cctgaatggc gaatggcgcc tgatgcggta ttttctcctt acgcatctgt
4681 gcggtatttc acaccgcata tggtgcactc tcagtacaat ctgctctgat gccgcatagt
4741 taagccagcc ccgacacccg ccaacacccg ctgacgcgcc ctgacgggct tgtctgctcc
4801 cggcatccgc ttacagacaa gctgtgaccg tctccgggag ctgcatgtgt cagaggtttt
4861 caccgtcatc accgaaacgc gcgagacgaa agggcctcgt gatacgccta ttttatagg
4921 ttaatgtcat gataataatg gtttcttaga cgtcaggtgg cacttttcgg ggaaatgtgc
4981 gcggaacccc tatttgttta ttttctaaa tacattcaaa tatgtatccg ctcatgagac
5041 aataaccctg ataaatgctt caataatatt gaaaaaggaa gagtatgagt attcaacatt
5101 tccgtgtcgc ccttattccc ttttttgcgg cattttgcct tcctgttttt gctcacccag
5161 aaacgctggt gaaagtaaaa gatgctgaag atcagttggg tgcacgagtg ggttacatcg
5221 aactggatct caacagcggt aagatccttg agagttttcg ccccgaagaa cgttttccaa
5281 tgatgagcac ttttaaagtt ctgctatgtg gcgcggtatt atcccgtatt gacgccgggc
5341 aagagcaact cggtcgccgc atacactatt ctcagaatga cttggttgag tactcaccag
5401 tcacagaaaa gcatcttacg gatggcatga cagtaagaga attatgcagt gctgccataa
5461 ccatgagtga taacactgcg gccaacttac ttctgacaac gatcggagga ccgaaggagc
5521 taaccgcttt tttgcacaac atgggggatc atgtaactcg ccttgatcgt tgggaaccgg
5581 agctgaatga agccatacca aacgacgagc gtgacaccac gatgcctgta gcaatggcaa
5641 caacgttgcg caaactatta actggcgaac tacttactct agcttcccgg caacaattaa
5701 tagactggat ggaggcggat aaagttgcag gaccacttct gcgctcggcc cttccggctg
5761 gctggtttat tgctgataaa tctggagccg gtgagcgtgg gtctcgcggt atcattgcag
5821 cactggggcc agatggtaag ccctcccgta tcgtagttat ctacacgacg gggagtcagg
5881 caactatgga tgaacgaaat agacagatcg ctgagatagg tgcctcactg attaagcatt
5941 ggtaactgtc agaccaagtt tactcatata cttttagat tgatttaaaa cttcattttt
6001 aatttaaaag gatctaggtg aagatccttt ttgataatct catgaccaaa atcccttaac
6061 gtgagttttc gttccactga gcgtcagacc ccgtagaaaa gatcaaagga tcttcttgag
6121 atccttttt tctgcgcgta atctgctgct tgcaaacaaa aaaaccaccg ctaccagcgg
6181 tggtttgttt gccggatcaa gagctaccaa ctctttttcc gaaggtaact ggcttcagca
6241 gagcgcagat accaaatact gttcttctag tgtagccgta gttaggccac cacttcaaga
```

-continued

```
6301 actctgtagc accgcctaca tacctcgctc tgctaatcct gttaccagtg gctgctgcca 6361 gtggcgataa gtcgtgtctt accgggttgg actcaagacg atagttaccg gataaggcgc 6421 agcggtcggg ctgaacgggg ggttcgtgca cacagcccag cttggagcga acgacctaca 6481 ccgaactgag atacctacag cgtgagctat gagaaagcgc cacgcttccc gaagggagaa 6541 aggcggacag gtatccggta agcggcaggg tcggaacagg agagcgcacg agggagcttc 6601 caggggggaaa cgcctggtat ctttatagtc ctgtcgggtt tcgccacctc tgacttgagc 6661 gtcgattttt gtgatgctcg tcaggggggc ggagcctatg gaaaaacgcc agcaacgcgg 6721 ccttttttacg gttcctggcc ttttgctggc cttttgctca catgttcttt cctgcgttat 6781 cccctgattc tgtggataac cgtattaccg cctttgagtg agctgatacc gctcgccgca 6841 gccgaacgac cgagcgcagc gagtcagtga gcgaggaagc ggaagagcgc ccaatacgca 6901 aaccgcctct ccccgcgcgt tggccgattc attaatgcag ctggcacgac aggtttcccg 6961 actggaaagc gggcagtgag cgcaacgcaa ttaatgtgag ttagctcact cattaggcac 7021 cccaggcttt acactttatg cttccggctc gtatgttgtg tggaattgtg agcggataac 7081 aatttcacac aggaaacagc tatgaccatg attacgcca
```

DNA Sequence of pMP259, IgG1 Fc with MP4B mutations
(K370S, V397I, F405K):

(SEQ ID NO: 44)

```
   1 agcttgacat tgattattga ctagttatta atagtaatca attacggggt cattagttca 61 tagcccatat atggagttcc gcgttacata acttacggta aatggcccgc ctggctgacc 121 gcccaacgac ccccgcccat tgacgtcaat aatgacgtat gttcccatag taacgccaat 181 agggactttc cattgacgtc aatgggtgga gtatttacgg taaactgccc acttggcagt 241 acatcaagtg tatcatatgc caagtacgcc ccctattgac gtcaatgacg gtaaatggcc 301 cgcctggcat tatgcccagt acatgacctt atgggacttt cctacttggc agtacatcta 361 cgtattagtc atcgctatta ccatggtgat gcggttttgg cagtacatca atgggcgtgg 421 atagcggttt gactcacggg gatttccaag tctccacccc attgacgtca atgggagttt 481 gttttggcac caaaatcaac gggactttcc aaaatgtcgt aacaactccg ccccattgac 541 gcaaatgggc ggtaggcgtg tacggtggga ggtctatata agcagagctc gtttagtgaa 601 ccgtcagatc gcctggagac gccatccacg ctgttttgac ctccatagaa gacaccggga 661 ccgatccagc ctccgcggcc gggaacggtg cattggaacg cggattcccc gtgccaagag 721 tgacgtaagt accgcctata gagtctatag gcccaccccc ttggcttctt atgcatgcta 781 tactgttttt ggcttggggt ctatacaccc ccgcttcctc atgttatagg tgatggtata 841 gcttagccta taggtgtggg ttattgacca ttattgacca ctcccctatt ggtgacgata 901 ctttccatta ctaatccata acatggctct ttgccacaac tctctttatt ggctatatgc 961 caatacactg tccttcagag actgacacgg actctgtatt tttacaggat ggggtctcat 1021 ttattattta caaattcaca tatacaacac caccgtcccc agtgcccgca gttttttatta 1081 aacataacgt gggatctcca cgcgaatctc gggtacgtgt tccggaacgg tggagggcag 1141 tgtagtctga gcagtactcg ttgctgccgc gcgcgccacc agacataata gctgacagac 1201 taacagactg ttccttttcca tgggtctttt ctgcagtcac cgtccttgac acgggatccg 1261 cggccgccAT GGAGACAGAC ACACTCCTGC TATGGGTACT GCTGCTCTGG GTTCCAGGTT 1321 CCAccggTGA CAAGACTCAC ACATGCCCAC CGTGCCCAGC ACCTGAACTC CTGGGGGGAC

1381 CGTCAGTCTT CCTCTTCCCC CCAAAACCCA AGGACACCCT CATGATCTCC CGGACCCCTG

1441 AGGTCACATG CGTGGTGGTG GACGTGAGCC ACGAAGACCC TGAGGTCAAG TTCAACTGGT
```

```
1501 ACGTGGACGG CGTGGAGGTG CATAATGCCA AGACAAAGCC GCGGGAGGAG CAGTACAACA
1561 GCACGTACCG TGTGGTCAGC GTCCTCACCG TCCTGCACCA GGACTGGCTG AATGGCAAGG
1621 AGTACAAGTG CAAGGTCTCC AACAAAGCCC TCCCAGCCCC CATCGAGAAA ACCATCTCCA
1681 AAGCCAAAGG GCAGCCCCGA GAACCACAGG TGTACACCCT GCCCCATCC CGGGATGAGC
1741 TGACCAAGAA CCAGGTCAGC CTGACCTGCC TGGTCAGCGG CTTCTATCCC AGCGACATCG
1801 CCGTGGAGTG GGAGAGCAAT GGGCAGCCGG AGAACAACTA CAAGACCACG CCTCCCATCT
1861 TGGACTCCGA CGGCTCCTTC AAACTCTACA GCAAGCTCAC CGTGGACAAG AGCAGGTGGC
1921 AGCAGGGGAA CGTCTTCTCA TGCTCCGTGA TGCATGAGGC TCTGCACAAC CACTACACGC
1981 AGAAGAGCCT CTCCCTGTCT CCGGGTTAGt aattaattaa tgcatctagg gcggccaatt
2041 ccgcccctct ccctcccccc ccctaacgt tactggccga agccgcttgg aataaggccg
2101 gtgtgcgttt gtctatatgt tattttccac catattgccg tcttttggca atgtgagggc
2161 ccggaaacct ggccctgtct tcttgacgag cattcctagg gtctttccc ctctcgccaa
2221 aggaatgcaa ggtctgttga atgtcgtgaa ggaagcagtt cctctggaag cttcttgaag
2281 acaaacaacg tctgtagcga cccttttgcag gcagcggaac cccccacctg gcgacaggtg
2341 cctctgcggc caaaagccac gtgtataaga tacacctgca aaggcggcac aaccccagtg
2401 ccacgttgtg agttggatag ttgtggaaag agtcaaatgg ctctcctcaa gcgtattcaa
2461 caagggggctg aaggatgccc agaaggtacc ccattgtatg ggatctgatc tggggcctcg
2521 gtgcacatgc tttacatgtg tttagtcgag gttaaaaaaa cgtctaggcc ccccgaacca
2581 cggggacgtg gttttccttt gaaaaacacg atgataatat ggccacaacc atggttaccg
2641 agtacaagcc cacggtgcgc ctcgccaccc gcgacgacgt cccccagggcc gtacgcaccc
2701 tcgccgccgc gttcgccgac tacccccgcca cgcgccacac cgtcgatccg gaccgccaca
2761 tcgagcgggt caccgagctg caagaactct tcctcacgcg cgtcgggctc gacatcggca
2821 aggtgtgggt cgcggacgac ggcgccgcgg tggcggtctg gaccacgccg agagcgtcg
2881 aagcgggggc ggtgttcgcc gagatcggcc cgcgcatggc cgagttgagc ggttcccggc
2941 tggccgcgca gcaacagatg gaaggcctcc tggcgccgca ccggcccaag gagcccgcgt
3001 ggttcctggc caccgtcggc gtctcgcccg accaccaggg caagggtctg ggcagcgccg
3061 tcgtgctccc cggagtggag gcggccgagc gcgccgggt gcccgccttc ctggagacct
3121 ccgcgccccg caacctcccc ttctacgagc ggctcggctt caccgtcacc gccgacgtcg
3181 aggtgcccga aggaccgcgc acctggtgca tgacccgcaa gccggtgcc tgagtcgatg
3241 ataatcgatt agactgcccg ggtggcatcc ctgtgacccc tccccagtgc ctctcctggt
3301 cgtggaaggt gctactccag tgcccaccag ccttgtccta ataaaattaa gttgcatcat
3361 tttgtttgac taggtgtcct tgtataatat tatgggtgg aggcgggtgg tatggagcaa
3421 ggggcaggtt gggaagacaa cctgtagggc cttcagggtc tattgggaac caggctggag
3481 tgcagtggca cgatcttggc tcgctgcaat ctccgcctcc tgggttcaag cgattctcct
3541 gcctcagtct cccgaatagt tgggattcca ggcatgcacg accaggctca gctaattttt
3601 gtattttgg tagagacggg gtttcaccat attggccagt ctggtatcca tctcctgacc
3661 tcaggtaatc cgcccgcctc ggcctccaa attgctggga ttacaggtat gagccactgg
3721 gccccttccct gtcctgtgat tttaaaataa ttataccagc agaaggacgt ccagacacag
3781 catgggctac ctggccatgc ccagccagtt ggacatttga gttgtttgct tggcactgtc
3841 ctctcatcaa ttcgagctca ctggccgtcg ttttacaacg tcgtgactgg gaaaaccctg
3901 gcgttaccca acttaatcgc cttgcagcac atcccccttt cgccagctgg cgtaatagcg
```

-continued

```
3961 aagaggcccg caccgatcgc ccttcccaac agttgcgcag cctgaatggc gaatggcgcc
4021 tgatgcggta ttttctcctt acgcatctgt gcggtatttc acaccgcata tggtgcactc
4081 tcagtacaat ctgctctgat gccgcatagt taagccagcc ccgacacccg ccaacacccg
4141 ctgacgcgcc ctgacgggct tgtctgctcc cggcatccgc ttacagacaa gctgtgaccg
4201 tctccgggag ctgcatgtgt cagaggtttt caccgtcatc accgaaacgc gcgagacgaa
4261 agggcctcgt gatacgccta ttttttatagg ttaatgtcat gataataatg gtttcttaga
4321 cgtcaggtgg cacttttcgg ggaaatgtgc gcggaacccc tatttgttta ttttctaaa
4381 tacattcaaa tatgtatccg ctcatgagac aataaccctg ataaatgctt caataatatt
4441 gaaaaaggaa gagtatgagt attcaacatt tccgtgtcgc ccttattccc ttttttgcgg
4501 cattttgcct tcctgttttt gctcacccag aaacgctggt gaaagtaaaa gatgctgaag
4561 atcagttggg tgcacgagtg ggttacatcg aactggatct caacagcggt aagatccttg
4621 agagttttcg ccccgaagaa cgttttccaa tgatgagcac ttttaaagtt ctgctatgtg
4681 gcgcggtatt atcccgtatt gacgccgggc aagagcaact cggtcgccgc atacactatt
4741 ctcagaatga cttggttgag tactcaccag tcacagaaaa gcatcttacg gatggcatga
4801 cagtaagaga attatgcagt gctgccataa ccatgagtga taacactgcg gccaacttac
4861 ttctgacaac gatcggagga ccgaaggagc taaccgcttt tttgcacaac atggggatc
4921 atgtaactcg ccttgatcgt tgggaaccgg agctgaatga agccatacca aacgacgagc
4981 gtgacaccac gatgcctgta gcaatggcaa caacgttgcg caaactatta actggcgaac
5041 tacttactct agcttcccgg caacaattaa tagactggat ggaggcggat aaagttgcag
5101 gaccacttct gcgctcggcc cttccggctg gctggtttat tgctgataaa tctggagccg
5161 gtgagcgtgg ttcccgcggt atcattgcag cactggggcc agatggtaag ccctcccgta
5221 tcgtagttat ctacacgacg gggagtcagg caactatgga tgaacgaaat agacagatcg
5281 ctgagatagg tgcctcactg attaagcatt ggtaactgtc agaccaagtt tactcatata
5341 tactttagat tgatttaaaa cttcattttt aatttaaaag gatctaggtg aagatccttt
5401 ttgataatct catgaccaaa atcccttaac gtgagttttc gttccactga gcgtcagacc
5461 ccgtagaaaa gatcaaagga tcttcttgag atcctttttt tctgcgcgta atctgctgct
5521 tgcaaacaaa aaaaccaccg ctaccagcgg tggtttgttt gccggatcaa gagctaccaa
5581 ctctttttcc gaaggtaact ggcttcagca gagcgcagat accaaatact gttcttctag
5641 tgtagccgta gttaggccac cacttcaaga actctgtagc accgcctaca tacctcgctc
5701 tgctaatcct gttaccagtg gctgctgcca gtggcgataa gtcgtgtctt accgggttgg
5761 actcaagacg atagttaccg gataaggcgc agcggtcggg ctgaacgggg ggttcgtgca
5821 cacagcccag cttggagcga acgacctaca ccgaactgag atacctacag cgtgagctat
5881 gagaaagcgc cacgcttccc gaagggagaa aggcggacag gtatccggta agcggcaggg
5941 tcggaacagg agagcgcacg agggagcttc caggggggaaa cgcctggtat ctttatagtc
6001 ctgtcgggtt tcgccacctc tgacttgagc gtcgattttt gtgatgctcg tcaggggggc
6061 ggagcctatg gaaaaacgcc agcaacgcgg ccttttacg gttcctggcc ttttgctggc
```

```
-continued
6121 cttttgctca catgttcttt cctgcgttat ccctgattc tgtggataac cgtattaccg 6181 cctttgagtg agctgatacc gctcgccgca gccgaacgac cgagcgcagc gagtcagtga 6241 gcgaggaagc ggaagggcgc ccaatacgca aaccgcctct ccccgcgcgt tggccgattc 6301 attaatgcag ctggcacgac aggtttcccg actggaaagc gggcagtgag cgcaacgcaa 6361 ttaatgtgag ttagctcact cattaggcac cccaggcttt acactttatg cttccggctc 6421 gtatgttgtg tggaattgtg agcggataac aatttcacac aggaaacagc tatgaccatg 6481 attacgcca
```

Example 2: Testing of Heavy Chain Heterodimerization Mutants

Figure 4B:
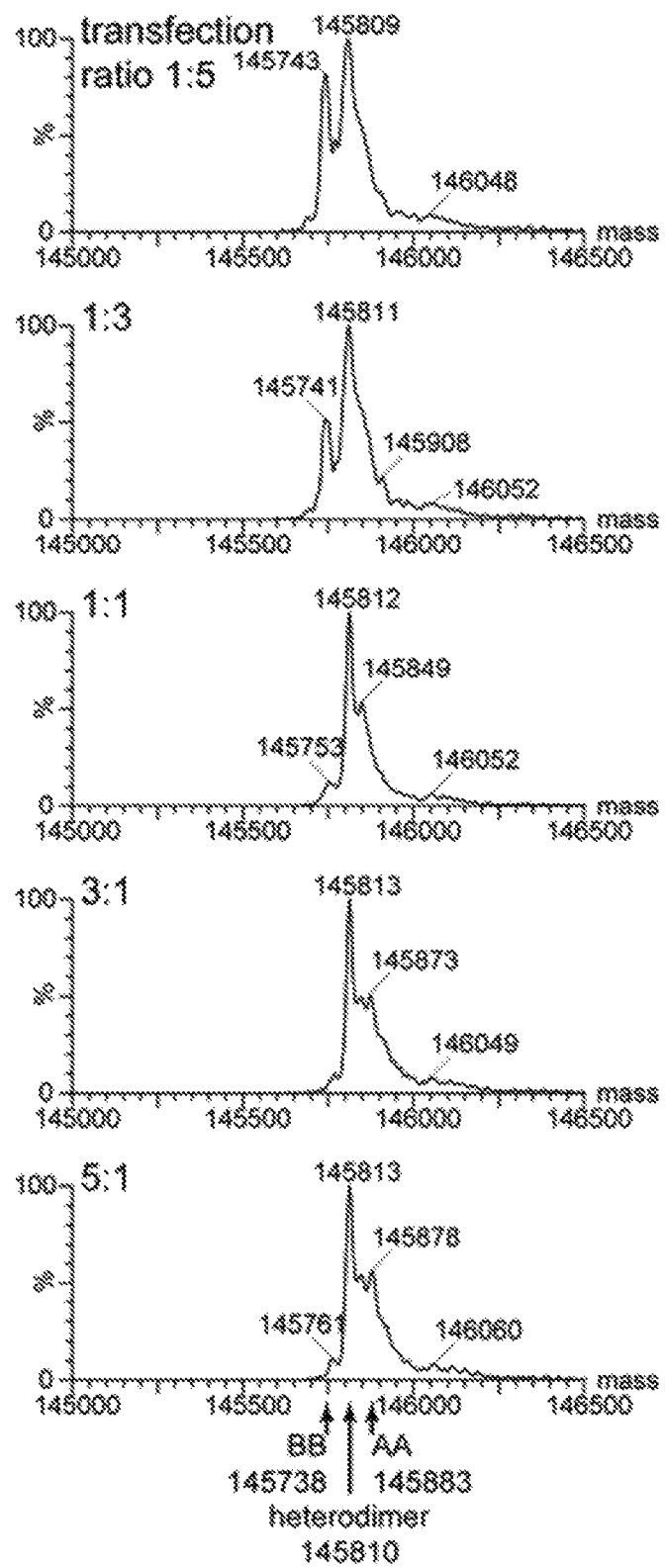
FIG. 4B shows a series of mass spectra that was used to quantify half-antibody formation. The MS spectra of the samples showed maximal amount of heterodimer and minimal homodimers are present at transfection ratio 1:1.

To further characterize the lysine repositioning designs, the mutations were incorporated into full IgG1 heavy chains. These constructs contained the same Fab on both heavy chains (anti-EGFR M60-A02) to limit potential influences and avoid the light chain pairing problem. Equal amounts of the two heavy chains and the light chain of M60-A02 were expressed in CHO transients and the supernatant analyzed by SDS-PAGE. All supernatants contained considerable amounts of half-antibodies composed of 1 heavy and 1 light chain, but the design MP4 produced a lower amount of half-antibodies than MP3 as shown by quantification of LC-MS peaks (data not shown). The mass spectrometry analysis also revealed that half-antibodies were formed only by heavy chain B in these samples (data not shown). This suggests that half-antibody formation may be a consequence of over-expression of heavy chain B, which opens up the possibility to reduce the level of half-antibodies by optimizing the ratio between the two heavy chains. Therefore, the heavy chains of design MP4 with identical Fabs (plasmids pMP254 and pMP399) were transfected into CHO-S cells in various ratios from 1:5 to 5:1. The total amount of heavy chains (14 μg) and the amount of light chain were kept constant in these transfections. The over-expression of chain A reduced the formation of half-antibodies and increased the amount of full IgG in the supernatants, confirming that half-antibody formation is influenced by differential expression between the chains (FIG. 4A). Since both heavy chains in these experiments contained the same Fab (anti-EGFR M60), a differential expression of the two heavy chains might be due to the CH3 mutation. However, mass spectrometry analysis also demonstrated that over-expression of either chain lead to increased formation of the respective homodimer (FIG. 4B). Thus, an equal ratio between the two heavy chains is a good compromise to minimize unwanted side products.

Example 3: Developing a Solution to the Light Chain Pairing Problem

In order to drive correct assembly of light chain:heavy chain (LC:HC) pairs in a bispecific antibody as illustrated in FIG. 1, the interface between the chains might be engineered so that steric clashes or repelling charges prevent incorrect assembly. The light chain of an antibody makes contact with the heavy chain in the variable domain and the constant domain, and both contacts (VL:VH and CL:CH1) contribute to recognition and engagement. Consequently, point mutations in the constant domains may not be sufficient to steer each light chain towards correct pairing, and engineering of the variable domains may become necessary. Therefore, an alternative strategy for solving the light chain pairing was pursued.

Figure 5A:
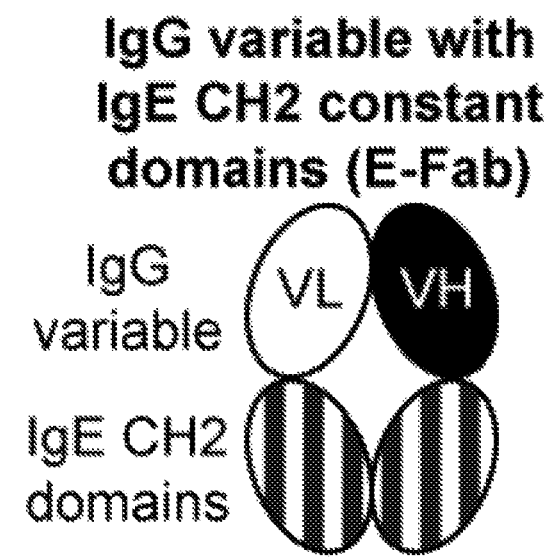
FIG. 5A is a diagrammatic representation of one of the application's solution to the light chain pairing problem, the creation of an E-fab. In an E-fab, the CH1 and CL domains are substituted by IgE CH2 (Cε2) domains, which form a natural dimer.

The variable domains of an antibody can maintain their binding properties in the absence of constant regions or when they are fused to heterologous proteins. We hypothesized that Ig-fold domains may be used in place of CH1/CL as a strategy to prevent mispairing of light chains and chose the CH2 domain of IgE (Cε2) as a candidate Ig-fold domain to substitute for the CH1:CL domain (FIG. 5A). The CH2 domain of IgE (Cε2) forms homodimers that are linked by two inter-chain disulfides. This domain serves as dimerization interface between IgE heavy chains instead of a hinge region, which is not present in IgE. Also, unlike the CH2 domain of IgG the Cε2 domain is not involved in effector function and makes no contact with the FcεRIα (Holdom et al., *Nature Struct. & Mol. Biol.*, 18:571-576, 2011).

Figure 5B:
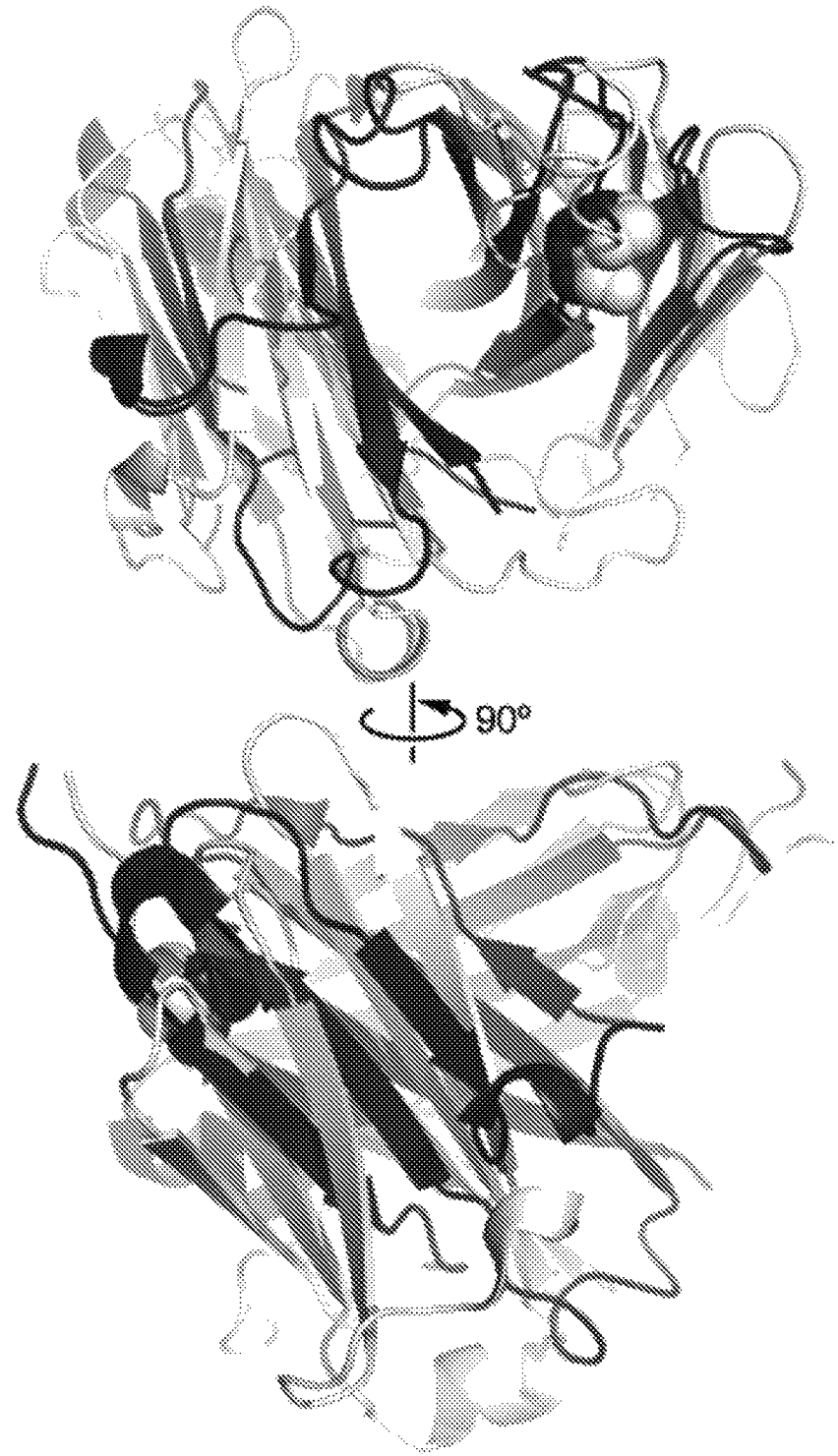
FIG. 5B is a superimposition of structures of the human Cε2 domain (white) and a human IgG1 CH1/kappa constant domains (black) which shows overall similarity of the Ig-folds. The Cε2 domains pair at a different angle and with greater distance in the upper portion of the interface, but tighter packing in the lower interface. The Pro at the beginning of β-strand A (represented as a sphere) is in a very similar position and orientation in the CH1/CL and Cε2 domains.

The structure of the Cε2 domain is similar to other Ig-fold domains such as CL and CH1 domains, but the interface and the angle between the units of a dimer are distinct (FIG. 5B). The two Cε2 domains in a dimer have less extensive interaction than other Ig-fold dimers, and the interaction is dominated by polar rather than the usual nonpolar residues. Thus, Cε2 and CH1:CL are overall so different that cross-pairing of the Ig-fold domains is unlikely. However, the two prolines that mark the start of the first β-strand of the Ig-fold (highlighted in bold and underlined in FIG. 5C) are in a similar position in the structures of Cε2 and CH1/kappa constant domains. Thus, it appears possible to fuse the variable domains of an antibody onto Cε2 domains, and maintain the geometry of the VH:VL pair and therefore its binding properties. This hybrid Fab construct composed of the variable domains of an antibody fused to Cε2 domains was named "E-Fab" (FIG. 5C). The amino acid sequence of the CH2 domain of human immunoglobulin E (IgE) is provided below (the N-linked glycosylation site is underlined):

(SEQ ID NO: 1)
```
  1 VCSRDFTPPT VKILQSSCDG GGHFPPTIQL LCLVSGYTPG TINITWLEDG

51 QVMDVDLSTA STTQEGELAS TQSELTLSQK HWLSDRTYTC QVTYQGHTFE

101 DSTKKCA
```

To fuse the VH domain to the Cε2 domain, the connector sequence (ASTKG (SEQ ID NO:7)) of the IgG1 CH1 constant region was joined to the first β-strand of the Cε2 domain starting with Pro2 (IMGT unique numbering of C-domains, FIG. 5C). The amino acid sequence of the CH2 domain of human immunoglobulin E (IgE) in which the first 8 amino acids (VCSRDFTP (SEQ ID NO:8)) are replaced with the first 5 amino acids of a human IgG1 CH1 domain (elbow region ASTKG (SEQ ID NO:7) is underlined) is provided below:

```
                                               (SEQ ID NO: 45)
  1 ASTKGPTVKI LQSSCDGGGH FPPTIQLLCL VSGYTPGTIN ITWLEDGQVM

51 DVDLSTASTT QEGELASTQS ELTLSQKHWL SDRTYTCQVT YQGHTFEDST

101 KKCA
```

The same strategy was used for fusing the VL to the Cε2 domain with the connector from the kappa constant region (RTVAA (SEQ ID NO:9)). The amino acid sequence of the CH2 domain of human immunoglobulin E, in which the first 8 amino acids (VCSRDFTP (SEQ ID NO:8)) are replaced with the first 5 amino acids of a human kappa domain (elbow region RTVAA (SEQ ID NO:9) is underlined) is provided below:

```
                                               (SEQ ID NO: 46)
  1 RTVAAPTVKI LQSSCDGGGH FPPTIQLLCL VSGYTPGTIN ITWLEDGQVM

51 DVDLSTASTT QEGELASTQS ELTLSQKHWL SDRTYTCQVT YQGHTFEDST

101 KKCA
```

The human Cε2 domain has one N-linked glycosylation site at Asn38 (IMGT numbering), which was mutated to Gln to prevent glycosylation of this site in the E-Fab. In this initial design, the variable domains were grafted onto a Cε2 domain, which is unaltered except for the agly mutation and identical between heavy and light chain. This first design was named E-Fab E0. The amino acid sequences of the E0 design of the heavy chain of an E-Fab is provided below (the N-glycosylation site is mutated to glutamine):

```
                                               (SEQ ID NO: 3)
  1 ASTKGPTVKI LQSSCDGGGH FPPTIQLLCL VSGYTPGTIQ ITWLEDGQVM

51 DVDLSTASTT QEGELASTQS ELTLSQKHWL SDRTYTCQVT YQGHTFEDST

101 KKCA
```

The amino acid sequences of the E0 design of the light chain of an E-Fab is provided below (the N-glycosylation site is mutated to glutamine):

```
                                               (SEQ ID NO: 4)
  1 RTVAAPTVKI LQSSCDGGGH FPPTIQLLCL VSGYTPGTIQ ITWLEDGQVM

51 DVDLSTASTT QEGELASTQS ELTLSQKHWL SDRTYTCQVT YQGHTFEDST

101 KKCA
```

However, since the Cε2 domain normally homodimerizes, additional mutations were introduced into the domains to prevent the formation of HC:HC or LC:LC dimers, and these designs were named E-Fab E1 through E3 (Table 3; positions according to IMGT numbering system).

TABLE 3

Constructs for E-Fab testing.

| Fab A (anti-EGFR M60-A02) | light chain construct | heavy chain construct (HSA-fusion) |
|---|---|---|
| wt IgG1 | pXWU174 | pMP363 |
| E-Fab E0 | pMP386 (N38Q) | pMP390 (N38Q) |
| E-Fab E1 | pMP387 (N38Q, L22G) | pMP391 (N38Q, L7W) |
| E-Fab E2 | pMP463 (N38Q, T121G) | pMP392 (N38Q, S10I) |
| E-Fab E3 | pMP464 (N38Q, T121S) | pMP465 (N38Q, S10T) |
| Fab B (anti-IGF-1R C06) | light chain (GFP fusion) | heavy chain |
| wt IgG1 (no mutations) | pMP340 | pMP341 |

The amino acid sequences of the E1 design of the heavy chain of an E-Fab is provided below:

```
                                              (SEQ ID NO: 47)
  1 ASTKGPTVKI WQSSCDGGGH FPPTIQLLCL VSGYTPGTIQ ITWLEDGQVM

51 DVDLSTASTT QEGELASTQS ELTLSQKHWL SDRTYTCQVT YQGHTFEDST

101 KKCA
```

The amino acid sequences of the E1 design of the light chain of an E-Fab is provided below:

```
                                              (SEQ ID NO: 48)
  1 RTVAAPTVKI LQSSCDGGGH FPPTIQLGCL VSGYTPGTIQ ITWLEDGQVM

51 DVDLSTASTT QEGELASTQS ELTLSQKHWL SDRTYTCQVT YQGHTFEDST

101 KKCA
```

The amino acid sequences of the E2 design of the heavy chain and the light chain of an E-Fab are provided at the end of this Example.

The amino acid sequences of the E3 design of the heavy chain of an E-Fab is provided below:

```
                                              (SEQ ID NO: 49)
  1 ASTKGPTVKI LQSTCDGGGH FPPTIQLLCL VSGYTPGTIQ ITWLEDGQVM

51 DVDLSTASTT QEGELASTQS ELTLSQKHWL SDRTYTCQVT YQGHTFEDST

101 KKCA
```

The amino acid sequences of the E3 design of the light chain of an E-Fab is provided below:

```
                                              (SEQ ID NO: 50)
  1 RTVAAPTVKI LQSSCDGGGH FPPTIQLLCL VSGYTPGTIQ ITWLEDGQVM

51 DVDLSTASTT QEGELASTQS ELTLSQKHWL SDRTYTCQVT YQGHTFEDSS

101 KKCA
```

To evaluate the E-Fab designs in controlling light chain pairing, test constructs were built using the two Fabs M60-A02 anti-EGFR and M13.006 anti-IGF1R. Both heavy chains belong to the subgroup HV3, and can therefore be purified using protein A. The test molecules were tagged with GFP (30 kDa, LC of Fab B anti IGF-1R) or HSA (66 kDa, HC of Fab A or E-Fab, anti-EGFR) to enable simple differentiation of correct vs. incorrect pairing by migration on SDS page (FIG. 6A). The E-Fab constructs were built from gBlocks. Additional mutations were introduced into the Cε2 domain by PCR-based mutagenesis, and products cloned into CHO expression vectors derived from pV90/pV100 by restriction enzyme-based methods (Table 3). The Fabs were co-expressed by transient transfection in CHO-S cells at 40 ml scale. Cells were shifted to 28° C. for expression 24 hours after transfection, and supernatants harvested after 8 days and cleared by centrifugation and filtration (0.22 μm).

Figure 6B:
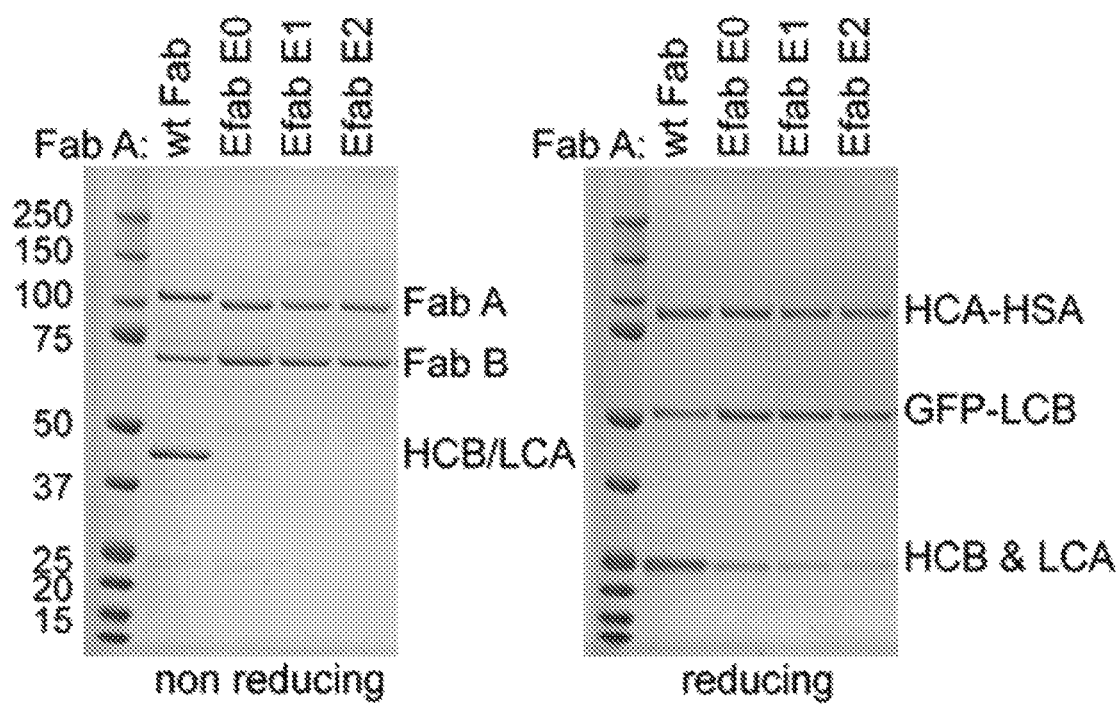
FIG. 6B is an analysis of Fab-pairing by SDS-page. The indicated HSA-tagged anti-EGFR M60-A02 Fabs or E-Fabs were co-expressed with a GFP-tagged Fab anti-IGF-1R C06 (see also, Table 3). Correct pairing of heavy and light chains produces bands at 114 and 74 kDa under non-reducing conditions, while bands at 47 or 140 kDa indicate mispairing.
Figure 6D:
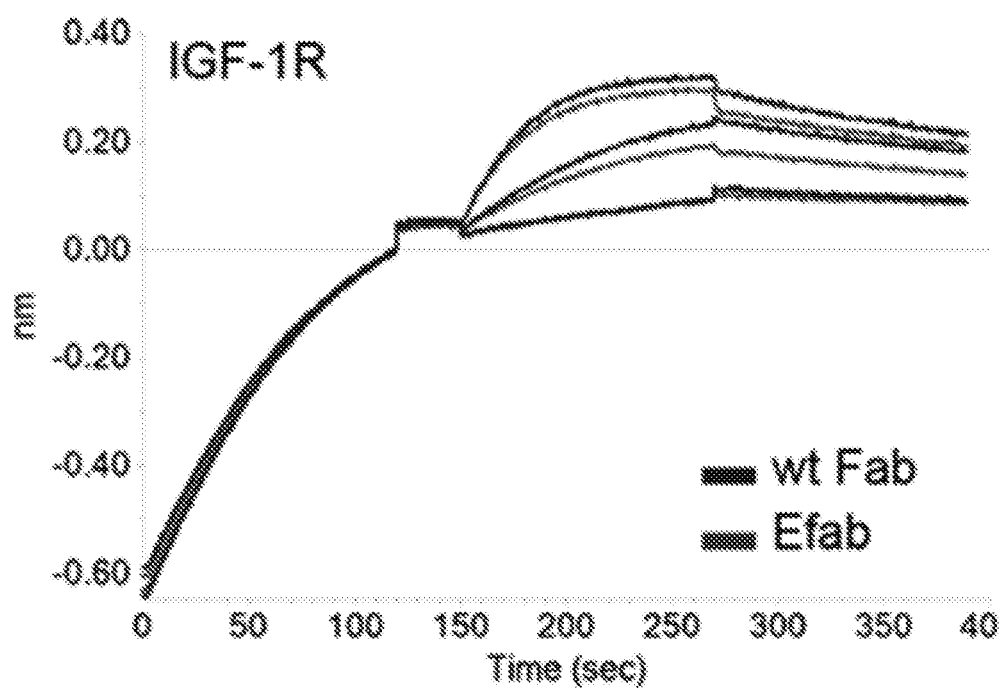
FIG. 6D is a graph depicting binding of the anti-IGF-1R E-Fab as tested by Octet. The Fabs were expressed individually, purified on protein A spin columns, and used in Octet binding (300 nM, 100 nM, and 30 nM) to soluble IGF1-R loaded onto His-tips.

Analysis of the expressed proteins by SDS-PAGE showed that the E-Fab composed of the variable domains of a regular antibody fused to the Cε2 domain was highly efficient in controlling the light chain pairing. When the two Fabs M60-A02 and M13-0036 were co-expressed as wild-type IgG1/kappa Fab, mispairing of the M60-A02 light chain with the M13-006 heavy chain was readily detected (FIG. 6B). However, when the M60-A02 was made as E-Fab, no mispairing was seen. In contrast, point mutations in the CH1/CL domains failed to abrogate light chain mispairing in this experiment (data not shown). Similarly, when the anti-IGF-1R M13-006 was constructed as E-Fab, no mispairing was detected when it was co-expressed with another Fab (anti IGF-1R G11) (FIG. 6C). Importantly when the Fabs were expressed individually and binding to antigens tested by Octet, the E-fabs and wild-type Fabs similarly bound to His-tagged IGF-1R, which was loaded onto anti-His tips (FIG. 6D).

Thus, based on the above data the E-Fab is an excellent strategy to solve the light chain pairing problem in a bispecific antibody, as it enforces strictly correct chain pairing and the binding properties of the Fab are maintained.

Interestingly, the Cε2 domain did not strongly induce the formation of homodimers between the chains of the E-Fab. Nevertheless, the designs E2 and E3, which are engineered to form heterodimers between heavy and light chain, were carried forward and tested in the context of full bispecifics. Only the design E1, which appeared to induce some dimerization between heavy chains (FIG. 6B) was not tested further. The peptide sequence of the constant domains of the E-Fab design E2 are shown below:

```
Amino Acid Sequence of E-Fab light chain constant
region, agly N38Q (design E2, T121G, pMP463)
                                                         (SEQ ID NO: 6)
  1 RTVAAPTVKI LQSSCDGGGH FPPTIQLLCL VSGYTPGTIQ ITWLEDGQVM DVDLSTASTT

61 QEGELASTQS ELTLSQKHWL SDRTYTCQVT YQGHTFEDSG KKCA

Amino Acid Sequence of E-Fab heavy chain constant
region, agly N38Q (design E2, S10I, pMP392)
                                                         (SEQ ID NO: 5)
  1 ASTKGPTVKI LQSICDGGGH FPPTIQLLCL VSGYTPGTIQ ITWLEDGQVM DVDLSTASTT

61 QEGELASTQS ELTLSQKHWL SDRTYTCQVT YQGHTFEDST KKCA
```

Example 4: Building and Testing a Bispecific Asymmetric IgG

Figure 7:
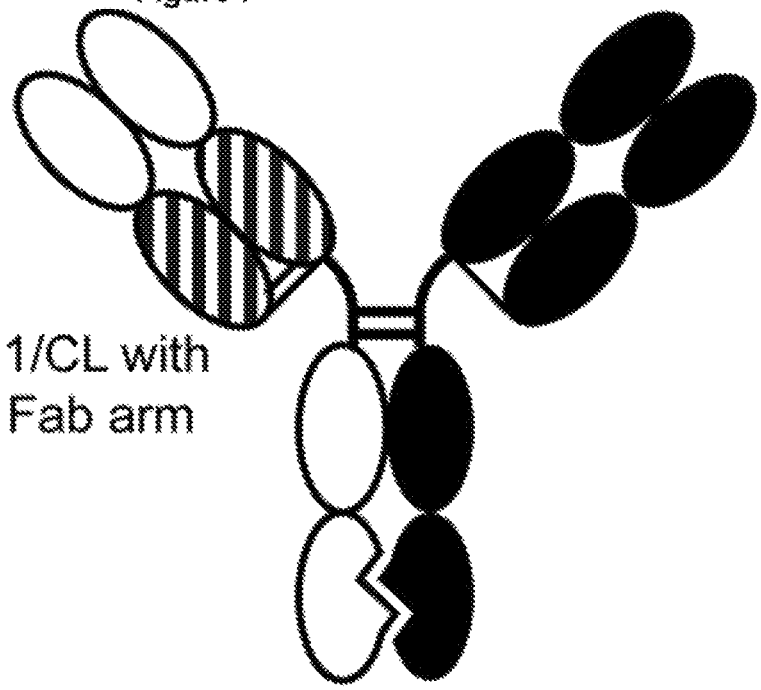
FIG. 7 is a schematic representation of an asymmetric IgG with E-Fab and lysine repositioning. The constant domains of one Fab arm are replaced with the E-Fab, while the other Fab arms contains wild-type IgG CH1/CL domains to solve the light chain pairing problem. The lysine repositioning mutations are included in the CH3 domains of the two heavy chains to enforce heterodimerization.

The E-Fab and lysine repositioning constructs were combined to generate full IgG-like bispecific antibodies. Such a bispecific antibody is composed of 4 different chains, and contains both light chain pairing and heavy chain hererodimerization solutions (FIG. 7). Using again the anti-EGFR antibody M60-A02, and anti-IGF1R M13.006 or G11, the two different IgG1 heavy chains were built with the heterodimerization mutations MP3.

```
Amino Acid Sequence of mature M60-A02 Ebody heavy chain (EFab E2, mp3a heterodimerization,
pMP401))(CH2 domain underlined; CH3 domain boldened)
                                                                  (SEQ ID NO: 51)
EVQLLESGGG LVQPGGSLRL SCAASGFTFS DYIMHWVRQA PGKGLEWVSV ISSSGGDTSY ADSVKGRFTI

SRDNSKNTLY LQMNSLRAED TAVYYCAKVL AGYFDWLPFD YWGQGTLVTV SSASTKGPTV KILQSICDGG

GHFPPTIQLL CLVSGYTPGT IQITWLEDGQ VMDVDLSTAS TTQEGELAST QSELTLSQKH WLSDRTYTCQ

VTYQGHTFED STKKCASDKT HTCPPCPAPE LLGGPSVFLF PPKPKDTLMI SRTPEVTCVV VDVSHEDPEV

KFNWYVDGVE VHNAKTKPRE EQYNSTYRVV SVLTVLHQDW LNGKEYKCKV SNKALPAPIE KTISKAKGQP

REPQVYTLPP SRDELTKNQV KLTCLVKGFY PSDIAVEWES NGQPENNYKT TPPVLDSDGS FFLYSSLTVD

KSRWQQGNVF SCSVMHEALH NHYTQKSLSL SPG

Amino Acid Sequence of mature M60-A02 Ebody light chain (EFab E2, pMP463)(CH2 domain
underlined)
                                                                  (SEQ ID NO: 52)
DIQMTQSPAT LSLSPGETAT LSCRASQSVS YYLAWYQQKP GQAPRLLIYD TFNRATGIPA RFSGSGSGTD

FTLTISRLEP EDFAVYYCQQ YGSSPPWLTF GGGTKVEIKR TVAAPTVKIL QSSCDGGGHF PPTIQLLCLV

SGYTPGTIQI TWLEDGQVMD VDLSTASTTQ EGELASTQSE LTLSQKHWLS DRTYTCQVTY QGHTFEDSGK

KCA

Amino Acid Sequence of mature M13.C06 IgG1 heavy chain (mp3b heterodimerization, pMP404)
(CH3 domain boldened)
                                                                  (SEQ ID NO: 53)
EVQLLESGGG LVQPGGSLRL SCAASGFTFS IYRMQWVRQA PGKGLEWVSG ISPSGGTTWY ADSVKGRFTI

SRDNSKNTLY LQMNSLRAED TAVYYCARWS GGSGYAFDIW GQGTMVTVSS ASTKGPSVFP LAPSSKSTSG

GTAALGCLVK DYFPEPVTVS WNSGALTSGV HTFPAVLQSS GLYSLSSVVT VPSSSLGTQT YICNVNHKPS

NTKVDKKVEP KSCDKTHTCP PCPAPELLGG PSVFLFPPKP KDTLMISRTP EVTCVVVDVS HEDPEVKFNW

YVDGVEVHNA KTKPREEQYN STYRVVSVLT VLHQDWLNGK EYKCKVSNKA LPAPIEKTIS KAKGQPREPQ

VYTLPPSRDE LTKNQVSLTC LVSGFYPSDI AVEWESNGQP ENNYKTTPPV LDSDGSFKLY SKLTVDKSRW

QQGNVFSCSV MHEALHNHYT QKSLSLSPG
```

-continued

Amino Acid Sequence of mature M13.C06 kappa light chain (pMP407)

(SEQ ID NO: 54)

DIQMTQSPLS LSASVGDRVT ITCQASRDIR NYLNWYQQKP GKAPKLLIYD ASSLQTGVPS RFGGSGSGTD

FSFTIGSLQP EDEATYYCQQ FDSLPHTFGQ GTKLEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC

To control the pairing of the different light chains, the anti-EGFR Fab was constructed as Efab (FIG. 7). A control antibody was built with the lysine repositioning mutations to generate an IgG1 heavy chain heterodimer that lacks a light chain pairing solution.

Figure 8B:
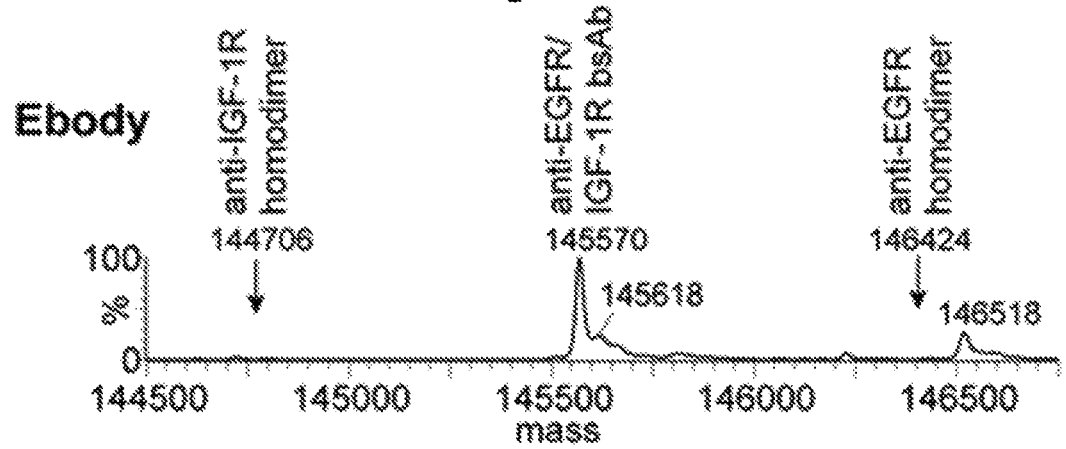
FIG. 8B is a representation of a mass spectrometry analysis of the asymmetric IgGs from FIG. 8A which shows no light chain mispairing in the E-body but significant amounts of antibody with mispaired LC in the control. Heavy chain homodimers were not detectable in either sample.
Figure 8B:
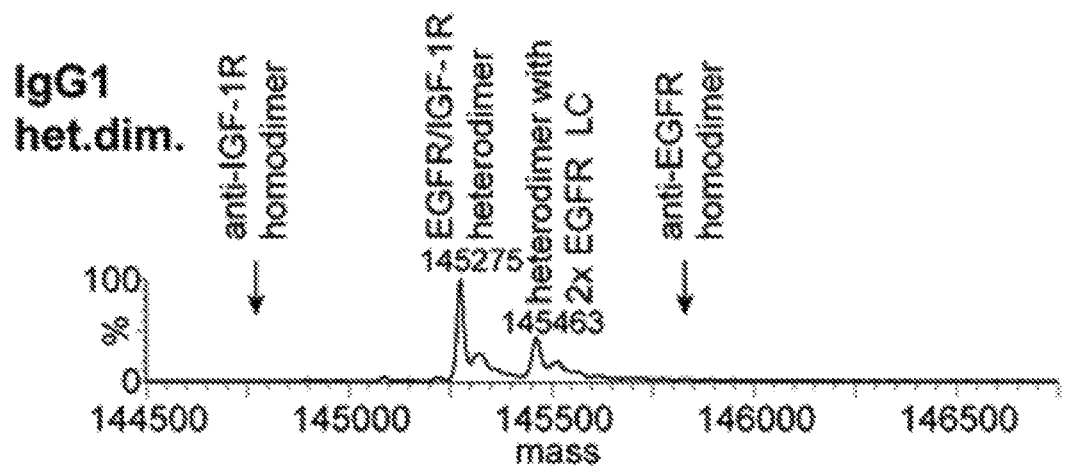

The antibodies were again expressed in CHO-S cells by transient transfection and the supernatants harvested and cleared after 8 days of culture. Separation by SDS-PAGE showed a band migrating at the size of a full IgG and an additional band corresponding to half-antibodies (FIG. 8A). Mass spectrometry analysis demonstrated that half-antibodies were again formed by the heavy chain B in these experiments. Importantly, no light chain mispairing was detected in the E-Fabs by LC-MS. The IgG1 heterodimer showed some correct paring of heavy chains with their light chains, but a strong peak of heavy chain heterodimer with two anti-EGFR light chains was also detectable (FIG. 8B). These results confirm again that the E-Fab solves the light chain pairing problem.

Importantly, homodimers between the heavy chains were not detectable in the mass-spec profiles, demonstrating that the heavy chain heterodimerization by lysine repositioning is highly efficient when combined with an E-Fab (FIG. 8B). However, mass spectrometry also revealed small levels of O-glycans that were present on Efab bispecifics but not on the IgG1 control.

Figure 8D:
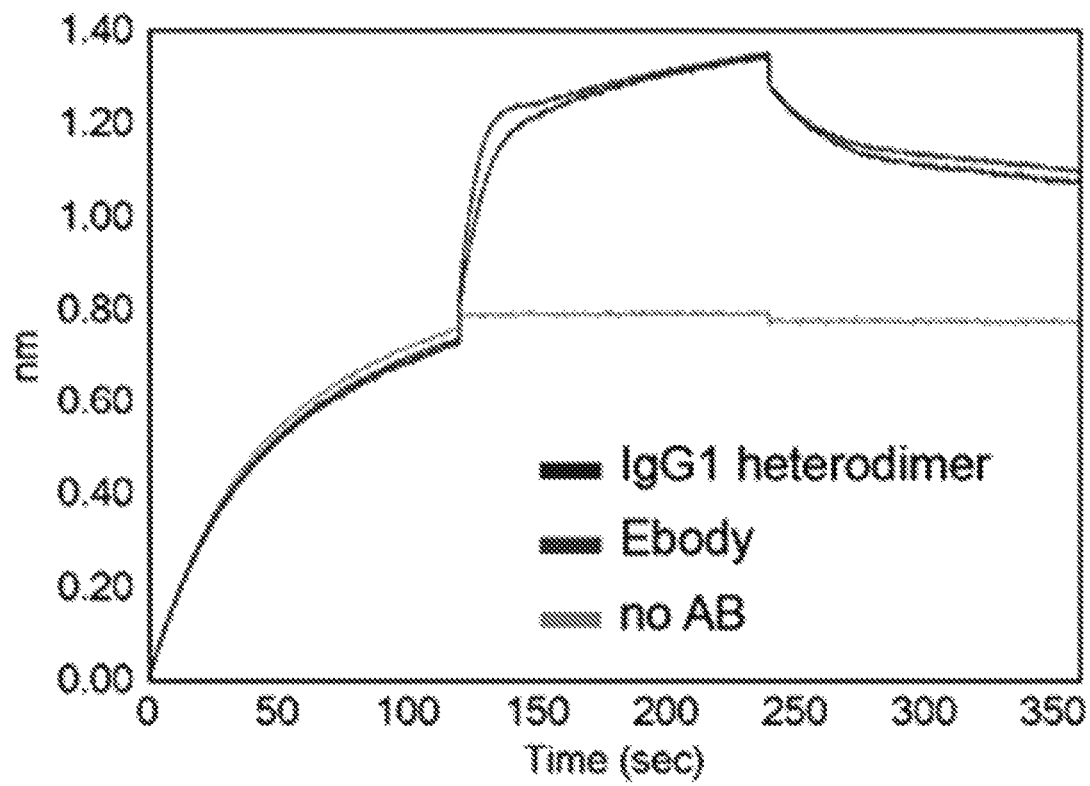
FIG. 8D is a graph depicting binding of the bispecific antibodies to His-tagged IGF-1R. Undiluted supernatants from CHO-S cells were used in Octet binding after loading of his-tagged ligands (5 µg/mL).

Next, crude supernatants were used in Octet binding experiments with soluble His-tagged EGFR (FIG. 8C) and IGF-1R (FIG. 8D). The IgG1 control as well as the bispecific Ebody bound to both EGFR and IGF-1R, but the binding appeared somewhat different between Ebody and control. However, the interpretation of these results is complex due to the different expression, amounts of half antibody and light chain mispairing in these crude samples.

Altogether, the analysis by mass spectrometry together with the binding data demonstrate that the Ebody correctly assembled into an asymmetric IgG. This is simply achieved by co-expression of the four different chains (2HC and 2 LC) in CHO cells. The E-fab fully solved light chain pairing, and the lysine repositioning strictly enforced heavy chain heterodimerization in these experiments.

Example 5: Further Testing of the Bispecific Platform

Figure 9:
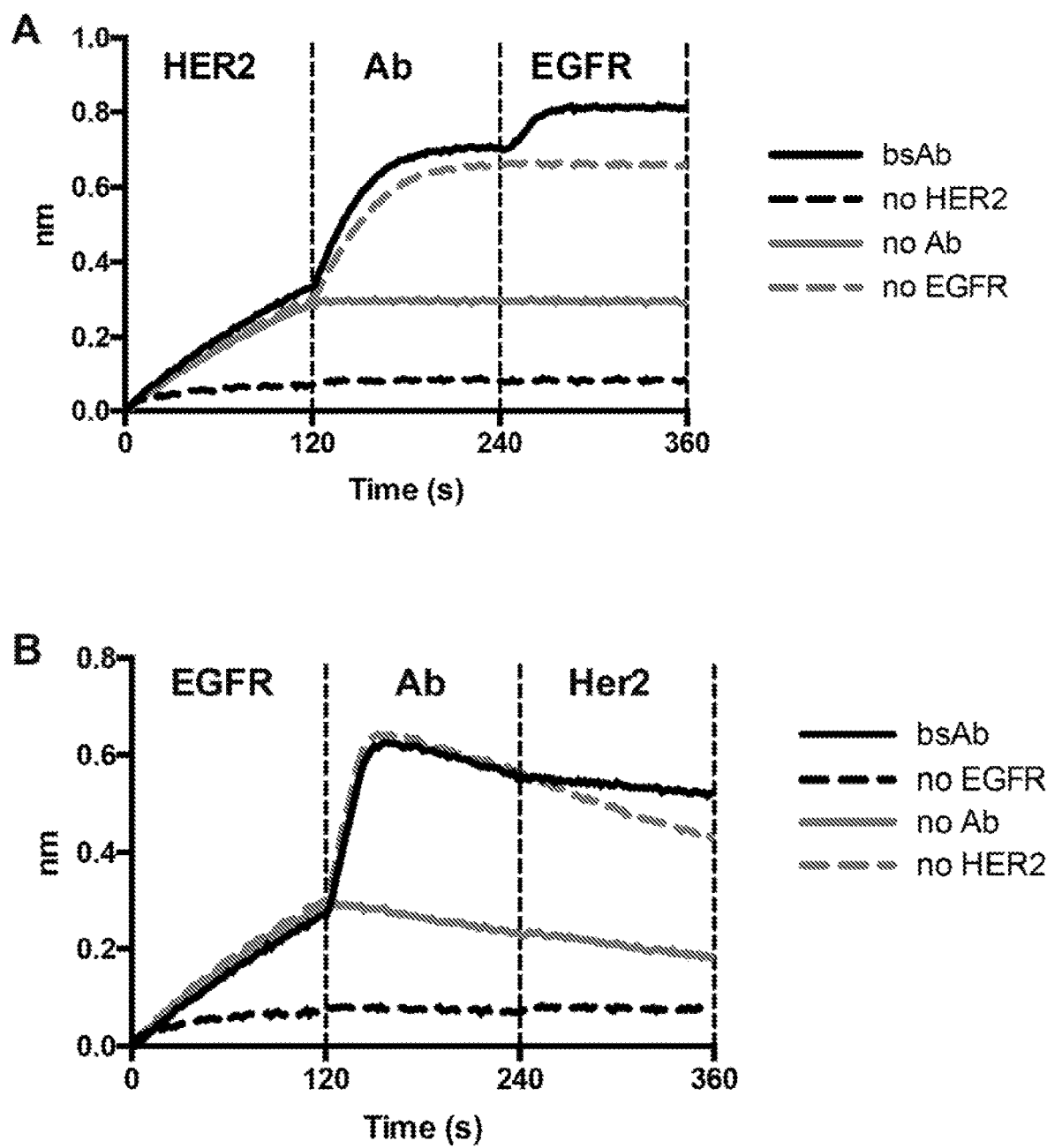
FIG. 9A is a graph depicting simultaneous binding of two antigens by a Trastuzumab/Cetuximab bispecific antibody. His-tagged soluble HER2 (5 µg/ml) was loaded onto Octet tips allowing capture of the bispecific antibody (200 nM) in the next step. Subsequent binding of EGFR (15 µg/ml) demonstrates simultaneous binding of both ligands by the bispecific.
FIG. 9B is a graph depicting the results of the reverse of the experiment shown in FIG. 9A. EGFR was loaded first, followed by binding of the bispecific antibody and HER2.

To further test the bispecific platform using Efab and Fc heterodimerization, another IgG-like bispecific antibody was generated from two therapeutic antibodies, Trastuzumab and Cetuximab, which are approved for the treatment of various cancers. To generate the bispecific, the anti-HER antibody Trastuzumab was cloned using the light chain pairing-solution Efab, and was then combined with the anti-EGFR antibody Cetuximab using the mp4 heavy chain heterodimerization mutations (S364K/K409L and K370S/V3971/F405K). The four plasmids (pMP521, pMP526, pMP528, and pMP530) encoding the two heavy chains and two light chains of the antibody were then co-expressed in CHO-S cells by means of transient transfection, and the resulting bispecific antibody purified by protein A. This antibody was then used in Octet binding studies with soluble versions of the two antigens, HER2 and EGFR (see, FIGS. 9A and 9B). As shown in FIGS. 9A and 9B, the bispecific antibody is capable of simultaneous binding to both its antigens.

pMP530 Trastuzumab Efab IgG1 mp4a (SEQ ID NO: 79)

```
  1 EVQLVESGGG LVQPGGSLRL SCAASGFNIK DTYIHWVRQA PGKGLEWVAR

51 IYPTNGYTRY ADSVKGRFTI SADTSKNTAY LQMNSLRAED TAVYYCSRWG

101 GDGFYAMDYW GQGTLVTVSS ASTKGPTVKI LQSICDGGGH FPPTIQLLCL

151 VSGYTPGTIQ ITWLEDGQVM DVDLSTASTT QEGELASTQS ELTLSQKHWL

201 SDRTYTCQVT YQGHTFEDST KKCASDKTHT CPPCPAPELL GGPSVFLFPP

251 KPKDTLMISR TPEVTCVVVD VSHEDPEVKF NWYVDGVEVH NAKTKPREEQ

301 YNSTYRVVSV LTVLHQDWLN GKEYKCKVSN KALPAPIEKT ISKAKGQPRE

351 PQVYTLPPSR DELTKNQVKL TCLVKGFYPS DIAVEWESNG QPENNYKTTP

401 PVLDSDGSFF LYSLLTVDKS RWQQGNVFSC SVMHEALHNH YTQKSLSLSP

451 G
```

```
-continued
pMP528 Trastuzumab Efab light chain
                                              (SEQ ID NO: 80)
  1 DIQMTQSPSS LSASVGDRVT ITCRASQDVN TAVAWYQQKP GKAPKLLIYS

51 ASFLYSGVPS RFSGSRSGTD FTLTISSLQP EDFATYYCQQ HYTTPPTFGQ

101 GTKVEIKRTV AAPTVKILQS SCDGGGHFPP TIQLLCLVSG YTPGTIQITW

151 LEDGQVMDVD LSTASTTQEG ELASTQSELT LSQKHWLSDR TYTCQVTYQG

201 HTFEDSGKKC A pMP521 Cetuximab IgG1 mp4b
                                              (SEQ ID NO: 81)
  1 DILLTQSPVI LSVSPGERVS FSCRASQSIG TNIHWYQQRT NGSPRLLIKY

51 ASESISGIPS RFSGSGSGTD FTLSINSVES EDIADYYCQQ NNNWPTTFGA

101 GTKLELKRTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201 LSSPVTKSFN RGEC pMP526 Cetuximab kappa
                                              (SEQ ID NO: 82)
  1 QVQLKQSGPG LVQPSQSLSI TCTVSGFSLT NYGVHWVRQS PGKGLEWLGV

51 IWSGGNTDYN TPFTSRLSIN KDNSKSQVFF KMNSLQSNDT AIYYCARALT

101 YYDYEFAYWG QGTLVTVSAA STKGPSVFPL APSSKSTSGG TAALGCLVKD

151 YFPEPVTVSW NSGALTSGVH TFPAVLQSSG LYSLSSVVTV PSSSLGTQTY

201 ICNVNHKPSN TKVDKKVEPK SCDKTHTCPP CPAPELLGGP SVFLFPPKPK

251 DTLMISRTPE VTCVVVDVSH EDPEVKFNWY VDGVEVHNAK TKPREEQYNS

301 TYRVVSVLTV LHQDWLNGKE YKCKVSNKAL PAPIEKTISK AKGQPREPQV

351 YTLPPSRDEL TKNQVSLTCL VSGFYPSDIA VEWESNGQPE NNYKTTPPIL

401 DSDGSFKLYS KLTVDKSRWQ QGNVFSCSVM HEALHNHYTQ KSLSLSPG
```

Example 6: Further Testing of Light Chain Pairing Solutions

Figure 10:
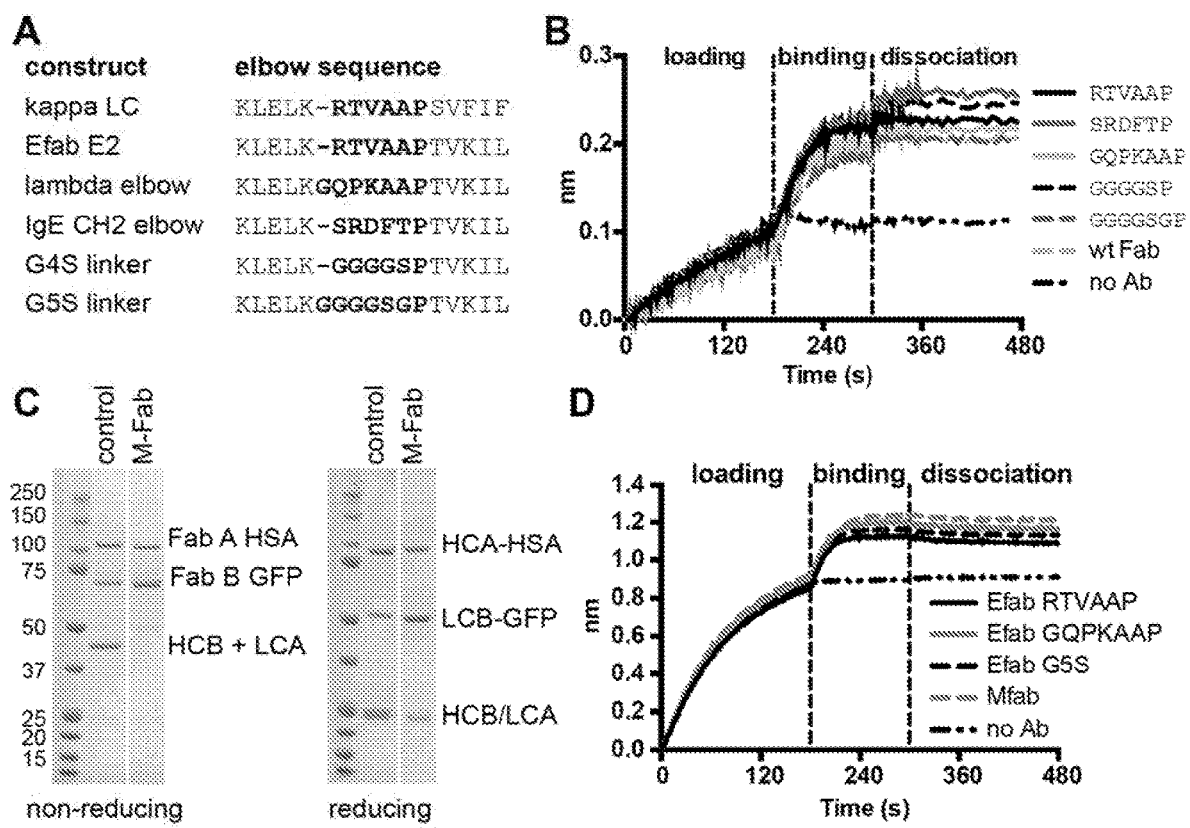
FIG. 10A shows Efab constructs with various elbow linker sequences. The anti-HER2 antibody Trastuzumab was engineered as Efab. Various elbow linker sequences that were included in the light chain are listed in the table (SEQ ID NOs: 96-101, respectively, in order of appearance). The sequences include the last 5 amino acids of the variable domain as well as the first κ amino acids of the IgE CH2 domain in addition to the elbow sequence (bold).
FIG. 10B is a graph of Octet binding studies. The Efabs were expressed as asymmetric IgG with Cetuximab in CHO cells (as in FIG. 9), purified and used in Octet binding studies (100 nM) with His-tagged HER2 (5 µg/ml) loaded onto anti-His tips. This figure discloses SEQ ID NOS 102-106, respectively, in order of appearance.
FIG. 10C is an analysis of Fab-pairing by SDS-page. To assess whether the IgM CH2 domain could solve the light chain pairing equally well as the IgE CH2 domain, two Fabs (anti-EGFR M60 and anti-IGF-1R C06) were co-expressed: with one Fab fused to HSA and another Fab fused to GFP. The kappa and CH1 constant domains of the Fab were replaced with IgM CH2 domains (the resulting molecule was named M-Fab). Analysis of the chain pairing by SDS-PAGE showed that the M-Fab solved the light chain mispairing between M60 and C06 that was prominently observed in the control.
FIG. 10D is a graph of Octet binding studies. The Efabs and the M-Fab were expressed in CHO-S as Fabs (without Fc), and the supernatants were used for testing binding to HER2 by Octet. This figure discloses SEQ ID NOs: 102, 104 and 58, respectively, in order of appearance.

To further optimize the construction of Efabs, the linkers between the variable domains and the CH2 domain of IgE were investigated further. In previous examples the elbow regions from human kappa and CH1 domains were used as linkers between the variable domains and IgE CH2. However, other linker sequences could potentially alter the geometry or provide a different degree of flexibility, and thus affect the correct assembly of the chains or the binding of antigen by the Efab. To test this, the anti-HER2 antibody Trastuzumab was engineered as Efab and included various elbow sequences within the light chain. The linkers used were from a lambda light chain or from the human IgE CH2 domain, or flexible Gly-Ser linkers of different lengths (FIG. 10). The Efabs were expressed as asymmetric IgG with Cetuximab (as in FIG. 9) in CHO cells by transient transfection. The material was purified by protein A and tested in Octet binding studies. Interestingly, the various elbow linker sequences had little effect on the ability of Trastuzumab to bind to HER2, and all construct showed similar binding compared to a wild-type Trastuzumab Fab.

The IgM class of antibodies contains a CH2 domain similarly to IgE, which acts in place of a hinge region to pair two heavy chains by a disulfide bridge. Thus, it was tested whether using the IgM CH2 domain could solve the light chain pairing equally well as the IgE CH2 domain. To test this, two Fabs (M60 and C06) were again co-expressed as shown in FIG. 6A, with one Fab fused to HSA and another Fab fused to GFP. In this case, however, the kappa and CH1 constant domain of one Fab were replaced with IgM CH2 domains, and the resulting molecule was named M-Fab (FIG. 10C). Analysis of the chain pairing by SDS-PAGE showed that the M-Fab solved the light chain mispairing between M60 and C06 that was prominently observed in the control (FIG. 10C). Thus, the M-Fab appears to function as efficiently as the Efab in solving the light chain pairing problem.

Next, the ability of an M-Fab to bind antigen was compared to Efabs with various elbow regions in the light chain. These Efab and the M-Fab were again constructed using the variable domains of the anti-HER2 antibody Trastuzumab. The mature peptide sequences of the heavy and light chain of the M-Fab construct are shown below.

```
Amino Acid Sequence of a Trastuzumab M-fab
heavy chain with 6x His tag (pMP623) (elbow
region boldened; IgM CH2 domain underlined;
6xHis italicized)
                                              (SEQ ID NO: 75)
EVQLVESGGG LVQPGGSLRL SCAASGFNIK DTYIHWVRQA

PGKGLEWVAR IYPTNGYTRY ADSVKGRFTI SADTSKNTAY

LQMNSLRAED TAVYYCSRWG GDGFYAMDYW GQGTLVTVSS

ASTKGPKVSV FVPPRDGFFG NPRKSKLICQ ATGFSPRQIQ

VSWLREGKQV GSGVTTDQVQ AEAKESGPTT YKVTSTLTIK
```

```
-continued
ESDWLGQSMF TCRVDHRGLT FQQQASSMCH HHHHH

Amino Acid Sequence of a Trastuzumab M-fab
light chain (pMP596) (elbow region boldened;
IgM CH2 domain underlined
                                    (SEQ ID NO: 76)
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIKRTV AAPKVSVFVP

PRDGFFGNPR KSKLICQATG FSPRQIQVSW LREGKQVGSG

VTTDQVQAEA KESGPTTYKV TSTLTIKESD WLGQSMFTCR

VDHRGLTFQQ QASSMC
```

The Efabs and the M-Fab were expressed in CHO-S as Fabs (without Fc), and the supernatants used for testing binding to HER2 by Octet. In this binding assay the Mfab and the various Efab constructs showed very similar binding (FIG. 10D).

Together these results show that using the IgM CH2 domains as constant domains of a Fab (M-fab) solves the light chain pairing problem and maintains the binding characteristics of the Fab. Thus, the M-Fab is another useful light chain pairing solution.

Example 7: Additional Applications of Heavy and Light Chain Pairing Technologies Next, the heavy and light chain pairing solutions were tested further in the context of various other bispecific and monospecific formats to explore how versatile and functional of these technologies are.

Figure 11:
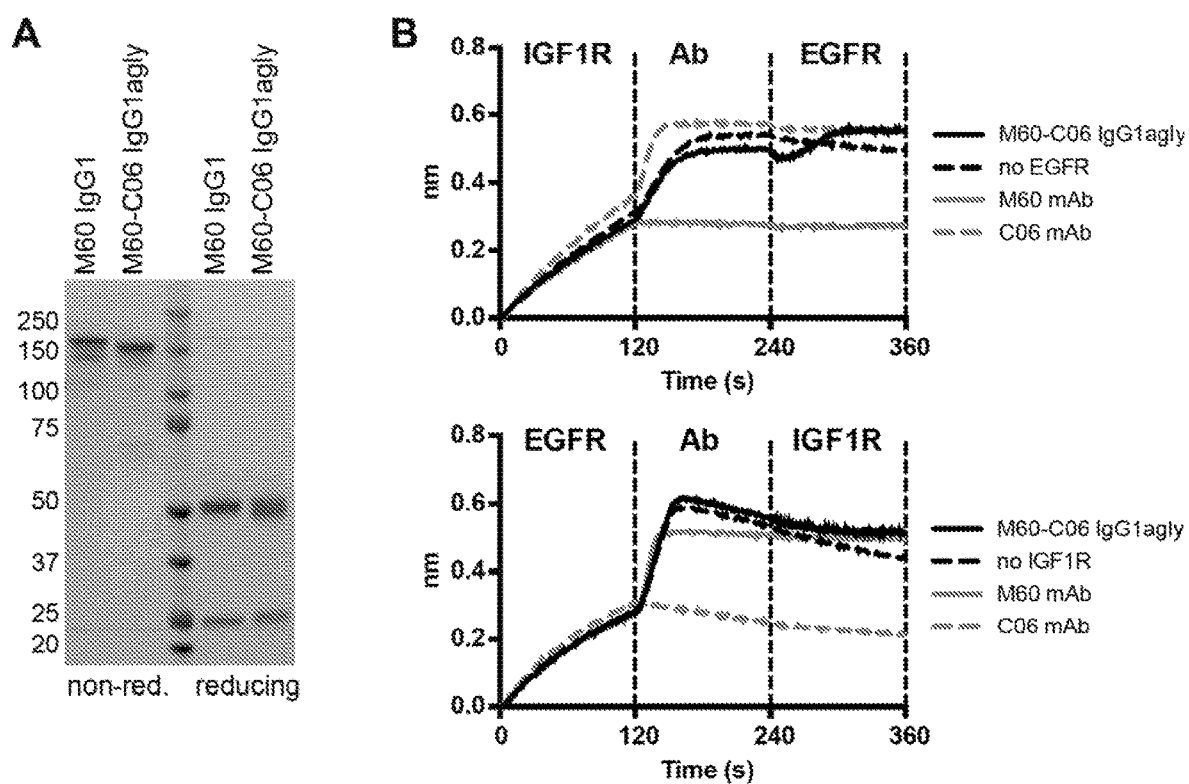
FIG. 11A shows a photograph of a gel of a bispecific antibody comprising an anti-EGFR M60-A02 Efab and the anti-IGF1R M13.006 as a normal Fab with an IgG1 agly (T299A) constant region containing mp3 heterodimer mutations expressed in CHO cells and purified by protein A.
FIG. 11B shows the results of Octet studies where the bispecific was tested for simultaneous binding. In the upper panel, His-tagged soluble IGF1R (5 µg/ml) was bound to Octet tips, followed by binding of the bispecific antibody or the respective mAbs. In the third step the second antigen (EGFR) was bound to the antibody-antigen complex as indicated. A positive signal compared to the no EGFR control in the third step demonstrates simultaneous binding. In the lower panel, His-tagged soluble EGFR (5 µg/ml) was bound to Octet tips, followed by binding of the bispecific antibody or the respective mAbs. In the third step the second antigen (IGF1R) was bound to the antibody-antigen complex as indicated. A positive signal compared to the no IGF1R control in the third step demonstrates simultaneous binding.

First, the Fc heterodimerization mutations were introduced into the CH3 domain of other Fc regions and the functionality of such bispecific antibodies was tested in binding studies. To this end, the mp3 heterodimer mutations (S364K/K409S and K370S/F405K) were cloned into an IgG1 agly T299A scaffold, which lacks the N-linked glycosylation at Asn297 and therefore has reduced effector function compared to glycosylated IgG1. A bispecific antibody with this Fc region in the form of an asymmetric IgG with an Efab of the anti-EGFR antibody M60-A02 and a regular Fab of the anti-IGF-1R antibody M13.006 was produced by transient expression in CHO cells (FIG. 11A). The resulting bispecific antibody showed robust simultaneous binding to both ligands in a sandwich-format Octet binding assay (FIG. 11B), demonstrating that the bispecific antibody efficiently formed from the four co-expressed chains (plasmids pMP463, pMP402, pMP405, pMP407). Thus, the Fc heterodimerization strategy by lysine repositioning appears to function independent of the Fc glycosylation.

```
pMP402 M60 Efab IgG1 agly T299A mp3a S364K/K409S
                                            (SEQ ID NO: 83)
  1 EVQLLESGGG LVQPGGSLRL SCAASGFTFS DYIMHWVRQA PGKGLEWVSV

51 ISSSGGDTSY ADSVKGRFTI SRDNSKNTLY LQMNSLRAED TAVYYCAKVL

101 AGYFDWLPFD YWGQGTLVTV SSASTKGPTV KILQSICDGG GHFPPTIQLL

151 CLVSGYTPGT IQITWLEDGQ VMDVDLSTAS TTQEGELAST QSELTLSQKH

201 WLSDRTYTCQ VTYQGHTFED STKKCASDKT HTCPPCPAPE LLGGPSVFLF

251 PPKPKDTLMI SRTPEVTCVV VDVSHEDPEV KFNWYVDGVE VHNAKTKPRE

301 EQYNSAYRVV SVLTVLHQDW LNGKEYKCKV SNKALPAPIE KTISKAKGQP

351 REPQVYTLPP SRDELTKNQV KLTCLVKGFY PSDIAVEWES NGQPENNYKT

401 TPPVLDSDGS FFLYSSLTVD KSRWQQGNVF SCSVMHEALH NHYTQKSLSL

451 SPG pMP405 C06 IgG1 agly T299A mp3b K370S/F405K
                                            (SEQ ID NO: 84)
  1 EVQLLESGGG LVQPGGSLRL SCAASGFTFS IYRMQWVRQA PGKGLEWVSG

51 ISPSGGTTWY ADSVKGRFTI SRDNSKNTLY LQMNSLRAED TAVYYCARWS

101 GGSGYAFDIW GQGTMVTVSS ASTKGPSVFP LAPSSKSTSG GTAALGCLVK

151 DYFPEPVTVS WNSGALTSGV HTFPAVLQSS GLYSLSSVVT VPSSSLGTQT

201 YICNVNHKPS NTKVDKKVEP KSCDKTHTCP PCPAPELLGG PSVFLFPPKP

251 KDTLMISRTP EVTCVVVDVS HEDPEVKFNW YVDGVEVHNA KTKPREEQYN

301 SAYRVVSVLT VLHQDWLNGK EYKCKVSNKA LPAPIEKTIS KAKGQPREPQ

351 VYTLPPSRDE LTKNQVSLTC LVSGFYPSDI AVEWESNGQP ENNYKTTPPV

401 LDSDGSFKLY SKLTVDKSRW QQGNVFSCSV MHEALHNHYT QKSLSLSPG
```

Figure 12:
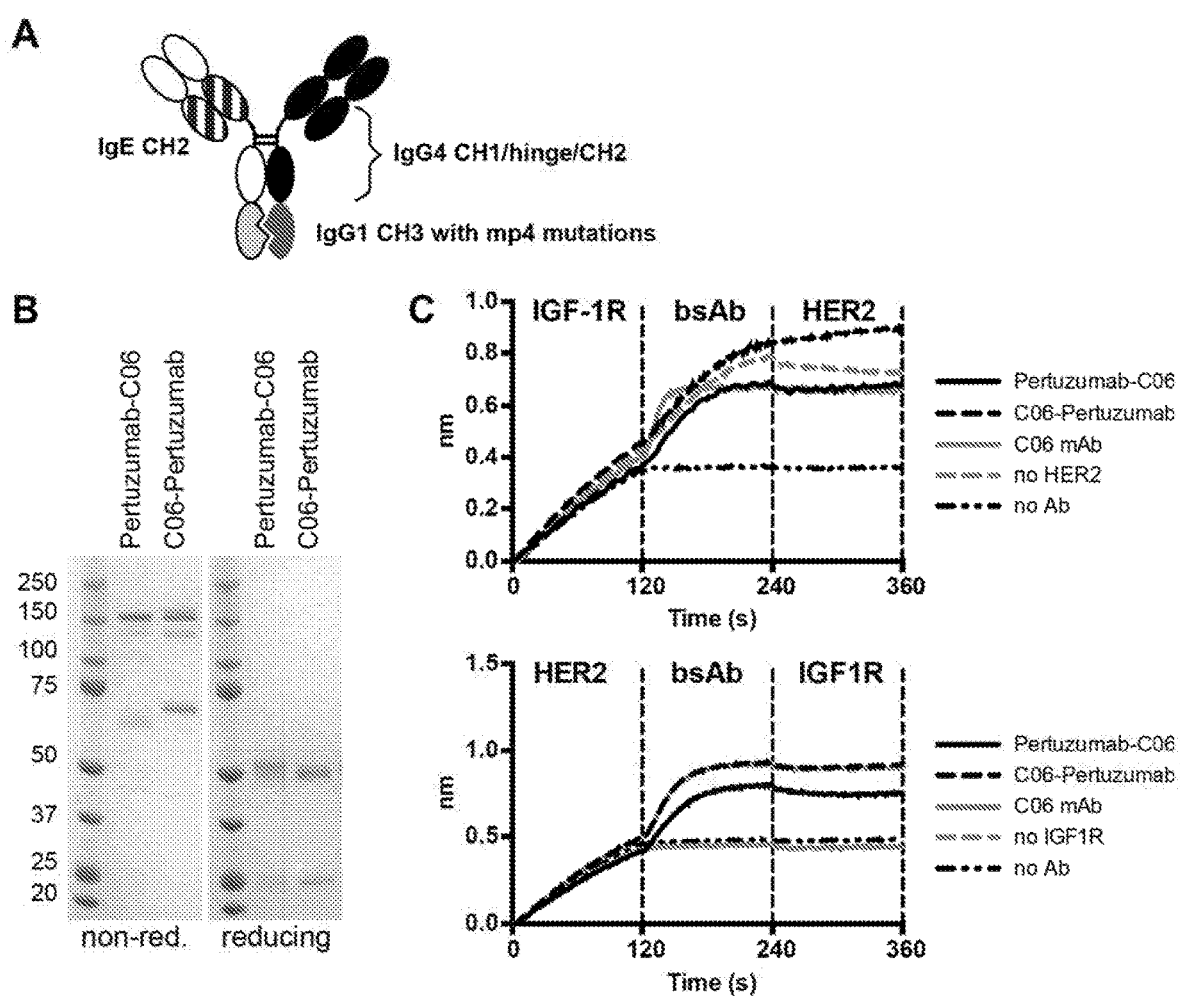
FIG. 12A is a schematic drawing of a bispecific antibody with an Efab and an IgG4P/IgG1 constant region containing mp4 heterodimer. The antibody also comprises an N297Q substitution in the constant domain (IgG4P/IgG1 agly).
FIG. 12B is a photograph of a gel of bispecific antibodies as shown in (A) that were generated with the anti-HER2 antibody Pertuzumab and the anti-IGF1R antibody C06 in both orientations, with the antibody named first always being an Efab. Aliquots of the protein-A-purified material from CHO cells were analyzed by SDS-PAGE.
FIG. 12C shows the results of binding when tested by Octet using soluble IGF1R and HER2 protein. In the upper panel, His-tagged soluble IGF1R (5 µg/ml) was bound to Octet tips, followed by binding of the bispecific antibody or the respective mAbs. In the third step the second antigen (HER2) was bound to the antibody-antigen complex as indicated. A positive signal compared to the no HER2 control in the third step demonstrates simultaneous binding. In the lower panel, His-tagged soluble HER2 (5 µg/ml) was bound to Octet tips, followed by binding of the bispecific antibody or the respective mAbs. In the third step the second antigen (IGF1R) was bound to the antibody-antigen complex as indicated. A positive signal compared to the no IGF1R control in the third step demonstrates simultaneous binding.

Second, to test the heavy chain heterodimerization in another Fc format, the mp4 heterodimer mutations (S364K/K409L and K370S/V397I/F405K) were cloned into an IgG4P/IgG1 agly (N297Q) hybrid constant domain, which pairs the minimal effector function of an aglycosylated IgG4 CH2 domain with the stability of an IgG1 CH3 domain (FIG. 12). This Fc also contains the hinge-stabilizing mutation S228P. Hence, bispecific antibodies with this hybrid IgG4P/IgG1 constant domain and the variable domains of the anti-HER2 antibody Pertuzumab and the anti-IGF-1R antibody C06 were generated. The variable domains were used in both orientations, on the chain A as Efab or on the chain B as regular Fab, respectively. The antibody was again produced in CHO cells, and protein A-purified material was used in Octet binding studies (FIG. 12). Interestingly, the purified bispecific antibodies showed simultaneous binding to both antigens only when IGF1R was loaded first followed by antibody and HER2 (FIG. 12C), but not when tested in the reverse order, which might be due to the different location of tags on the soluble antigens.

Figure 13:
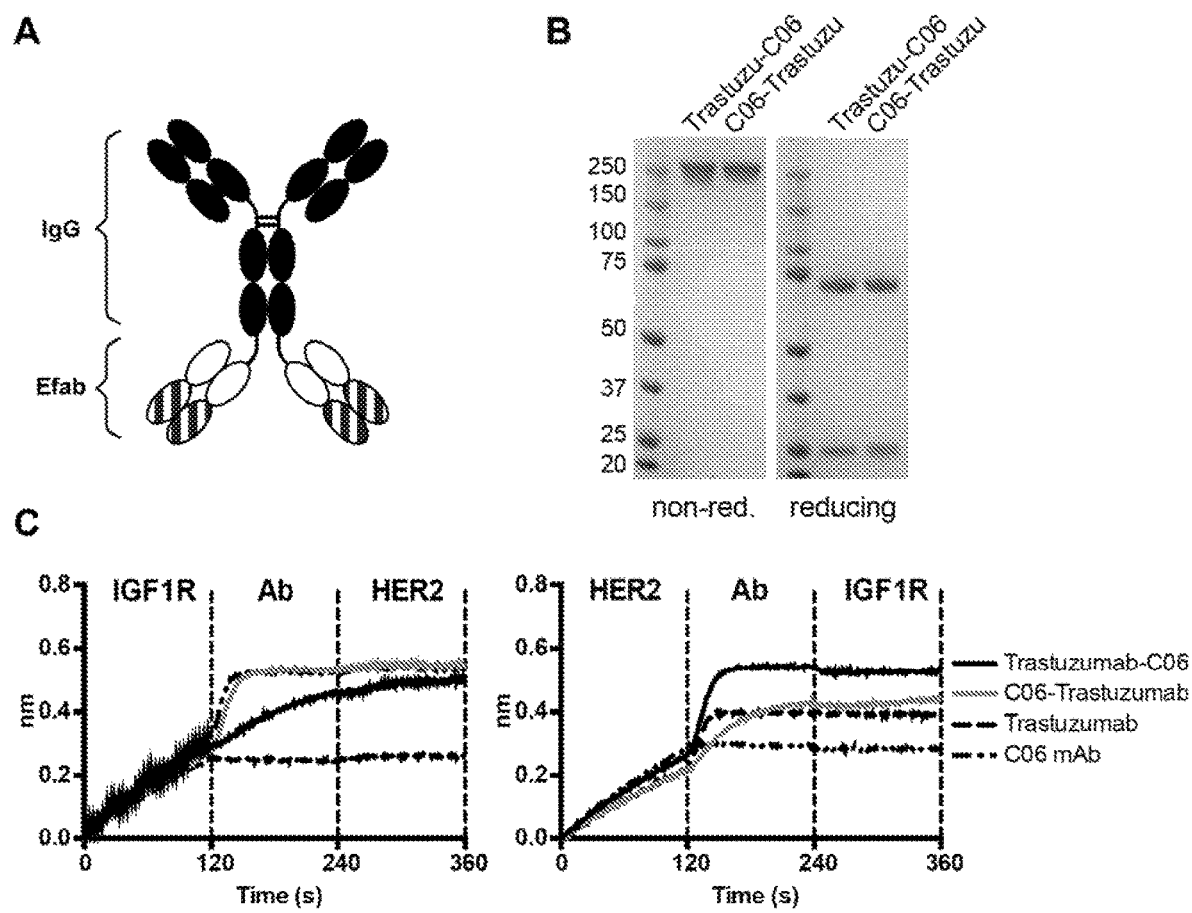
FIG. 13A is a schematic drawing of an IgG with an Efab fused to the C-terminus of the heavy chain (an "Mab-Fab").
FIG. 13B is a photograph of a gel of Mab-Fabs of Trastuzumab and the anti-IGF-1R antibody C06. Mab-Fabs of Trastuzumab and the anti-IGF-1R antibody C06 were transiently expressed in CHO cells and purified by protein A. SDS-PAGE shows that the proteins assembled correctly forming the ~240 kDa Mab-Fabs.
FIG. 13C shows the results of binding when tested by Octet. His-tagged soluble IGF1R or HER2 (5 µg/ml) was loaded onto Octet tips allowing capture of the bispecific antibody (200 nM) in the next step. Subsequent binding of the second ligand (15 µg/ml) demonstrates simultaneous binding of both ligands by the bispecific antibody.

Third, the bispecific technology was considered in the context of a Mab-Fab. A different way to construct a bispecific antibody is the Mab-Fab, which contains an IgG with a Fab fused to the C-terminus of the heavy chain (FIG. 13A). This format resembles a symmetric molecule with two identical heavy chains, making the Fc heterodimer technology unnecessary. However, the presence of two different Fabs, each containing its unique light chain, requires a light chain pairing solution. To test whether an Efab would function in this context to promote correct light chain assembly, a Mab-Fab was constructed with the anti-HER2 antibody Trastuzumab as IgG1 with an Efab of the anti-IGF-1R antibody C06 fused to its C-terminus (FIG. 13). Additionally, the inverse construct of C06 as IgG1 with an Efab of Trastuzumab fused to the C-terminus was also generated. In both cases the Efab was linked at the N-terminus of its heavy chain with a single G4S(SEQ ID NO:56)-linker to the C-terminus of the IgG heavy chain. The Mab-Fabs were again produced in CHO transients by co-expression of three plasmids (one heavy and two light chains, pMP759/pMP519/pMP511 or pMP760/pMP528/pMP407), and purified by protein A. Analysis of the purified material by SDS-PAGE showed that the three chains of the Mab-Fab assembled correctly into the 250 kDa protein (FIG. 13B). Furthermore, the bispecific antibodies showed some degree of simultaneous binding in a sandwich Octet binding assay (FIG. 13C). However, this simultaneous binding was only observed when the Efab was bound first, irrespective of whether C06 or Trastuzumab was the Efab, suggesting some form of steric hindrance in this format could affect the simultaneous binding of both antigens.

```
pMP759 Trastuzumab IgG1-C06 EFab
                                                         (SEQ ID NO: 85)
    1 EVQLVESGGG LVQPGGSLRL SCAASGFNIK DTYIHWVRQA PGKGLEWVAR

51 IYPTNGYTRY ADSVKGRFTI SADTSKNTAY LQMNSLRAED TAVYYCSRWG

101 GDGFYAMDYW GQGTLVTVSS ASTKGPSVFP LAPSSKSTSG GTAALGCLVK

151 DYFPEPVTVS WNSGALTSGV HTFPAVLQSS GLYSLSSVVT VPSSSLGTQT

201 YICNVNHKPS NTKVDKKVEP KSCDKTHTCP PCPAPELLGG PSVFLFPPKP

251 KDTLMISRTP EVTCVVVDVS HEDPEVKFNW YVDGVEVHNA KTKPREEQYN

301 STYRVVSVLT VLHQDWLNGK EYKCKVSNKA LPAPIEKTIS KAKGQPREPQ

351 VYTLPPSRDE LTKNQVSLTC LVKGFYPSDI AVEWESNGQP ENNYKTTPPV

401 LDSDGSFFLY SKLTVDKSRW QQGNVFSCSV MHEALHNHYT QKSLSLSPGS

451 GGGGSEVQLL ESGGGLVQPG GSLRLSCAAS GFTFSIYRMQ WVRQAPGKGL

501 EWVSGISPSG GTTWYADSVK GRFTISRDNS KNTLYLQMNS LRAEDTAVYY

551 CARWSGGSGY AFDIWGQGTM VTVSSASTKG PTVKILQSIC DGGGHFPPTI

601 QLLCLVSGYT PGTIQITWLE DGQVMDVDLS TASTTQEGEL ASTQSELTLS

651 QKHWLSDRTY TCQVTYQGHT FEDSTKKCA pMP511 C06 Efab light chain
                                                         (SEQ ID NO: 86)
    1 DIQMTQSPLS LSASVGDRVT ITCQASRDIR NYLNWYQQKP GKAPKLLIYD

51 ASSLQTGVPS RFGGSGSGTD FSFTIGSLQP EDEATYYCQQ FDSLPHTFGQ

101 GTKLEIKRTV AAPTVKILQS SCDGGGHFPP TIQLLCLVSG YTPGTIQITW

151 LEDGQVMDVD LSTASTTQEG ELASTQSELT LSQKHWLSDR TYTCQVTYQG

201 HTFEDSGKKC A pMP519 Trastuzumab kappa light chain
                                                         (SEQ ID NO: 87)
    1 DIQMTQSPSS LSASVGDRVT ITCRASQDVN TAVAWYQQKP GKAPKLLIYS

51 ASFLYSGVPS RFSGSRSGTD FTLTISSLQP EDFATYYCQQ HYTTPPTFGQ

101 GTKVEIKRTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201 LSSPVTKSFN RGEC
```

-continued pMP760 C06-IgG1-Trastuzumab Efab (SEQ ID NO: 88)

```
  1 EVQLLESGGG LVQPGGSLRL SCAASGFTFS IYRMQWVRQA PGKGLEWVSG

51 ISPSGGTTWY ADSVKGRFTI SRDNSKNTLY LQMNSLRAED TAVYYCARWS

101 GGSGYAFDIW GQGTMVTVSS ASTKGPSVFP LAPSSKSTSG GTAALGCLVK

151 DYFPEPVTVS WNSGALTSGV HTFPAVLQSS GLYSLSSVVT VPSSSLGTQT

201 YICNVNHKPS NTKVDKKVEP KSCDKTHTCP PCPAPELLGG PSVFLFPPKP

251 KDTLMISRTP EVTCVVVDVS HEDPEVKFNW YVDGVEVHNA KTKPREEQYN

301 STYRVVSVLT VLHQDWLNGK EYKCKVSNKA LPAPIEKTIS KAKGQPREPQ

351 VYTLPPSRDE LTKNQVSLTC LVKGFYPSDI AVEWESNGQP ENNYKTTPPV

401 LDSDGSFFLY SKLTVDKSRW QQGNVFSCSV MHEALHNHYT QKSLSLSPGS

451 GGGGSEVQLV ESGGGLVQPG GSLRLSCAAS GFNIKDTYIH WVRQAPGKGL

501 EWVARIYPTN GYTRYADSVK GRFTISADTS KNTAYLQMNS LRAEDTAVYY

551 CSRWGGDGFY AMDYWGQGTL VTVSSASTKG PTVKILQSIC DGGGHFPPTI

601 QLLCLVSGYT PGTIQITWLE DGQVMDVDLS TASTTQEGEL ASTQSELTLS

651 QKHWLSDRTY TCQVTYQGHT FEDSTKKCA
```

Figure 14:
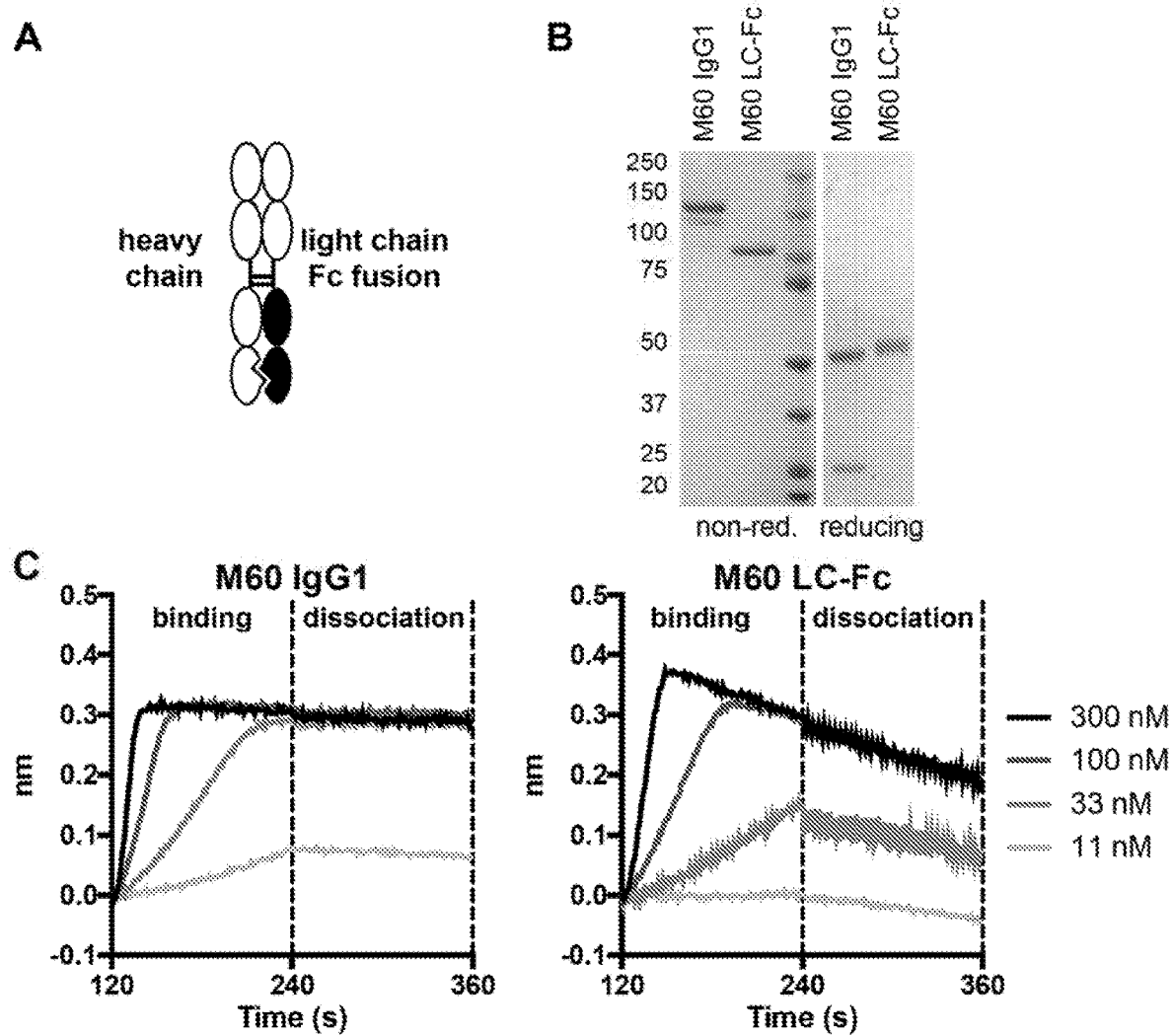
FIG. 14A is a schematic drawing of a monovalent antibody containing a LC-Fc fusion and Fc heterodimer mutations.
FIG. 14B is a photograph of a gel with the LC-Fc monovalent antibody and the corresponding bivalent IgG1 (anti-EGFR M60-A02) that were produced from CHO cells. SDS-PAGE of protein-A purified material shows clean assembly of the monovalent LC-Fc antibody.
FIG. 14C are graphs depicting monovalent LC-Fc and the bivalent IgG in Octet binding studies at various concentrations. The monovalent LC-Fc lacks avid binding and dissociation of the antigen-antibody complex is seen.

Fourth, in addition to the various applications in generating bispecifics, the Fc-heterodimerization technology can also be utilized to generate a monospecific monovalent antibody. A heterodimer between a half antibody and a free Fc as shown in FIG. 3 is one such example of a monospecific monovalent. Another example is the direct fusion of a LC to an Fc, which is then co-expressed with the matching heavy chain (FIG. 14A). An Fc heterodimerization strategy is required in this format to prevent the formation of homodimers of light chains or heavy chains. To test whether the mp4 Fc heterodimer would also be suitable to construct this type of monovalent monospecific antibody, a LC-Fc fusion construct was generated with the variable domain of the anti-EGFR antibody M60-A02. Expression of this plasmid (pMP533) together with the heavy chain of M60-A02 containing the corresponding Fc heterodimer mutation (plasmid pMP254) in CHO cells produced a single protein species (FIG. 14B). When this protein was analyzed in Octet binding it showed the characteristics of monovalent binding (FIG. 14C). Altogether, this data shows that the Fc heterodimerization by lysine repositioning appears to be a versatile and efficient way of generating monovalent monospecific antibodies.

Figure 15:
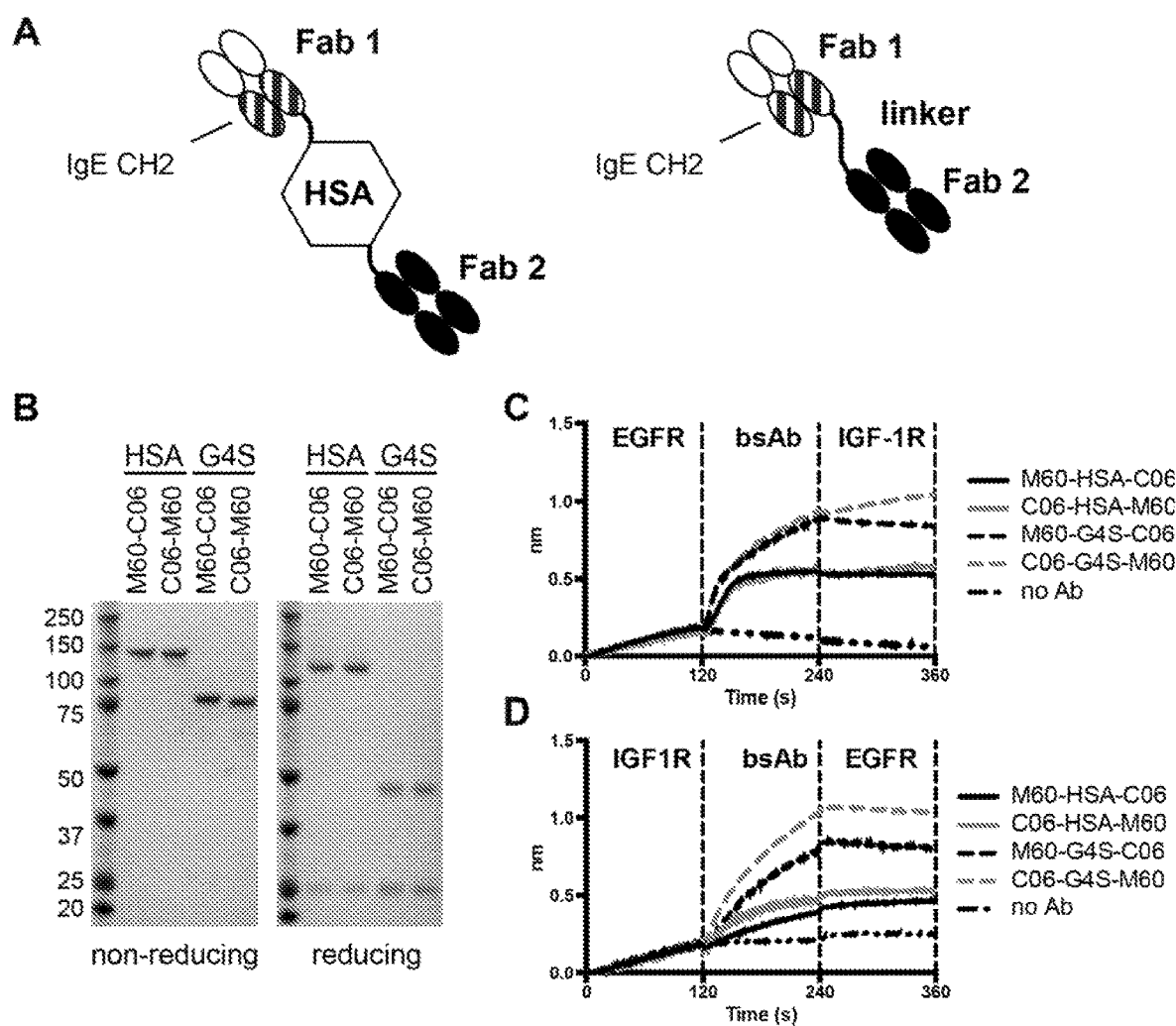
FIG. 15A provides schematic drawings of bispecific antibodies with an Efab linked to a regular Fab via HAS (left) a peptide linker (right).
FIG. 15B are photographs of gels of the two examples of bispecifics as shown in FIG. 15A that were expressed in CHO cells, and protein A-purified, and analyzed by SDS-PAGE. The anti-EGFR and anti IGF1R antibodies M60-A02 and M13.006 were used in both orientations, as Efab or as regular Fab, respectively.
FIG. 15C is a graph of purified bispecifics used in Octet binding studies. Simultaneous binding of both antigens by these bispecifics was observed only when the bispecific was bound to EGFR first followed by IGF-1R binding.
FIG. 15D is a graph of purified bispecifics used in Octet binding studies. Simultaneous binding of both antigens by these bispecifics was not observed when the bispecific was bound to IGF-1R first followed by EGFR binding.

Lastly, the use of the Efab light chain pairing solution was also tested in bispecific antibodies, which lack the Fc portion of an IgG. Such bispecifics can be generated for example by direct fusion of two Fabs with a peptide linker (FIG. 15A, right diagram). Alternatively, the peptide that links the two Fabs could be a heterologous protein such as human serum albumin (HSA) (FIG. 15A, left diagram). In either case, the pairing of the light and heavy chains of the two Fabs needs to be correct for the bispecific to function. Thus, the Efab light chain pairing solution could enable such a fusion of two Fabs into bispecific molecules. To test this, the M60-A02 and M13.006 antibodies were again used, and bispecifics were again generated with the two Fabs in both orientations. When these bispecifics were expressed in CHO cells they produced a single protein suggesting again that the antibody chains had assembled correctly (FIG. 15B).

When the antibodies were tested in Octet binding studies, simultaneous binding was again observed only in one particular orientation (FIG. 15C). Nonetheless, the present data shows that the Efab light chain pairing solution can be employed to efficiently generate bispecifics from two Fabs in various formats that lack the Fc of a normal IgG.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A tetravalent bispecific antibody comprising:
   (i) a first Fab and a second Fab,
   wherein the first Fab comprises a first heavy chain variable domain (first VH) and a first light chain variable domain (first VL), wherein the first VH and the first VL pair to form a first variable region that binds specifically to a first epitope of a first antigen, and
   wherein the second Fab comprises a second heavy chain variable domain (second VH) and a second light chain variable domain (second VL), wherein the second VH and the second VL pair to form a second variable region that binds specifically to the first epitope of the first antigen; and
   (ii) a whole antibody comprising a first heavy chain comprising a first hinge, a first IgG CH2 domain, a first IgG CH3 domain, and a third VH, a second heavy chain comprising a second hinge, a second IgG CH2 domain, a second IgG CH3 domain, and a fourth VH, a first light chain comprising a third VL, and a second light chain comprising a fourth VL, wherein the third VH and the third VL pair to form a third variable region that binds specifically to a first epitope of a second antigen, and wherein the fourth VH and the fourth VL pair to form a fourth variable region that binds specifically to the first epitope of the second antigen,
   wherein the third VH is either directly linked or linked via a linker of 1 to 25 amino acids to a first polypeptide, the third VL is either directly linked or linked via a linker of 1 to 25 amino acids to a second polypeptide, the fourth VH is either directly linked or linked via a linker of 1 to 25 amino acids to a third polypeptide, and the fourth VL is either directly linked or linked via a linker of 1 to 25 amino acids to a fourth polypeptide;
   wherein the first, second, third, and fourth polypeptides each comprise:
   (a) an amino acid sequence that is identical to amino acids 9-107 of the amino acid sequence of the CH2 domain of human immunoglobulin E (IgE) (SEQ ID NO:1);
   (b) an amino acid sequence that is identical to amino acids 9-107 of SEQ ID NO:1 with an N43Q mutation;
   (c) an amino acid sequence that is identical to amino acids 9-107 of SEQ ID NO:1 with a T45A or T45C mutation;

(d) an amino acid sequence that is identical to amino acids 9-107 of SEQ ID NO:1 with an S17I or S17T mutation; or (e) an amino acid sequence that is identical to amino acids 9-107 of SEQ ID NO:1 with a T103G or T103S mutation, wherein the numbering of the amino acid positions in (a) to (e) is according to SEQ ID NO:1;

or wherein (f) the first and third polypeptides each comprise an amino acid sequence that is identical to amino acids 6-104 of SEQ ID NO:3, and the second and fourth polypeptides each comprise an amino acid sequence that is identical to amino acids 6-104 of SEQ ID NO:4;

(g) the first and third polypeptides each comprise an amino acid sequence that is identical to amino acids 6-104 of SEQ ID NO:47, and the second and fourth polypeptides each comprise an amino acid sequence that is identical to amino acids 6-104 of SEQ ID NO:48;

(h) the first and third polypeptides each comprise an amino acid sequence that is identical to amino acids 6-104 of SEQ ID NO:49, and the second and fourth polypeptides each comprise an amino acid sequence that is identical to amino acids 6-104 of SEQ ID NO:50; or (i) the first and third polypeptides each comprise an amino acid sequence that is identical to amino acids 6-104 of SEQ ID NO:5, and the second and fourth polypeptides each comprise an amino acid sequence that is identical to amino acids 6-104 of SEQ ID NO:6;

and wherein the first polypeptide is either directly linked or linked via a linker of 1 to 25 amino acids to the N-terminus of the first hinge and the third polypeptide is either directly linked or linked via a linker of 1 to 25 amino acids to the N-terminus of the second hinge; and wherein the first Fab is connected to the C-terminus of the first IgG CH3 domain and the second Fab is connected to the C-terminus of the second IgG CH3 domain.

2. The tetravalent antibody of claim 1, wherein the first Fab is connected to the C-terminus of the first IgG CH3 domain through a linker of 1 to 25 amino acids and the second Fab is connected to the C-terminus of the second IgG CH3 domain through a linker of 1 to 25 amino acids.

3. The tetravalent antibody of claim 1, wherein the first polypeptide, the second polypeptide, the third polypeptide, and the fourth polypeptide each comprise amino acids 9-107 of the amino acid sequence set forth in SEQ ID NO:1.

4. The tetravalent antibody of claim 1, wherein the first polypeptide and the third polypeptide each comprise amino acids 6-104 of the amino acid sequence set forth in SEQ ID NO:3 and the second polypeptide and the fourth polypeptide each comprise amino acids 6-104 of the amino acid sequence set forth in SEQ ID NO:4.

5. The tetravalent antibody of claim 1, wherein the first polypeptide and the third polypeptide each comprise amino acids 6-104 of the amino acid sequence set forth in SEQ ID NO:5; and the second polypeptide and the fourth polypeptide each comprise amino acids 6-104 of the amino acid sequence set forth in SEQ ID NO:6.

6. The tetravalent antibody of claim 1, wherein the first polypeptide and the third polypeptide each comprise amino acids 6-104 of the amino acid sequence set forth in SEQ ID NO:47, and the second polypeptide and the fourth polypeptide each comprise amino acids 6-104 of the amino acid sequence set forth in SEQ ID NO:48.

7. The tetravalent antibody of claim 1, wherein the first polypeptide and the third polypeptide each comprise amino acids 6-104 of the amino acid sequence set forth in SEQ ID NO:49, and the second polypeptide and the fourth polypeptide each comprise amino acids 6-104 of the amino acid sequence set forth in SEQ ID NO:50.

8. The tetravalent antibody of claim 1, wherein the linker comprises a sequence selected from the group consisting of Gly; Ser; Gly Ser; Gly Gly Ser; Ser Gly Gly; the sequences of SEQ ID NO: 7, SEQ ID NOs: 9-10, SEQ ID NOs: 15-17, SEQ ID NOs: 55-71, and SEQ ID NOs: 77-78.

9. The tetravalent antibody of claim 5, wherein the first Fab is connected to the C-terminus of the first IgG CH3 domain through a linker of 1 to 25 amino acids and the second Fab is connected to the C-terminus of the second IgG CH3 domain through a linker of 1 to 25 amino acids.

10. The tetravalent antibody of claim 5, wherein the linker comprises a sequence selected from the group consisting of Gly; Ser; Gly Ser; Gly Gly Ser; Ser Gly Gly; the sequences of SEQ ID NO: 7, SEQ ID NOs: 9-10, SEQ ID NOs: 15-17, SEQ ID NOs: 55-71, and SEQ ID NOs: 77-78.

11. The tetravalent antibody of claim 1, wherein the first polypeptide, the second polypeptide, the third polypeptide, and the fourth polypeptide each comprise amino acids 9-107 of the amino acid sequence set forth in SEQ ID NO:1 with an N43Q mutation.

12. The tetravalent antibody of claim 1, wherein the first polypeptide, the second polypeptide, the third polypeptide, and the fourth polypeptide each comprise amino acids 9-107 of the amino acid sequence set forth in SEQ ID NO:1 with a T45A or T45C mutation.

13. The tetravalent antibody of claim 1, wherein the first polypeptide, the second polypeptide, the third polypeptide, and the fourth polypeptide each comprise amino acids 9-107 of the amino acid sequence set forth in SEQ ID NO:1 with an S17I or S17T mutation.

14. The tetravalent antibody of claim 1, wherein the first polypeptide, the second polypeptide, the third polypeptide, and the fourth polypeptide each comprise amino acids 9-107 of the amino acid sequence set forth in SEQ ID NO:1 with a T103G or T103S mutation.

15. A tetravalent bispecific antibody comprising:

(i) a first Fab and a second Fab, wherein the first Fab comprises a first heavy chain variable domain (first VH) and a first light chain variable domain (first VL), wherein the first VH and the first VL pair to form a first variable region that binds specifically to a first epitope of a first antigen, and wherein the second Fab comprises a second heavy chain variable domain (second VH) and a second light chain variable domain (second VL), wherein the second VH and the second VL pair to form a second variable region that binds specifically to the first epitope of the first antigen; and (ii) a whole antibody comprising a first heavy chain comprising a first hinge, a first IgG CH2 domain, a first IgG CH3 domain, and a third VH, a second heavy chain comprising a second hinge, a second IgG CH2 domain, a second IgG CH3 domain, and a fourth VH, a first light chain comprising a third VL, and a second light chain comprising a fourth VL, wherein the third VH and the third VL pair to form a third variable region that binds specifically to a first epitope of a second antigen, and wherein the fourth VH and the fourth VL pair to form a fourth variable region that binds specifically to the first epitope of the second antigen, wherein the third VH is either directly linked or linked via a linker of 1 to 25 amino acids to a first polypeptide, the third VL is either directly linked or linked via a linker of 1 to 25 amino acids to a second polypeptide, the fourth VH is either directly linked or linked via a linker of 1 to 25 amino acids to a third polypeptide, and the fourth VL is either directly linked or linked via a linker of 1 to 25 amino acids to a fourth polypeptide;

wherein the first, second, third, and fourth polypeptides each comprise
(a) an amino acid sequence that is identical to amino acids 7-112 of the amino acid sequence of the CH2 domain of human immunoglobulin M (IgM) (SEQ ID NO:2;
(b) an amino acid sequence that is identical to amino acids 7-112 of SEQ ID NO:2 with an N105Q mutation;
(c) an amino acid sequence that is identical to amino acids 7-112 of SEQ ID NO:2 with an S107A or S107C mutation;
(d) an amino acid sequence that is identical to amino acids 7-110 of SEQ ID NO:2;
(e) an amino acid sequence that is identical to amino acids 7-110 of SEQ ID NO:2 with an N105Q mutation; or
(f) an amino acid sequence that is identical to amino acids 7-110 of SEQ ID NO:2 with an S107A or S107C mutation, wherein the numbering of the amino acid positions in (a) to (f) is according to SEQ ID NO:2;

wherein the first polypeptide is either directly linked or linked via a linker of 1 to 25 amino acids to the N-terminus of the first hinge and the third polypeptide is either directly linked or linked via a linker of 1 to 25 amino acids to the N-terminus of the second hinge; and wherein the first Fab is connected to the C-terminus of the first IgG CH3 domain and the second Fab is connected to the C-terminus of the second IgG CH3 domain.

16. The tetravalent antibody of claim 15, wherein the first Fab is connected to the C-terminus of the first IgG CH3 domain through a linker of 1 to 25 amino acids and the second Fab is connected to the C-terminus of the second IgG CH3 domain through a linker of 1 to 25 amino acids.

17. The tetravalent antibody of claim 15, wherein the first polypeptide, the second polypeptide, the third polypeptide, and the fourth polypeptide each comprise amino acids 7-112 of the amino acid sequence set forth in SEQ ID NO:2.

18. The tetravalent antibody of claim 15, wherein the linker comprises a sequence selected from the group consisting of Gly; Ser; Gly Ser; Gly Gly Ser; Ser Gly Gly; the sequences of SEQ ID NO: 7, SEQ ID NOs: 9-10, SEQ ID NOs: 15-17, SEQ ID NOs: 55-71, and SEQ ID NOs: 77-78.

19. The tetravalent antibody of claim 15, wherein the first polypeptide, the second polypeptide, the third polypeptide, and the fourth polypeptide each comprise amino acids 7-112 of the amino acid sequence set forth in SEQ ID NO:2 with an N105Q mutation.

20. The tetravalent antibody of claim 15, wherein the first polypeptide, the second polypeptide, the third polypeptide, and the fourth polypeptide each comprise amino acids 7-112 of the amino acid sequence set forth in SEQ ID NO:2 with an S107A or S107C mutation.

21. The tetravalent antibody of claim 15, wherein the first polypeptide, the second polypeptide, the third polypeptide, and the fourth polypeptide each comprise amino acids 7-110 of the amino acid sequence set forth in SEQ ID NO:2.

22. The tetravalent antibody of claim 15, wherein the first polypeptide, the second polypeptide, the third polypeptide, and the fourth polypeptide each comprise amino acids 7-110 of the amino acid sequence set forth in SEQ ID NO:2 with an N105Q mutation.

23. The tetravalent antibody of claim 15, wherein the first polypeptide, the second polypeptide, the third polypeptide, and the fourth polypeptide each comprise amino acids 7-110 of the amino acid sequence set forth in SEQ ID NO:2 with an S107A or S107C mutation.

24. The tetravalent antibody of claim 22, wherein the first Fab is connected to the C-terminus of the first IgG CH3 domain through a linker of 1 to 25 amino acids and the second Fab is connected to the C-terminus of the second IgG CH3 domain through a linker of 1 to 25 amino acids.

25. The tetravalent antibody of claim 22, wherein the linker comprises a sequence selected from the group consisting of Gly; Ser; Gly Ser; Gly Gly Ser; Ser Gly Gly; the sequences of SEQ ID NO: 7, SEQ ID NOs: 9-10, SEQ ID NOs: 15-17, SEQ ID NOs: 55-71, and SEQ ID NOs: 77-78.

* * * * *